US007601738B2

(12) United States Patent
Bleisch et al.

(10) Patent No.: US 7,601,738 B2
(45) Date of Patent: Oct. 13, 2009

(54) EXCITATORY AMINO ACID RECEPTOR ANTAGONISTS

(75) Inventors: Thomas John Bleisch, Noblesville, IN (US); Jose Antonio Martinez-Perez, S.S. de los Reyes (ES); Paul Leslie Ornstein, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 587 days.

(21) Appl. No.: 11/302,869

(22) Filed: Dec. 14, 2005

(65) Prior Publication Data

US 2006/0100237 A1 May 11, 2006

Related U.S. Application Data

(63) Continuation of application No. 10/450,667, filed as application No. PCT/US01/45857 on Dec. 19, 2001, now Pat. No. 7,205,313.

(30) Foreign Application Priority Data

Jan. 5, 2001 (EP) .................................. 01500004

(51) Int. Cl.
*C07D 217/00* (2006.01)
*A61K 31/45* (2006.01)
(52) U.S. Cl. ...................................... 514/307; 546/146
(58) Field of Classification Search ....................... None
See application file for complete search history.

(56) References Cited

U.S. PATENT DOCUMENTS

| 5,356,902 A | 10/1994 | Ornstein |
| 5,446,051 A | 8/1995 | Ornstein |
| 5,670,516 A | 9/1997 | Arnold et al. |
| 5,767,117 A | 6/1998 | Moskowitz |

FOREIGN PATENT DOCUMENTS

| EP | 0 590 789 | 4/1994 |
| WO | WO 98/45270 | 10/1998 |
| WO | WO 01/01972 | 1/2001 |
| WO | WO 01/02367 | 1/2001 |
| WO | WO 01/46173 | 6/2001 |

OTHER PUBLICATIONS

Bleisch, et al., "Structurre-Activity Studies of Aryl-Spaced Decahydroisoquinoline-3-Carboxylic Acid AMPA Receptor Antagonists," Bioorganic & Medicinal Chemistry Letters, vol. 7, No. 9, pp. 1161-1166 (1997).
Martinez-Perez, "Structure-Activity Study of Glu5 Kainate Receptor Antagonists—Application of Prodrug Strategy for Oral Efficacy in Pain Models" (oral presentation given by one of the named inventors at the Frontiers in Medicinal Chemistry Meeting, Leipzig, Germany Mar. 15, 2005.

Y. Sahara, et al., "Glutamate Receptor Subunits GluR5 and KA-2 Are Coexpressed in Rat Trigeminal Ganglion Neurons," *The Journal of Neuroscience*, 17 (17), pp. 6611-6620 (1997).
Z. Alam, et al., "Plasma levels of neuroexcitatory amino acids in patients with migraine or tension headache," *Journal of Neurological Sciences*, 156, pp. 102-106 (1998).
Proctor, et al., "Possible role of GluR5 glutamate receptors in spinal nociceptive processing in the anaesthetized rat," Journal of Physiology (1997) 504. p. 101P-102P.
Nikam, et al., The Search for AMPA/Gly (N) receptor antagonists, Drugs of the Future (1999) 24(10), 1107-1124.
O'Neill, M.J., et al., "Decahydroisoquinolines: Novel competitive AMPA/kainite antagonists with neuroprotective effects in global cerebral ischaemia," Neuropharmacology 37 (1998) 1211-1222.
Proctor, M.J., et al., "Actions of kainite and AMPA selective glutamate receptor ligands on nociceptive processing in the spinal cord," Neuropharmacology 37 (1998) 1287-1297.
Bleakman, D., "Kainate receptor pharmacology and physiology," Cellular and Molecular Life Sciences, 56/7-8 (1999) 558-556.
Simmons, R.M., et al., "Kainate GluR5 receptor subtype mediates the nociceptive response to formalin in the rat," Neuropharmacology 37(1) (1998) 25-36.
National Library of Medicine (NLM), Methesda, MD, US, Mitsilostas DD, et al., "Non-NMDA glutamate receptors modulate capsaicin induced c-fos expression within trigeminal nucleus caudalis," Database accession No. 10003939 & British Journal of Pharmacology (1999) 127 (3) 623-630.
May, Chemical Abstracts Registry No. 365530-78-5; Nov. 1, 2001; American Chemical Society (corresponds to Example 38 (step A) ).
May, Chemical Abstracts Registry No. 365530-79-6; Nov. 1, 2001; American Chemical Society.
May, Chemical Abstracts Registry No. 365530-80-9; Nov. 1, 2001; American Chemical Society (corresponds to Example 9).
May, Chemical Abstracts Registry No. 365530-81-0; Nov. 1, 2001; American Chemical Society (corresponds to Example 10).
May, Chemical Abstracts Registry No. 365530-82-1; Nov. 1, 2001; American Chemical Society (corresponds to free base of Example 9).
May, Chemical Abstracts Registry No. 365530-83-2; Nov. 1, 2001; American Chemical Society (corresponds to Examples 37 and 38).
May, Chemical Abstracts Registry No. 365530-84-3; Nov. 1, 2001; American Chemical Society (corresponds to hydrate of Example 9).
May, Chemical Abstracts Registry No. 365530-85-4; Nov. 1, 2001; American Chemical Society (corresponds to free base of Example 9).

*Primary Examiner*—Zinna N Davis
(74) *Attorney, Agent, or Firm*—Alexander Wilson

(57) ABSTRACT

The present invention provides novel compounds of Formula (I) and Formula (I(a)), or the pharmaceutically acceptable salts thereof; methods for treating neurological disorders and neurodegenerative diseases, particularly pain and migraine, comprising administering a compound of Formula (I) or Formula (I(a)); and processes for preparing compounds of Formula (I) or Formula (I(a)).

7 Claims, No Drawings

EXCITATORY AMINO ACID RECEPTOR ANTAGONISTS

This is a continuation of U.S application Ser. No. 10/450,667, filed Dec. 1, 2003, now U.S. Pat. No. 7,205,313, which is a 371 (national filing) of PCT/US01/45857, filed Dec. 19, 2001 which claims priority to European Patent Application EP01500004.5, filed Jan. 5, 2001.

BACKGROUND OF THE INVENTION

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathways in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). Molecular biological studies have established that AMPA receptors are composed of subunits ($GluR_1$-$GluR_4$), which can assemble to form functional ion channels. Five kainate receptors have been identified which are classified as either High Affinity (KA1 and KA2) or Low Affinity (composed of $GluR_5$, $GluR_6$, and/or $GluR_7$ subunits). Bleakman et al., *Molecular Pharmacology*, 49, No.4, 581,(1996). The second general type of receptor is the G-protein coupled or second messenger-linked "metabotropic" excitatory amino acid receptor. This second type is coupled to multiple second messenger systems that lead to enhanced phosphoinositide hydrolysis, activation of phospholipase D, increases or decreases in cAMP formation, and changes in ion channel function. Schoepp and Conn, *Trends in Pharmacol. Sci.*, 14, 13 (1993). Both types of excitatory amino acid receptor appear not only to mediate normal synaptic transmission along excitatory pathways, but also to participate in the modification of synaptic connections during development and throughout life. Schoepp, Bockaert, and Sladeczek, *Trends in Pharmacol Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of neurological disorders and conditions. The medical consequences of such neuronal degeneration makes the abatement of these degenerative neurological processes an important therapeutic goal. For instance, excitatory-amino acid receptor excitotoxicity has been implicated in the pathophysiology of numerous neurological disorders, including the etiology of cerebral deficits subsequent to cardiac bypass surgery and grafting, stroke, cerebral ischemia, spinal cord lesions resulting from trauma or inflammation, perinatal hypoxia, cardiac arrest, and hypoglycemic neuronal damage. In addition, excitotoxicity has been implicated in chronic neurodegenerative conditions including Alzheimer's Disease, Huntington's Chorea, inherited ataxias, AIDS-induced dementia, amyotrophic lateral sclerosis, idiopathic and drug-induced Parkinson's Disease, as well as ocular damage and retinopathy. Other neurological disorders implicated with excitotoxicity and/or glutamate dysfunction include muscular spasticity including tremors, drug tolerance and withdrawal, brain edema, convulsive disorders including epilepsy, depression, anxiety and anxiety related-disorders such as post-traumatic stress syndrome, tardive dyskinesia, and psychosis related to depression, schizophrenia, bipolar disorder, mania, and drug intoxication or addiction (see generally U.S. Pat. Nos. 5,446,051 and 5,670,516). Excitatory amino acid receptor antagonists may also be useful as analgesic agents and for treating or preventing various forms of headache, including cluster headache, tension-type headache, and chronic daily headache. In addition, published International Patent application WO 98/45720 reports that excitatory amino acid receptor excitotoxicity participates in the etiology of acute and chronic pain states including severe pain, intractable pain, neuropathic pain, post-traumatic pain.

It is also known that trigeminal ganglia, and their associated nerve pathways, are associated with painful sensations of the head and face such as headache and, in particular, migraine. Moskowitz (*Cephalalgia*, 12, 5-7, (1992) proposed that unknown triggers stimulate the trigeminal ganglia which in turn innervate vasculature within cephalic tissue, giving rise to the release of vasoactive neuropeptides from axons innervating the vasculature. These neuropeptides initiate a series of events leading to neurogenic inflammation of the meninges, a consequence of which is pain. This neurogenic inflammation is blocked by sumatriptan at doses similar to those required to treat acute migraine in humans. However, such doses of sumatriptan are associated with contraindications as a result of sumatriptan's attendant vasoconstrictive properties.(see MacIntyre, P. D., et al., *British Journal of Clinical Pharmacology*, 34, 541-546 (1992); Chester, A. H., et al., *Cardiovascular Research*, 24, 932-937 (1990); Conner, H. E., et al., *European Journal of Pharmacology*, 161, 91-94 (1990)). Recently, it has been reported that all five members of the kainate subtype of ionotropic glutamate receptors are expressed on rat trigeminal ganglion neurons, and in particular, high levels of $GluR_5$ and KA2 have been observed. (Sahara et al., *The Journal of Neuroscience*, 17(17), 6611 (1997)). As such, migraine presents yet another neurological disorder which may be implicated with glutamate receptor excitotoxicity.

The use of a neuroprotective agent, such as an excitatory amino acid receptor antagonist, is believed to be useful in treating or preventing all of the aforementioned disorders and/or reducing the amount of neurological damage associated with these disorders. For example, studies have shown that AMPA receptor antagonists are neuroprotective in focal and global ischemia models. The competitive AMPA receptor antagonist NBQX (2,3-dihydroxy-6-nitro-7-sulfamoylbenzo[f]quinoxaline) has been reported effective in preventing global and focal ischemic damage. Sheardown et al., *Science*, 247, 571 (1900); Buchan et al., *Neuroreport*, 2, 473 (1991); LaPeillet et al., *Brain Research*, 571, 115 (1992). The non-competitive AMPA receptor antagonists GKYI 52466 has been shown to be an effective neuroprotective agent in rat global ischemia models. LaPeillet et al., *Brain Research*, 571, 115 (1992). European Patent Application Publication No. 590789A1 and U.S. Pat. Nos. 5,446,051 and 5,670,516 disclose that certain decahydroisoquinoline derivative compounds are AMPA receptor antagonists and, as such, are useful in the treatment of a multitude of disorders conditions, including pain and migraine headache. WO 98/45270 discloses that certain decahydroisoquinoline derivative compounds are selective antagonists of the iGluR$_5$ receptor and are useful for the treatment of various types of pain, including; severe, chronic, intractable, and neuropathic pain.

In accordance with the present invention, Applicants have discovered novel compounds that are antagonists of the iGluR$_5$ receptor subtype and, thus, could be useful in treating the multitude of neurological disorders or neurodegenerative diseases, as discussed above. Such antagonists could address a long felt need for safe and effective treatments for neruological disorders, without attending side effects. The treatment of neurological disorders and neurodegenerative diseases is hereby furthered.

SUMMARY OF THE INVENTION

The present invention provides a compound of Formula I

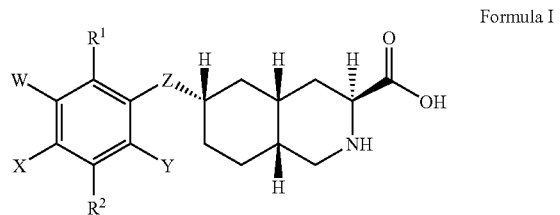

Formula I wherein

Z represents a sulfur or oxygen atom;

$R^1$ represents hydrogen, CN, $(C_1-C_4)$alkyl-$CO_2H$, $CO_2H$, or tetrazole;

$R^2$ represents hydrogen, halo, aryl, substituted aryl, $CO_2H$, tetrazole, $(C_1-C_4)$alkyl, $(C_1-C_4)$alkylaryl, heterocycle, substituted heterocycle, $CF_3$, $NHR^3$, or O—$R^4$;

$R^3$ represents hydrogen, $(C_1-C_4)$alkyl, $(C_1-C_4)$alkylaryl, or aryl;

$R^4$ represents $(C_1-C_6)$alkyl, $(C_1-C_4)$alkylaryl, $(C_1-C_4)$alkyl-heterocycle, $(C_1-C_6)$alkyl$(C_3-C_{10})$cycloalkyl, $(C_3-C_{10})$cycloalkyl, $(C_1-C_4)$alkyl(substituted)aryl, aryl, or heterocycle; and W, X, and Y each independently represent hydrogen, halo, $(C_1-C_6)$alkyl, $(C_1-C_4)$alkoxy, aryl, substituted aryl, $CO_2H$, $CO(NH_2)$, $CF_3$, NH-aryl, $NH_2$, or $NO_2$, or optionally, X and $R^2$ together, or W and X together, or Y and $R^2$ together, along with the carbon atoms to which they are attached, form a benzo-fused group;

with the proviso that where Z is sulfur, then $R^1$ is hydrogen, $CO_2H$, or tetrazole, $R^2$ is hydrogen, Halo, $(C_1-C_4)$alkyl, or $CO_2H$, and W, X, and Y are each hydrogen, Halo, $(C_1-C_6)$alkyl, $CO_2H$, or $CO(NH_2)$;

or a pharmaceutically acceptable salt or prodrug thereof.

In another embodiment, the present invention provides a method of treating or preventing a neurological disorder, or neurodegenerative condition, comprising administering to a patient in need thereof an effective amount of a compound of Formula I or a pharmaceutically acceptable salt or prodrug thereof. Examples of such neurological disorders, or neurodegenerative conditions, include: cerebral deficits subsequent to cardiac bypass surgery and grafting; stroke; cerebral ischemia; spinal cord lesions resulting from trauma or inflammation; perinatal hypoxia; cardiac arrest; hypoglycemic neuronal damage; Alzheimer's Disease; Huntington's Chorea; inherited ataxias; AIDS-induced dementia; amyotrophic lateral sclerosis; idiopathic and drug-induced Parkinson's Disease; ocular damage and retinopathy; muscular spasticity including tremors; drug tolerance and withdrawal; brain edema; convulsive disorders including epilepsy; depression; anxiety and anxiety related disorders such as post-traumatic stress syndrome; tardive dyskinesia; psychosis related to depression, schizophrenia, bipolar disorder, mania, and drug intoxication or addiction; headache, including cluster headache, tension-type headache, and chronic daily headache; migraine; and acute and chronic pain states including severe pain, intractable pain, neuropathic pain, and post-traumatic pain.

More specifically, the present invention provides a method of treating or preventing pain or migraine comprising administering to a patient in need thereof an effective amount of a compound of Formula I, or a pharmaceutically acceptable salt or prodrug thereof.

In addition, the present invention provides pharmaceutical compositions of compounds of Formula I, including the pharmaceutically acceptable salts, prodrugs, and hydrates thereof, comprising, a compound of Formula I in combination with a pharmaceutically acceptable carrier, diluent or excipient. This invention also encompasses novel intermediates, and processes for the synthesis of the compounds of Formula I.

Specifically, The present invention also provides a process for making compounds of Formula I(a):

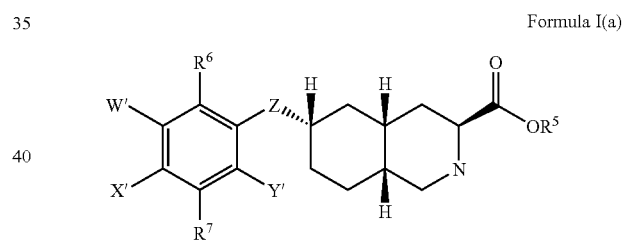

Formula I(a)

wherein,

Z represents oxygen $R^5$, $R^8$, and $R^{10}$ each independently represents hydrogen, $(C_1-C_{20})$alkyl, $(C_2-C_6)$alkenyl, $(C_1-C_6)$alkylaryl, $(C_1-C_6)$alkyl$(C_3-C_{10})$cycloalkyl, $(C_1-C_6)$alkyl-N,N—$C_1-C_6$ dialkylamine, $(C_1-C_6)$alkyl-pyrrolidine, $(C_1-C_6)$alkyl-piperidine, or $(C_1-C_6)$alkyl-morpholine; with the proviso that where $R^7$ is $CO_2R^{10}$; or W', X', or Y' is $CO_2R^8$, then at least one, but no more than two of $R^5$, $R^8$, and $R^{10}$ is other than hydrogen;

$R^6$ represents tetrazole;

$R^7$ represents hydrogen, halo, aryl, substituted aryl, $CO_2R^{10}$, tetrazole, $(C_1-C_4)$alkyl, $(C_1-C_4)$alklaryl, heterocycle, substituted heterocycle, $CF_3$, $NHR^3$, or $OR^4$;

$R^3$ represents hydrogen, $(C_1-C_4)$alkyl, $(C_1-C_4)$alklaryl, or aryl;

$R^4$ represents $(C_1-C_6)$alkyl, $(C_1-C_4)$alkylaryl, $(C_1-C_4)$alkyl-heterocycle, $(C_1-C_6)$alkyl$(C_3-C_{10})$cycloalkyl, $(C_3-C_{10})$cycloalkyl, $(C_1-C_4)$alkyl(substituted)aryl, aryl, or heterocycle; and W', X' and Y' each independently represent hydrogen, halo, $(C_1-C_6)$alkyl, $CO_2R^8$, or $CO(NH_2)$; or optionally, X' and $R^7$ together, or W' and X' together, or Y' and $R^7$ together, along with the carbon atoms to which they are attached, form a benzo-fused group;

comprising combining a compound of structure (10):

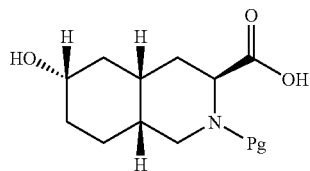
(10)

wherein Pg is a suitable nitrogen protecting group, with a suitable base in a suitable solvent followed by addition of a compound of structure (11b):

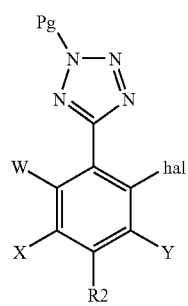
(11b)

wherein Pg is a suitable nitrogen protecting group;

$R^2$ represents hydrogen, halo, aryl, substituted aryl, $CO_2H$, tetrazole, $(C_1-C_4)$alkyl, $(C_1-C_4)$alkylaryl, heterocycle, substituted heterocycle, $CF_3$, $NHR^3$, or $OR^4$;

$R^3$ and $R^4$ are as defined above, and

W, X, and Y each independently represent hydrogen, halo, $(C_1-C_6)$alkyl, $(C_1-C_4)$alkoxy, aryl, substituted aryl, $CO_2H$, $CO(NH_2)$, $CF_3$, NH-aryl, $NH_2$, or $NO_2$, or optionally, X and $R^2$ together, or W and X together, or Y and $R^2$ together, along with the carbon atoms to which they are attached, form a benzo-fused group;

followed by esterification to a compound of structure (12b)

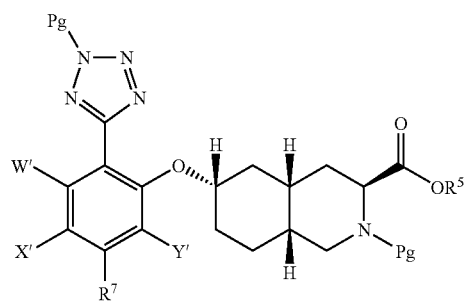
(12b)

wherein Pg, $R^5$, $R^7$, W', X', and Y' are as defined above; followed by removal of the nitrogen protecting groups, and precipitation with a suitable acid.

In a further embodiment, the present invention provides yet another process for synthesizing a compound of Formula I(a):

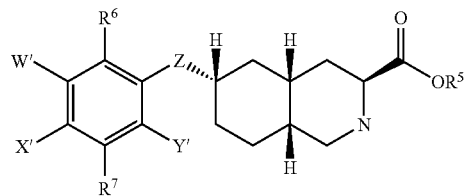
Formula I(a)

wherein,

Z represents oxygen;

$R^5$, $R^8$, and $R^{10}$ each independently represents hydrogen, $(C_1-C_{20})$alkyl, $(C_2-C_6)$alkenyl, $(C_1-C_6)$alkylaryl, $(C_1-C_6)$alkyl$(C_3-C_{10})$cycloalkyl, $(C_1-C_6)$alkyl-N,N—$C_1-C_6$ dialkylamine, $(C_1-C_6)$alkyl-pyrrolidine, $(C_1-C_6)$alkyl-piperidine, or $(C_1-C_6)$alkyl-morpholine; with the proviso that where $R^7$ is $CO_2R^{10}$; or W', X', or Y' is $CO_2R^8$, then at least one, but no more than two of $R^5$, $R^8$, and $R^{10}$ is other than hydrogen;

$R^6$ represents tetrazole;

$R^7$ represents hydrogen, halo, aryl, substituted aryl, $Co_2R^{10}$, tetrazole, $(C_1-C_4)$alkyl, $(C_1-C_4)$alkylaryl, heterocycle, substituted heterocycle, $CF_3$, $NHR^3$, or $OR^4$;

$R^3$ represents hydrogen, $(C_1-C_4)$alkyl, $(C_1-C_4)$alkylaryl, or aryl, $R^4$ represents $(C_1-C_6)$alkyl, $(C_1-C_4)$alkylaryl, $(C_1-C_4)$alkyl-heterocycle, $(C_1-C_6)$alkyl$(C_3-C_{10})$cycloalkyl, $(C_3-C_{10})$cycloalkyl, $(C_1-C_4)$alkyl(substituted)aryl, aryl, or heterocycle; and W', X' and Y' each independently represent hydrogen, halo, $(C_1-C_6)$alkyl, $CO_2R^8$, or $CO(NH_2)$; or optionally, X' and $R^7$ together, or W' and X' together, or Y' and $R^7$ together, along with the carbon atoms to which they are attached, form a benzo-fused group;

comprising combining a compound of structure (10):

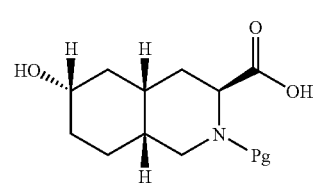
(10)

wherein Pg is a suitable nitrogen protecting group, with a suitable base in a suitable solvent, followed by addition of a compound of structure (11a):

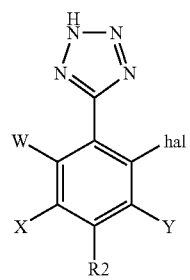
(11a)

wherein, $R^2$ represents hydrogen, halo, aryl, substituted aryl, $CO_2H$, tetrazole, $(C_1$-$C_4)$alkyl, $(C_1$-$C_4)$alkylaryl, heterocycle, substituted heterocycle, $CF_3$, $NHR^3$, or $OR^4$;

$R^3$ and $R^4$ are as defined above, and

W, X, and Y each independently represent hydrogen, halo, $(C_1$-$C_6)$alkyl, $(C_1$-$C_4)$alkoxy, aryl, substituted aryl, $CO_2H$, $CO(NH_2)$, $CF_3$, NH-aryl, $NH_2$, or $NO_2$, or optionally, X and $R^2$ together, or W and X together, or Y and $R^2$ together, along with the carbon atoms to which they are attached, form a benzo-fused group;

followed by deprotection of the nitrogen group, precipitation with a suitable acid, and crystallization of the hydrate salt of structure (12e):

(12e)

wherein R2, W, X, and Y are as defined above;

followed by treatment with a suitable alcohol in the presence suitable acid to effect the one step esterification and crystallization of Formula I(a).

The present invention also provides the use of a compound of Formula I of Formula I(a) for the manufacture of a medicament for treating or preventing a neurological disorder, or neurodegenerative condition.

More specifically, the present invention provides the use of a compound of Formula I or Formula I(a) for the manufacture of a medicament for treating or preventing pain or migraine.

DETAILED DESCRIPTION OF THE INVENTION

The present invention provides compounds functional as $iGluR_5$ receptor antagonists as well as pharmaceutically acceptable salts, prodrugs, and compositions thereof. These compounds are useful in treating or preventing neurological disorders, or neurodegenerative diseases, particularly pain and migraine. As such, methods for the treatment or prevention of neurological disorders, or neurodegenerative diseases, are also provided by the present invention.

In addition, it should be understood by the skilled artisan that all of the compounds useful for the methods of the present invention are available for prodrug formulation. As used herein, the term "prodrug" refers to a compound of Formula I which has been structurally modified such that in vivo the prodrug is converted, for example, by hydrolytic, oxidative, reductive, or enzymatic cleavage into the parent compound (e.g. the carboxylic acid (drug), or as the case may be the parent dicarboxylic acid (drug)) as given by Formula I. Such prodrugs may be, for example, metabolically labile mono- or diester derivatives of the parent compounds having a carboxylic acid group(s). It is to be understood that the present invention includes any such prodrugs, such as metabolically labile ester or diester derivatives of compounds of the Formula. In all cases, the use of the compounds described herein as prodrugs is contemplated, and often is preferred, and thus, the prodrugs of all of the compounds provided are encompassed in the names of the compounds herein. Conventional procedures for the selection and preparation of suitable prodrugs are well known to one of ordinary skill in the art.

More specifically, examples of prodrugs of Formula I which are understood to be included within the scope of the present invention, are represented by Formulas Ia below:

Formula Ia wherein

Z is as defined hereinabove;

$R^5$ represents hydrogen, $(C_1$-$C_{20})$alkyl, $(C_2$-$C_6)$alkenyl, $(C_1$-$C_6)$alkylaryl, $(C_1$-$C_6)$alkyl$(C_3$-$C_{10})$Cycloalkyl, $(C_1$-$C_6)$alkyl-N,N—$C_1$-$C_6$ dialkylamine, $(C_1$-$C_6)$alkyl-pyrrolidine, $(C_1$-$C_6)$alkyl-piperidine, or $(C_1$-$C_6)$alkyl-morpholine;

$R^6$ represents hydrogen, CN, $(C_1$-$C_4)$alkyl-$CO_2R^9$, $CO_2R^9$, or tetrazole;

$R^7$ represents hydrogen, halo, aryl, substituted aryl, $CO_2R^{10}$, tetrazole, $(C_1$-$C_4)$alkyl, $(C_1$-$C_4)$alkylaryl, heterocycle, substituted heterocycle, $CF_3$, $NHR^3$, or O—$R^4$;

$R^3$ and $R^4$ are as defined hereinabove;

W', X' and Y' each independently represent hydrogen, halo, $(C_1$-$C_6)$alkyl, $CO_2R^8$, or $CO(NH_2)$; or optionally, X' and $R^7$ together, or W' and X' together, or Y' and $R^7$ together, along with the carbon atoms to which they are attached, form a benzo-fused group;

with the proviso that where Z is sulfur, then $R^6$ is hydrogen, $CO_2R^9$ or tetrazole, $R^7$ is hydrogen, Halo, $(C_1$-$C_4)$alkyl, or $CO_2R^{10}$, and W', X', and Y' are each independently hydrogen, Halo, $(C_1$-$C_6)$alkyl, $CO_2R^9$ or $CO(NH_2)$;

$R^8$, $R^9$, and $R^{10}$ each independently represent hydrogen, $(C_1$-$C_{20})$alkyl, $(C_2$-$C_6)$alkenyl, $(C_1$-$C_6)$alkylaryl, $(C_1$-$C_6)$alkyl$(C_3$-$C_{10})$cycloalkyl, $(C_1$-$C_6)$alkyl-NN—$C_1$-$C_6$ dialkylamine, $(C_1$-$C_6)$alkyl-pyrrolidine, $(C_1$-$C_6)$alkyl-piperidine, or $(C_1$-$C_6)$alkyl-morpholine;

with the further proviso that where $R^6$ is $(C_1$-$C_4)$alkyl-$CO_2R^9$ or $CO_2R^9$; or $R^7$ is $CO_2R^{10}$; or W', X', or Y' is $CO_2R^8$, then at least one, but no more than two of $R^5$, $R^8$, $R^9$, and $R^{10}$ is other than hydrogen;

or a pharmaceutically acceptable salt thereof.

It is understood that the $iGluR_5$ receptor antagonists of the present invention may exist as pharmaceutically acceptable salts and, as such, salts are therefore included within the scope of the present invention. The term "pharmaceutically acceptable salt" as used herein, refers to salts of the compounds provided by, or employed in the present invention which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

It will be understood by the skilled reader that most or all of the compounds used in the present invention are capable of forming salts, and that the salt forms of pharmaceuticals are commonly used, often because they are more readily crystallized and purified than are the free bases. In all cases, the use of the pharmaceuticals described herein as salts is contemplated in the description herein, and often is preferred, and the pharmaceutically acceptable salts of all of the compounds are included in the names of them.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, hydroiodide, dihydroiodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid, mandelic acid, p-toluenesulfonic acid, and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred. It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that such salts may exist as a hydrate.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of Formula I can be resolved by one of ordinary skill in the art using standard techniques well known in the art, such as those described by J. Jacques, et al., "Enantiomers, Racemates, and Resolutions", John Wiley and Sons, Inc., 1981.

The compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The specific stereoisomers and enantiomers of compounds of Formula I can be prepared by one of ordinary skill in the art utilizing well known techniques and processes, such as those disclosed by Eliel and Wilen, "Stereochemistry of Organic Compounds", John Wiley & Sons, Inc., 1994, Chapter 7, Separation of Stereoisomers. Resolution.

Racemization, and by Collet and Wilen, "Enantiomers, Racemates, and Resolutions", John Wiley & Sons, Inc., 1981. For example, the specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

As used herein the term "Pg" refers to a suitable nitrogen protecting group. Examples of a suitable nitrogen protecting group as used herein refers to those groups intended to protect or block the nitrogen group against undesirable reactions-during synthetic procedures. Choice of the suitable nitrogen protecting group used will depend upon the conditions that will be employed in subsequent reaction steps wherein protection is required, and is well within the knowledge of one of ordinary skill in the art. Commonly used nitrogen protecting groups are disclosed in Greene, "Protective Groups In Organic Synthesis," (John Wiley & Sons, New York (1981)). Suitable nitrogen protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, .alpha.-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, .alpha.,.alpha.-dimethyl-3,5-dimethoxybenzyloxycarbonyl, benzhydryloxycarbonyl, t-butoxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred suitable nitrogen protecting groups are formyl, acetyl, methyoxycarbonyl, benzoyl, pivaloyl, t-butylacetyl, phenylsulfonyl, benzyl, t-butyoxycarbonyl (Boc) and benzyloxycarbonyl (Cbz).

As used herein the term "$(C_1-C_4)$alkyl" refers to a straight or branched, monovalent, saturated aliphatic chain of 1 to 4 carbon atoms and includes, but is not limited to methyl, ethyl, n-propyl, isopropyl, n-butyl, isobutyl and the like.

As used herein the term "$(C_1-C_6)$alkyl" refers to a straight or branched, monovalent, saturated aliphatic chain of 1 to 6 carbon atoms and includes, but is not limited to methyl, ethyl, n-propyl, isopropyl, n-butyl, isobutyl, t-butyl, n-pentyl, n-hexyl, and the like.

As used herein the term "$(C_1-C_{10})$alkyl" refers to a straight or branched, monovalent, saturated aliphatic chain of 1 to 10 carbon atoms and includes, but is not limited to methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like.

As used herein the term "$(C_1-C_{20})$alkyl" refers to a straight or branched, monovalent, saturated aliphatic chain of 1 to 20 carbon atoms and includes, but is not limited to, methyl, ethyl, propyl, isopropyl, butyl, isobutyl, t-butyl, pentyl, isopentyl, hexyl, 3-methylpentyl, 2-ethylbutyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-nonadecyl, n-eicosyl and the like. It is understood that the terms "$(C_1-C_4)$alkyl", "$(C_1-C_6)$alkyl", and "$(C_1-C_{10})$alkyl" are included within the definition of "$(C_1-C_{20})$alkyl".

As used herein, the terms "Me", "Et", "Pr", "iPr", "Bu", "iBu", and "t-Bu" refer to methyl, ethyl, propyl, isopropyl, butyl, isobutyl, and tert-butyl respectively.

As used herein, the term "$(C_1-C_4)$alkoxy" refers to an oxygen atom bearing a straight or branched, monovalent, saturated aliphatic chain of 1 to 4 carbon atoms and includes, but is not limited to methyoxy, ethyoxy, n-propoxy, isopropoxy, n-butoxy, and the like.

As used herein the term "$(C_1-C_6)$alkoxy" refers to an oxygen atom bearing a straight or branched, monovalent, saturated aliphatic chain of 1 to 6 carbon atoms and includes, but is not limited to methoxy, ethoxy, n-propoxy, isopropoxy, n-butoxy, n-pentoxy, n-hexoxy, and the like.

As used herein, the term "$(C_1-C_6)$alkyl$(C_1-C_6)$alkoxy" refers to a straight or branched, monovalent, saturated aliphatic chain of 1 to 6 carbon atoms which has a $(C_1-C_6)$ alkoxy group attached to the aliphatic chain.

As used herein, the terms "Halo", "Halide" or "Hal" refer to a chlorine, bromine, iodine or fluorine atom, unless otherwise specified herein.

As used herein the term "$(C_2-C_6)$alkenyl" refers to a straight or branched, monovalent, unsaturated aliphatic chain having from two to six carbon atoms. Typical $C_2-C_6$ alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

As used herein, the term "aryl" refers to a monovalent carbocyclic group containing one or more fused or non-fused phenyl rings and includes, for example, phenyl, 1- or 2-naphthyl, 1,2-dihydronaphthyl, 1,2,3,4-tetrahydronaphthyl, and the like. The term "substituted aryl" refers to an aryl group substituted with one or two moieties chosen from the group consisting of halogen, hydroxy, cyano, nitro, $(C_1-C_6)$alkyl, $(C_1-C_6)$alkoxy, $(C_1-C_6)$alkyl$(C_3-C_{10})$cycloalkyl, $(C_1-C_6)$alkylaryl, $(C_1-C_6)$alkoxycarbonyl, protected carboxy, carboxymethyl, hydroxymethyl, amino, aminomethyl, trifluoromethyl, or trifluoromethoxy.

As used herein, the term "$(C_1-C_6)$alkylaryl" refers to a straight or branched, monovalent, saturated aliphatic chain of 1 to 6 carbon atoms which has an aryl group attached to the aliphatic chain. Included within the term "$C_1-C_6$ alkylaryl" are the following:

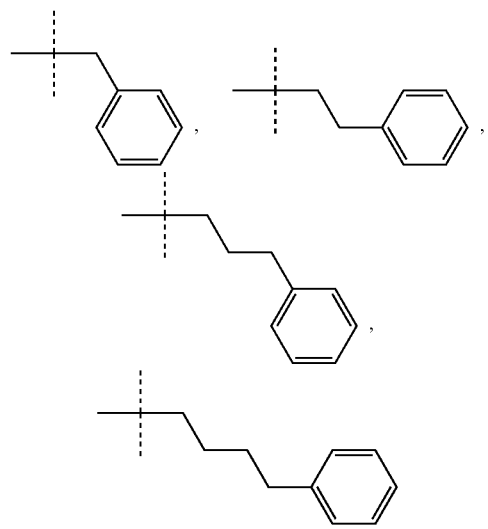

and the like.

As used herein, the term "($C_1$-$C_4$)alky(substituted)laryl" refers to a straight or branched, monovalent, saturated aliphatic chain of 1 to 6 carbon atoms which has a "substituted ary" group attached to the aliphatic chain As used herein, the term "aryl($C_1$-$C_6$)alkyl" refers to an aryl group which has a straight or branched, monovalent, saturated aliphatic chain of 1 to 6 carbon atoms attached to the aryl group. Included within the term "aryl($C_1$-$C_6$)alkyl" are the following:

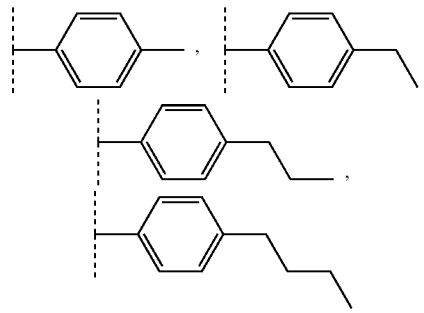

and the like.

As used herein the term "($C_3$-$C_{10}$)cycloalkyl" refers to a saturated hydrocarbon ring structure composed of one or more fused or unfused rings containing from three to ten carbon atoms. Typical $C_3$-$C_{10}$ cycloalkyl groups include cyclopropyl, cyclobutyl, cyclopentyl, cyclohexyl, cycloheptyl, cyclooctyl, adamantanyl, and the like.

As used herein, the term "$C_1$-$C_6$ alkyl($C_3$-$C_{10}$)cycloalkyl" refers to a straight or branched, monovalent, saturated aliphatic chain of 1 to 6 carbon atoms which has a ($C_3$-$C_{10}$) cycloalkyl attached to the aliphatic chain. Included within the term "$C_1$-$C_6$ alkyl($C_3$-$C_{10}$)cycloalkyl" are the following:

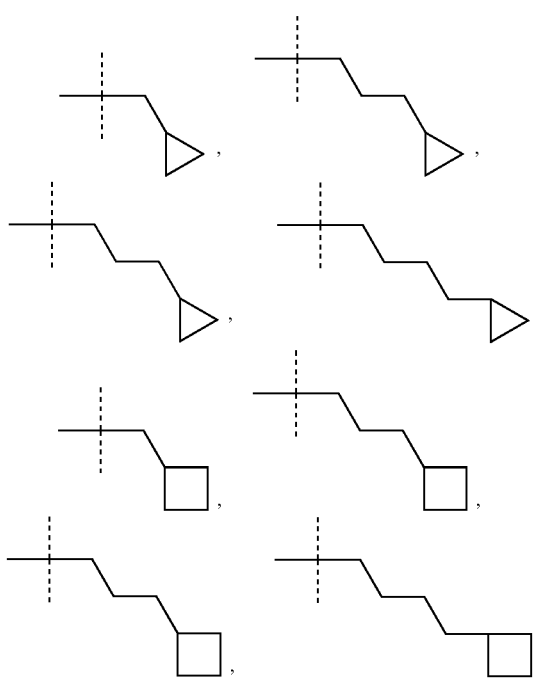

-continued

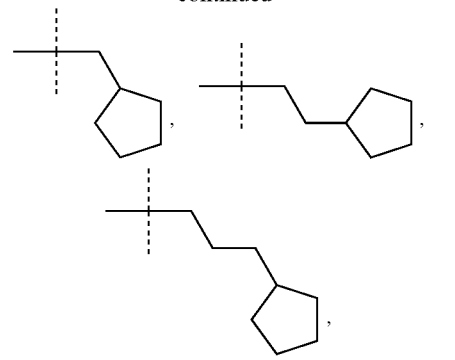

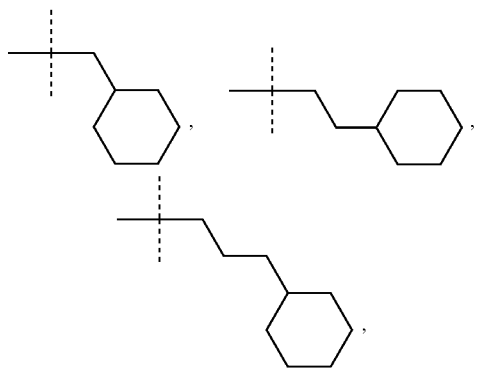

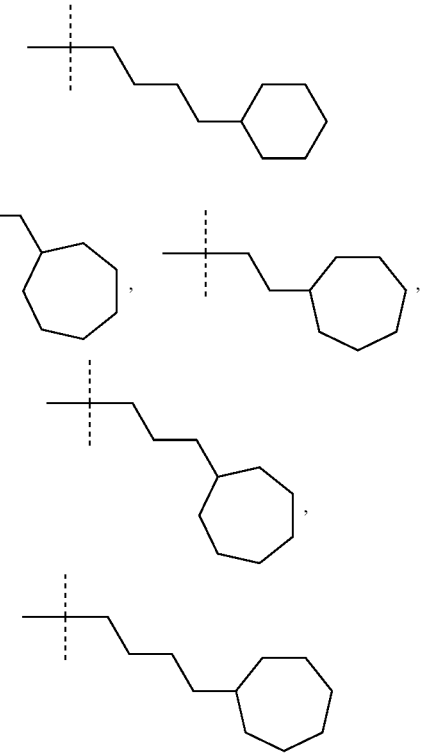

and the like.

As used herein, the term "($C_1$-$C_6$) alkoxycarbonyl" refers to a carbonyl group having a ($C_1$-$C_6$)alkyl group attached to the carbonyl carbon through an oxygen atom. Examples of this group include t-butoxycarbonyl, methoxycarbonyl, and the like.

As used herein the term "heterocycle" refers to a five- or six-membered ring, which contains one to four heteroatoms selected from the group consisting of oxygen, sulfur, and nitrogen. The remaining atoms of the ring are recognized as carbon by those of skill in the art. Rings may be saturated or unsaturated. Examples of heterocycle groups include thiophenyl, furyl, pyrrolyl, imidazolyl, pyrrazolyl, thiazolyl, thiazolidinyl, isothiazolyl, oxazolyl, isoxazolyl, triazolyl, thiadiazolyl, oxadiazolyl, tetrazolyl, pyridyl, pyrimidyl, pyrazinyl, pyridiazinyl, triazinyl, imidazolyl, dihydropyrimidyl, tetrahydropyrimdyl, pyrrolidinyl, piperidinyl, piperazinyl, pyrazolidinyl, pyrimidinyl, imidazolidimyl, morpholinyl, pyranyl, thiomorpholinyl, and the like. The term "substituted heterocycle" represents a heterocycle group substituted with one or two moieties chosen from the group consisting of halogen, hydroxy, cyano, nitro, oxo, ($C_1$-$C_6$) alkyl, ($C_1$-$C_4$)alkoxy, $C_1$-$C_6$ alkyl($C_3$-$C_{10}$)cycloalkyl, ($C_1$-$C_6$)alkylaryl, ($C_1$-$C_6$)alkoxycarbonyl, protected carboxy, carboxymethyl, hydroxymethyl, amino, aminomethyl, trifluoromethyl, or trifluoromethoxy. Further, the heterocycle group can be optionally fused to one or two aryl groups to form a benzo-fused group. Examples of substituted heterocycle include 1,2,3,4-tetrahydrodibenzeofuranyl, 2-methylbezylfuranyl, and 3,5 dimethylisoxazolyl, and the like.

As used herein, the term "benzo-fused group" refers to a phenyl group fused to an aromatic radical or a heterocycle group. Included within the term "benzo-fused group" are the following:

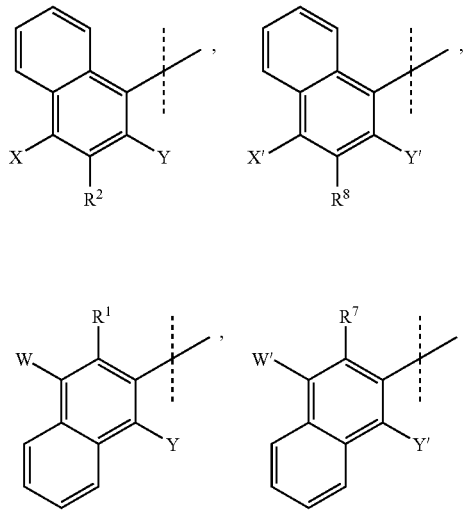

and the like, wherein all substituents are as previously defined hereinabove.

As used herein, the term "triazole-fused group" refers to a triazole group fused to an aromatic radical or a heterocycle group. Included within the term "triazole-fused group" are the following:

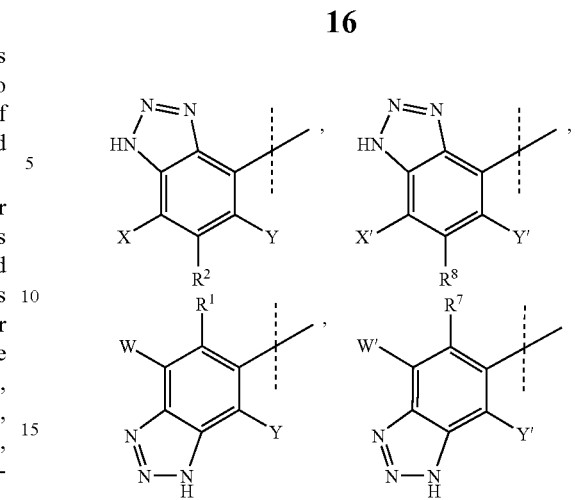

and the like, wherein all substituents are as previously defined.

As used herein the term "N,N—$C_1$-$C_6$ dialkylamine" refers to a nitrogen atom substituted with two straight or branched, monovalent, saturated aliphatic chains of 1 to 6 carbon atoms. Included within the term "N,N—$C_1$-$C_6$ dialkylamine" are —N($CH_3$)$_2$, —N($CH_2CH_3$)$_2$, —N($CH_2CH_2CH_3$)$_2$, —N($CH_2CH_2CH_2CH_3$)$_2$, and the like.

As used herein the term "$C_1$-$C_6$alkyl-N,N—$C_1$-$C_6$dialkylamine" refers to straight or branched, monovalent, saturated aliphatic chain of 1 to 6 carbon atoms which has an N,N—$C_1$-$C_6$ dialkylamine attached to the aliphatic chain. Included within the term "$C_1$-$C_6$ alkyl-N,N—$C_1$-$C_6$ dialkylamine" are the following:

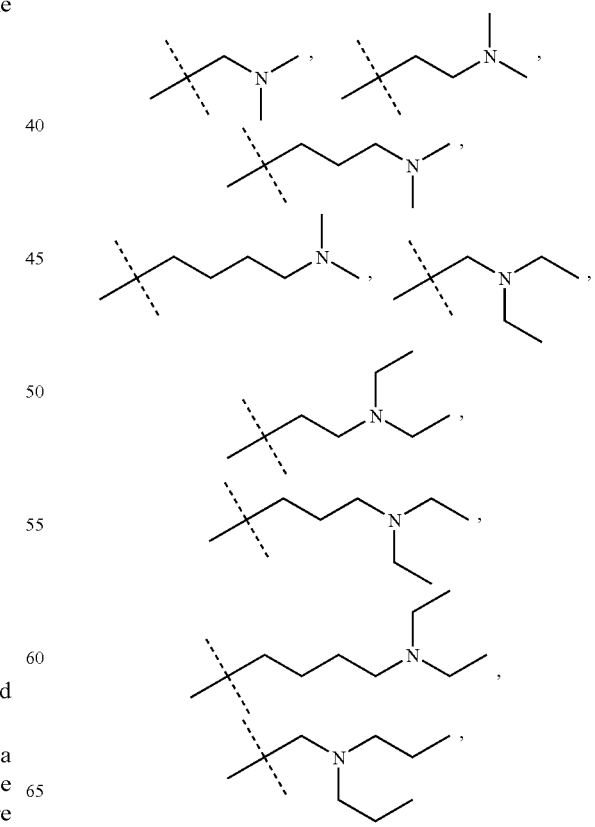

-continued

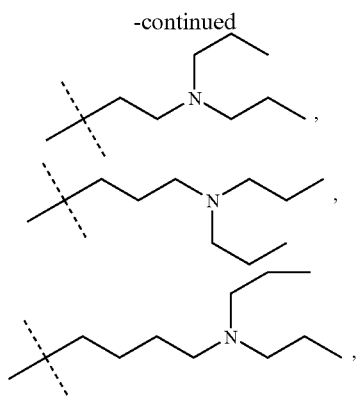

and the like.

As used herein the term "$(C_1-C_6)$alkyl-pyrrolidine" refers to a straight or branched, monovalent, saturated aliphatic chain of 1 to 6 carbon atoms which has a pyrrolidine attached to the aliphatic chain. Included within the scope of the term "$(C_1-C_6)$alkyl-pyrrolidine" are the following:

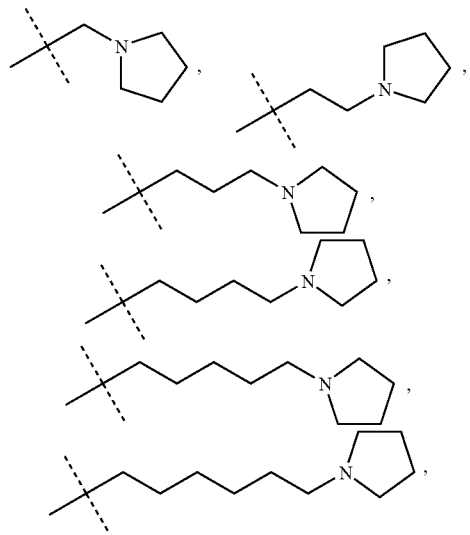

and the like.

As used herein the term "$(C_1-C_6)$alkyl-piperidine" refers to a straight or branched, monovalent, saturated aliphatic chain of 1 to 6 carbon atoms which has a piperidine attached to the aliphatic chain. Included within the scope of the term "$(C_1-C_6)$alkyl-piperidine" are the following:

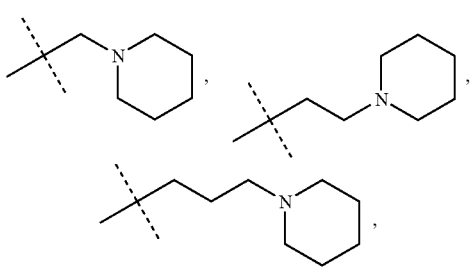

-continued

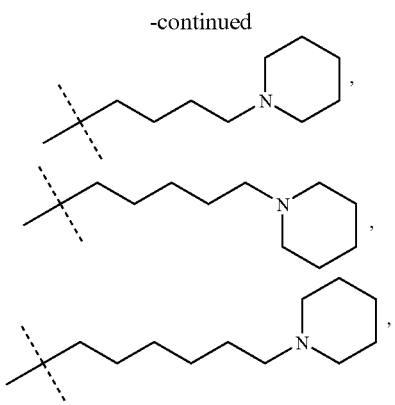

and the like.

As used herein the term "$(C_1-C_6)$alkyl-morpholine" refers to a straight or branched, monovalent, saturated aliphatic chain of 1 to 6 carbon atoms which has a morpholine attached to the aliphatic chain. Included within the scope of the term "$C_1-C_6$ alkyl-morpholine" are the following:

and the like.

The designation "◂▬◾" refers to a bond that protrudes forward out of the plane of the page:

The designation "▪▪▪▪▪" refers to a bond that protrudes backward out of the plane of the page.

As used herein the term "iGluR$_5$" refers to the kainate ionotropic glutamate receptor, subtype 5, of the larger class of excitatory amino acid receptors.

As used herein the term "migraine" refers a disorder of the nervous system characterized by recurrent attacks of head pain (which are not caused by a structural brain abnormalitiy such as those resulting from tumor or stroke), gasrointestinal disturbances, and possibly neurological symptoms such as visual distortion. Characteristic headaches of migraine usually last one day and are commonly accompanied by nausea, emesis, and photophobia.

Migraine may represent a "chronic" condition, or an "acute" episode. The term "chronic", as used herein, means a condition of slow progress and long continuance. As such, a chronic condition is treated when it is diagnosed and treatment continued throughout the course of the disease. Conversely, the term "acute" means an exacerbated event or attack, of short course, followed by a period of remission. Thus, the treatment of migraine contemplates both acute events and chronic conditions. In an acute event, compound is administered at the onset of symptoms and discontinued when the symptoms disappear. As described above, a chronic condition is treated throughout the course of the disease.

As used herein the term "patient" refers to a mammal, such a mouse, gerbil, guinea pig, rat, dog or human. It is understood, however, that the preferred patient is a human.

The term "iGluR$_5$ receptor antagonist" or "iGluR$_5$ antagonist", as used herein, refers to those excitatory amino acid receptor antagonists which bind to, and antagonize the activity of, the iGluR$_5$ kainate receptor subtype. As a preferred embodiment, the present invention further provides selective iGluR$_5$ receptor antagonists. "Selective iGluR$_5$ receptor antagonist" or "selective iGluR$_5$ antagonist" as used herein, includes those excitatory amino acid receptor antagonists which selectively bind to, and antagonize, the iGluR$_5$ kainate receptor subtype, relative to the iGluR$_2$ AMPA receptor subtype. Preferably, the "selective iGluR$_5$ antagonists" for use according to the methods of the present invention have a binding affinity at least 10 fold greater for iGluR$_5$ than for iGluR$_2$, more preferably at least 100 fold greater. WO 98/45270 provides examples of selective iGluR$_5$ receptor antagonists and discloses methods for synthesis.

As used herein, the terms "treating", "treatment", or "to treat" each mean to alleviate symptoms, eliminate the causation of resultant symptoms either on a temporary or permanent basis, and to prevent, slow the appearance, or reverse the progression or severity of resultant symptoms of the named disorder. As such, the methods of this invention encompass both therapeutic and prophylactic administration.

As used herein the term "effective amount" refers to the amount or dose of the compound, upon single or multiple dose administration to the patient, which provides the desired effect in the patient under diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the degree of involvement or the severity of the disease involved; the response of the individual patient; the particular compound administered; the mode of administration; the bioavailability characteristics of the preparation administered; the dose regimen selected; the use of concomitant medication; and other relevant circumstances.

A typical daily dose will contain from about 0.01 mg/kg to about 100 mg/kg of each compound used in the present method of treatment. Preferably, daily doses will be about 0.05 mg/kg to about 50 mg/kg, more preferably from about 0.1 mg/kg to about 25 mg/kg.

Oral administration is a preferred route of administering the compounds employed in the present invention whether administered alone, or as a combination of compounds capable of acting as an iGluR$_5$ receptor antagonist. Oral administration, however, is not the only route, nor even the only preferred route. Other preferred routes of administration include transdermal, percutaneous, pulmonary, intravenous, intramuscular, intranasal, buccal, or intrarectal routes. Where the iGluR$_5$ receptor antagonist is administered as a combination of compounds, one of the compounds may be administered by one route, such as oral, and the other may be administered by the transdermal, percutaneous, pulmonary, intravenous, intramuscular, intranasal, buccal, or intrarectal route, as particular circumstances require. The route of administration may be varied in any way, limited by the physical properties of the compounds and the convenience of the patient and the caregiver.

The compounds employed in the present invention may be administered as pharmaceutical compositions and, therefore, pharmaceutical compositions incorporating compounds of Formula I are important embodiments of the present invention. Such compositions may take any physical form that is pharmaceutically acceptable, but orally administered pharmaceutical compositions are particularly preferred. Such pharmaceutical compositions contain, as an active ingredient, an effective amount of a compound of Formula I, including the pharmaceutically acceptable salts, prodrugs, and hydrates thereof, which effective amount is related to the daily dose of the compound to be administered. Each dosage unit may contain the daily dose of a given compound, or may contain a fraction of the daily dose, such as one-half or one-third of the dose. The amount of each compound to be contained in each dosage unit depends on the identity of the particular compound chosen for the therapy, and other factors such as the indication for which it is given. The pharmaceutical compositions of the present invention may be formulated so as to provide quick, sustained, or delayed release of the active ingredient after administration to the patient by employing well known procedures.

Compositions are preferably formulated in a unit dosage form, each dosage containing from about 1 to about 500 mg of each compound individually or in a single unit dosage form, more preferably about 5 to about 300 mg (for example 25 mg). The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compound, however, is best defined as the "effective amount", that is, the amount of each compound which provides the desired dose to the patient in need of such treatment.

The activity of the compounds employed in the present invention do not depend on the nature of the composition, hence, the compositions are chosen and formulated solely for convenience and economy.

Capsules are prepared by mixing the compound with a suitable diluent and filling the proper amount of the mixture in capsules. The usual diluents include inert powdered substances such as starches, powdered cellulose especially crystalline and microcrystalline cellulose, sugars such as fructose, mannitol and sucrose, grain flours, and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

Tablets are often coated with sugar as a flavor and sealant. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

A lubricant is often necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate.

When it is desired to administer the compound as a suppository, the usual bases may be used. Cocoa butter iso a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with innumerable pores through which the drugs are pumped by osmotic action.

The following table provides an illustrative list of formulations suitable for use with the compounds employed in the present invention. The following is provided only to illustrate the invention and should not be interpreted as limiting the present invention in any way.

Formulation 1
Hard gelatin capsules are prepared using the following ingredients:

| | Quantity (mg/capsule) |
|---|---|
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2
A tablet is prepared using the ingredients below:

| | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3
An aerosol solution is prepared containing the following components:

| | Weight % |
|---|---|
| Active Ingredient | 0.25 |
| Ethanol | 29.75 |
| Propellant 22 (Chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4
Tablets each containing 60 mg of active ingredient are made as follows:

| | |
|---|---|
| Active Ingredient | 60.0 mg |
| Starch | 45.0 mg |
| Microcrystalline cellulose | 35.0 mg |
| Polyvinylpyrrolidone | 4.0 mg |
| Sodium carboxymethyl starch | 4.5 mg |
| Magnesium stearate | 0.5 mg |
| Talc | 1.0 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

| Formulation 5 Capsules each containing 80 mg medicament are made as follows: | |
|---|---|
| Active Ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

| Formulation 6 Suppositories each containing 225 mg of active ingredient may be made as follows: | |
|---|---|
| Active Ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

| Formulation 7 Suspensions each containing 50 mg of medicament per 5 ml dose are made as follows: | |
|---|---|
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

| Formulation 8 An intravenous formulation may be prepared as follows: | |
|---|---|
| Active Ingredient | 100 mg |
| Mannitol | 100 mg |
| 5 N Sodium hydroxide | 200 ml |
| Purified water to total | 5 ml |

It is understood by one of ordinary skill in the art that the procedures as described above can also be readily applied to a method of treating neurological disorders or neurodegenerative conditions, particularly pain and migraine, comprising administering to a patient an effective amount of a compound of Formula I.

Compounds of Formula I and Formula I(a) can be chemically prepared, for example, by following the synthetic routes set forth in the Schemes below. However, the following discussion is not intended to be limiting to the scope of the present invention in any way. For example, the specific synthetic steps for the routes described herein may be combined in different ways, or with steps from different schemes, to prepare the compounds of Formula I and Formula I(a). All substituents, unless otherwise indicated, are as previously defined. The reagents and starting materials are readily available to one of ordinary skill in the art. For example, certain starting materials can be prepared by one of ordinary skill in the art following procedures disclosed in U.S. Pat. No. 5,356,902 (issued Oct. 18, 1994) and U.S. Pat. No. 5,446,051 (issued Aug. 29, 1995) and U.S. Pat. No. 5,670,516 (issued Sep. 23, 1997) the entire contents, all of which, are herein incorporated by reference. Other necessary reagents and starting materials for the below procedures may be made by procedures which are selected from standard techniques of organic and heterocyclic chemistry, techniques which are analogous to the syntheses of known structurally similar compounds, and the procedures described in the Examples, including novel procedures.

Compounds of Formula I, wherein Z represents an oxygen atom, may be synthesized according to Scheme I.

Scheme I
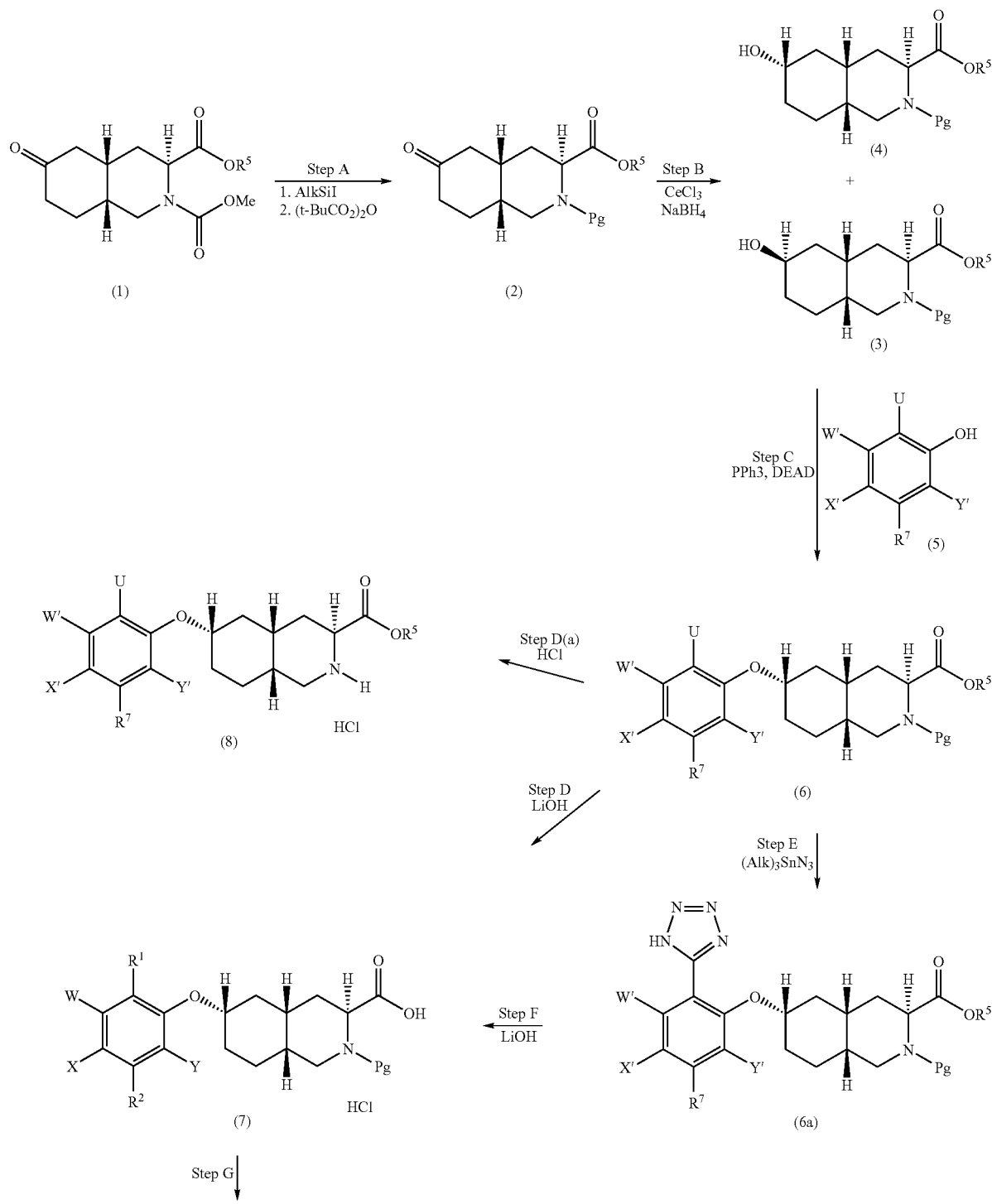

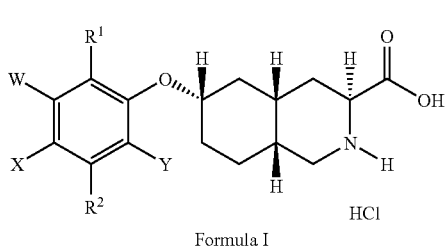

Formula I

Step H →

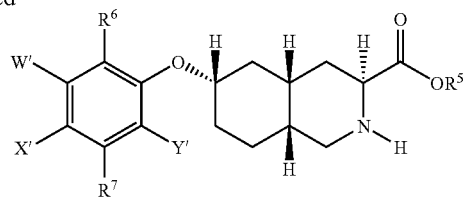

Formula Ia

In Scheme I, step A, the compound of structure (1) is treated with a trialkylsilyl iodide ($Alk_3SiI$) and the resulting amine, without isolation, is protected under standard conditions to provide the compound of structure (2). For example, when a protecting group other than methoxycarbonyl is desired, a solution of ethyl-6-oxo-2-methoxycarbonyl-decahydroisoquinolie-3-carboxylate, dissolved in a suitable organic solvent such as dichloromethane at room temperature, is treated with about 4 equivalents of a compound of formula $Alk_3SiI$ such as trimethylsilyl iodide, triethylsilyl iodide, tributylsilyl iodide, and the like, with trimethylsilyl iodide being most preferred. The reaction mixture is stirred for about 10 to 20 hours, quenched with ethanol and concentrated under vacuum. The resulting solid, for example, is then dissolved in a suitable organic solvent such as dichloromethane and treated with an excess of a suitable organic base, such as triethylamine, followed by about 1 equivalent of, for example, di-tert-butyl dicarbonate. The reaction mixture is stirred at room temperature for 10 to 20 hours. The compound (2) is then isolated using standard procedures. For example, the reaction mixture is concentrated under vacuum, suspended in ethyl acetate and filtered. The filtrate is washed with diluted hydrochloric acid and water, the organic layer separated and dried over anhydrous sodium sulfate, filtered, and concentrated under vacuum to provide concentrated compound (2). Column chromatography may then be performed on silica gel with a suitable eluent such as 25% ethyl acetate/hexane to provide the purified compound (2). Note, where the desired protecting group (Pg) is methoxycarbonyl, the compound of structure (1) may be used directly in Step B below.

In Scheme I, Step B, compound (2) is reduced under standard conditions with a suitable reducing reagent in the presence of a suitable Lewis acid catalyst, to provide the compound of structure (3). For example, ethyl 6-oxo-2-tert-butoxycarbonyl-decahydroisoquinoline-3-carboxylate (compound (2) of Step A above) is mixed with about 1 equivalent of a Lewis acid catalyst, such as cerium trichloride, in a suitable organic solvent such as ethanol. The resulting solution is cooled to −78° C. and about 1 to 2 equivalents of a reducing reagent, such as sodium borohydride, is added and the mixture is warmed slowly to room temperature. After 4 to 8 hours, a suitable acid, such as acetic acid, is added at 0° C. and the resulting mixture is stirred for about 1 to 2 hours at room temperature and concentrated under vacuum. The compound (3) is then isolated using standard procedures such as extraction techniques. For example, the reaction mixture is partitioned between water and an organic solvent such as ethyl acetate, and the aqueous layer is extracted 2-4 times with ethyl acetate. The organic layers are combined, dried over anhydrous sodium sulfate, filtered, and concentrated under vacuum to provide a mixture of compound (3) and compound (4). Both compounds are then purified by chromatography on silica gel with a suitable eluent such as 70% ethyl acetate/hexanes.

In Scheme I, Step C, compound (4) is treated with a compound of structure (5) in the presence of a phosphine and a dialkyl azadicarboxylate to give the compound of structure (6). For example, a solution of ethyl-6-hydroxy-2-tert-butoxycarbonyl-decahydroisoquinoline-3-carboxylate, about 1-1.5 equivalents of compound of structure (5) (wherein U represents hydrogen, CN, $(C_1-C_4)$alkyl-$CO_2R^9$, or $CO_2R^9$) about 0-1.5 equivalents of an organic base such as pyridine, and about 1-1.5 equivalents of a phosphine such as triphenylphosphine in tetrahydrofuran is treated with about 1-1.5 equivalents of a dialkyl azadicarboxylate such as diethyl azodicarboxylate. The reaction is then stirred at 25-70° C. for 15-48 hours. The solvents are removed under vacuum to provide the compound of structure (6). Compound (6) is then purified by chromatography on silica gel with a suitable eluent such as diethyl ether/hexanes or ethyl acetate/hexanes.

In Scheme I, Step D(a), the compound of structure (6) is deprotected under standard conditions well known in the art to provide the compound of structure (8). For example, compound (6) is treated with an organic solvent such as ethyl acetate saturated with HCl at room temperature for about 3 to 5 hours. The mixture is then concentrated under vacuum to provide the compound of structure (8) wherein U is as defined in Step C. This material may then be purified by techniques well known in the art, such as titration with organic solvents and/or cation exchange chromatography, eluting with MeOH/water, followed by 2N ammonia in MeOH, to provide the purified compound of structure (8) wherein U is as defined in Step C.

In Scheme I, Step D, the compound of structure (6) is hydrolyzed under standard conditions to give the compound of structure (7) wherein $R^1$ is other than tetrazole, but otherwise as defined hereinabove. For example, compound (6) is dissolved in a suitable organic solvent or solvents mixture, such as methanol, ethanol, tetrahydrofuran and/or ethyl acetate, and treated with an excess of a suitable base. Examples of suitable bases include aqueous lithium hydroxide, sodium hydroxide, potassium hydroxide, and the like, with lithium hydroxide being preferred. The reaction is stirred for about 10-36 hours. The reaction mixture is then concentrated under vacuum, diluted with water and washed with ethyl acetate. The aqueous layer is made acidic to pH 3-4 with 10% HCl and extracted with ethyl acetate. These organic phases are combined, dried over sodium sulfate, filtered, and concentrated under vacuum to provide the compound (7) wherein $R^1$ is other than tetrazole, but otherwise as defined hereinabove. The material may then be purified by chromatography on silica gel with a suitable eluent such as ethyl acetate/hexanes/acetic acid, to provide the purified compound.

In Scheme I, where it is desired that the compound of structure (7) contain a tetrazole at $R^1$, compound (6) (wherein U for the purposes of this step is nitrile) is treated with a compound of $Alk_3SnN_3$ in Step E to give the compound of structure (6a). This is followed by hydroysis in Step F, to provide the compound of structure (7) (wherein $R^1$ is tetrazole). For example, compound (6) (wherein U is nitrile) is treated with about 3 to 5 equivalents of azido-tri-n-butyl stannane at about 70 to 100° C. for about 12 to 16 hours under an atmosphere of nitrogen to give the compound of structure (6a). Compound (6a) is then hydrolyzed, concentrated, and the resulting compound (7) (wherein $R^1$ is tetrazole) may then be purified, all of which occur under standard conditions well known in the art as described in Step D above.

As an alternative to Steps D and F above, the compounds of structure (6) and (6a) may be selectivley hydrolyzed under standard conditions known in the art to provide a compound of structure (7a):

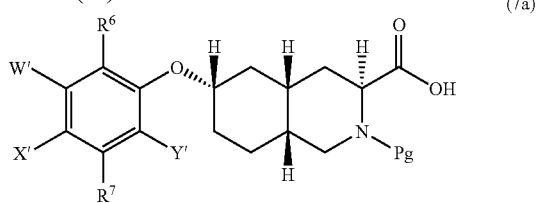

(7a)

For example, compound (6) may be hydrolyzed to provide compounds of (7a) wherein $R^6$ is as defined hereinabove, other than tetrazole, whereas compound (6a) may be hydrolyzed to provide compounds of (7a) wherein $R^6$ is tetrazole.

Methods for the selective hydrolysis of compounds of structure (6) and (6a) are well known in the art.

In Scheme I, Step G, the compound of structure (7) is deprotected under standard conditions well known in the art to provide the compound of Formula I. For example, compound (7) is treated with an organic solvent, such as ethyl acetate, saturated with hydrogen chloride at room temperature for about 3 to 5 hours. The mixture is then concentrated under vacuum to provide the compounds of Formula I. This material may then be purified by techniques well known in the art, such as tritration with organic solvents and/or cation exchange chromatography eluting with methanol/water, followed by 2 N ammonia in methanol, to provide the purified compound of Formula I.

As an alternative to the sequence of Steps D and G, and as an alternative to the sequence of steps F and G, the compounds of structure (6) and (6a), respectively, may be concomitantly hydrolyzed and deprotected as provided below to provide the compounds of Formula I.

Scheme II

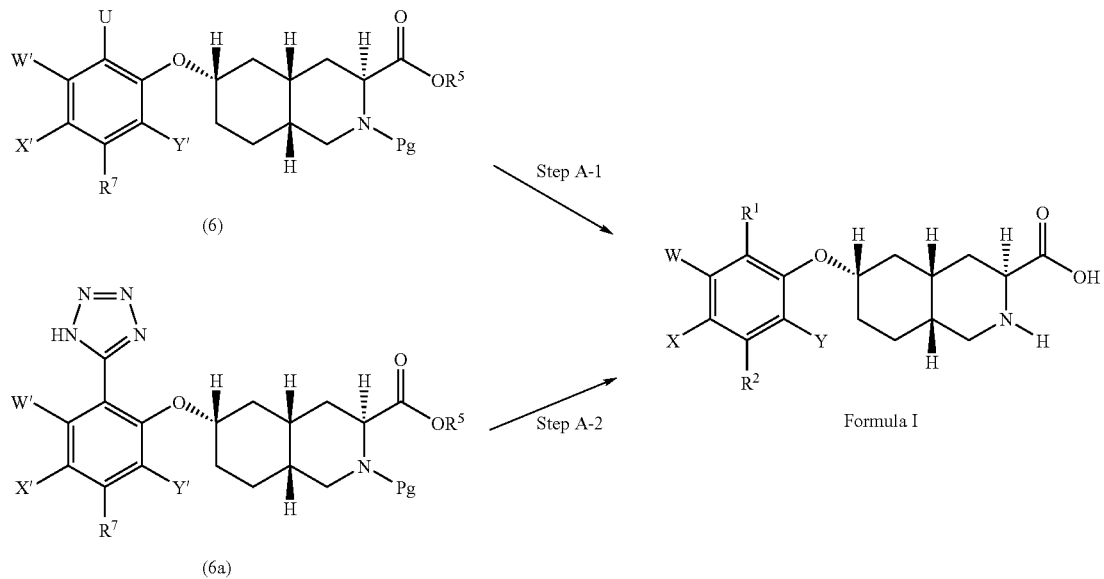

Compound (7a) can then be deprotected under standard conditions to provide the compound of structure (9):

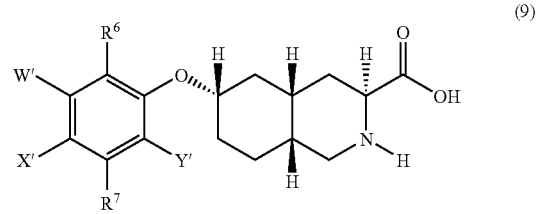

(9)

In Scheme II, compound (6) or (6a) is deprotected and hydrolyzed concomitantly under standard conditions to provide the compounds of Formula I. For example, in Scheme II, Step A-1, a solution of compound (6), dissolved in 6N HCl, is heated to reflux (90-950° C.) for about 15-20 hours. The reaction mixture is then allowed to cool to room temperature and concentrated in vacuo to provide the compound of Formula I wherein $R^1$ is as defined hereinabove, other than tetrazole. The compound of Formula I can then be purified by techniques well known in the art, such as cation exchange chromatography eluting with methanol/water followed by 2N ammonia in methanol or ethanol to provide the purified compound of Formula I wherein R¹ is as defined other than tetrazole. In Scheme II Step A-2, a solution of compound (6a) is treated as described above in Step A-1 to provide the compound of Formula I wherein R¹ is tetrazole. This material may then be purified by techniques well known in the art, such as cation exchange chromatography eluting with methanol/water followed by 2N ammonia in methanol or ethanol to provide the purified compound of Formula I wherein R¹ is tetrazole.

In Scheme I, Step H, the compound of Formula I may be nonselectively or selectively esterified to provide the compounds of Formula Ia. For example, the compound of Formula I is dissolved in a suitable organic solvent, such as ethanol, isobutanol, or 2-ethylbutanol, and treated with an excess of a dehydrating agent such as thionyl chloride. The reaction mixture is heated to about 120° C. for about 1 to 2 hours. The reaction mixture is then concentrated under vacuum to provide the crude compound of Formula Ia. This material may then be precipitated with diethyl ether and filtered to provide the purified compound. Alternatively in Step H, the compound of Formula I can be esterified by dissolving in a suitable organic solvent such as ethanol, and treating with an excess of a suitable acid. Examples of suitable acids include gaseous hydrochloric acid, aqueous sulfuric acid, p-toluene sulfonic acid, and the like with gaseous hydrochloric acid being preferred. The reaction mixture is heated to reflux (78-85° C.) for about 15-25 hours. The reaction mixture is then concentrated under vacuum to provide the crude compound of Formula Ia. This material can then be purified by techniques well known in the art, such as cation exchange chromatography eluting with methanol/water followed by 2N ammonia in ethanol to provide the purified compound.

Compounds of Formula I, wherein Z represents an oxygen atom and R¹ represents tetrazole may alternatively be synthesized according to the procedures set forth in Scheme III.

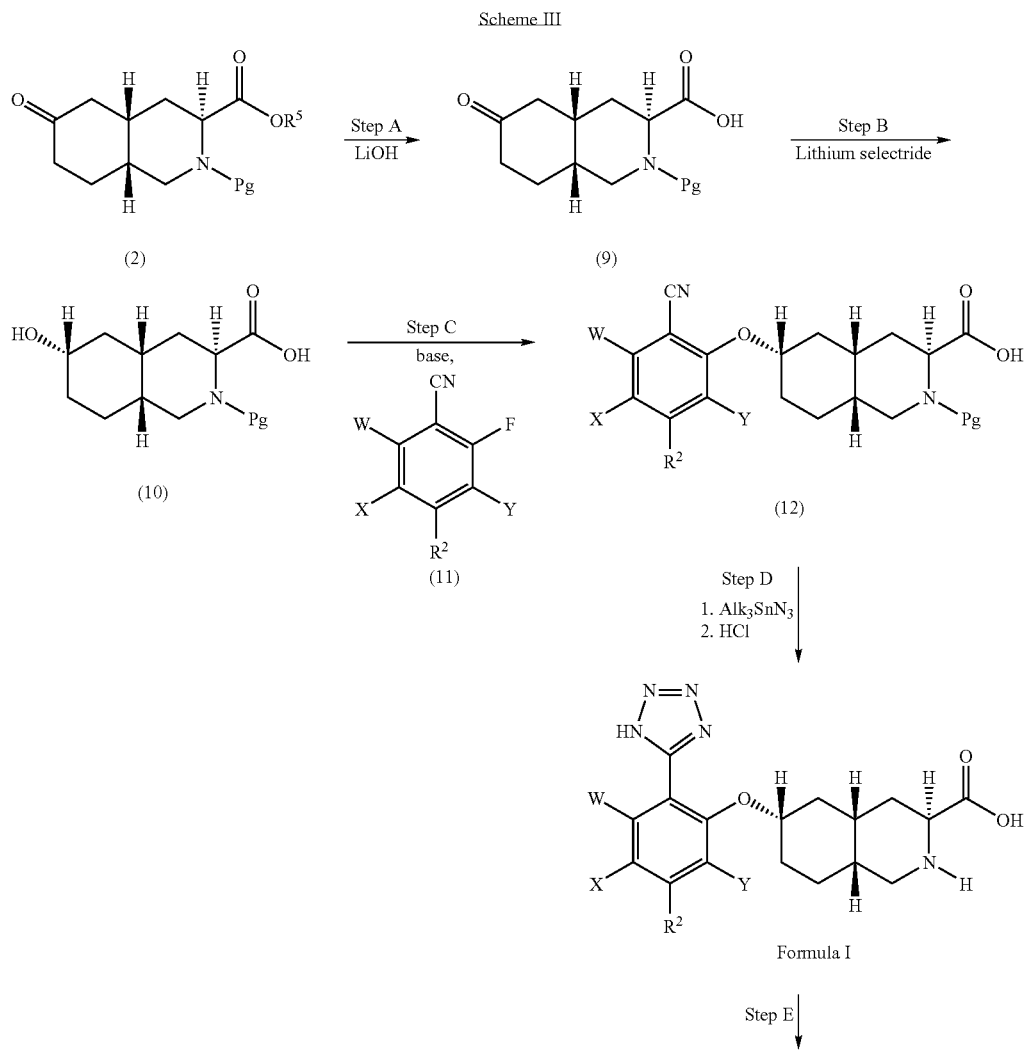

-continued

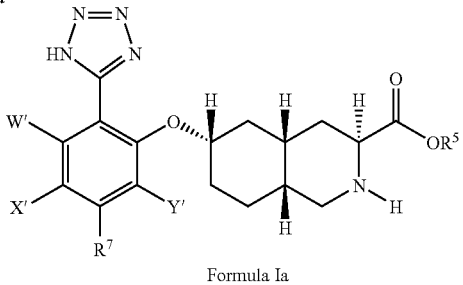

Formula Ia

In Scheme III, step A, the compound of structure (2) (as previously described in Scheme I above), is hydrolyzed to the compound of structure (9) under standard conditions well known in the art. For example, ethyl 6-oxo-2-(tert-butoxycarbonyl)-decahydroisoquinoline-3-carboxylate is dissolved in a suitable organic solvent or solvents mixture, such as methanol, ethanol, tetrahydrofuran and/or ethyl acetate, and treated with an excess of a suitable base. Examples of suitable bases include aqueous lithium hydroxide, sodium hydroxide, potassium hydroxide, and the like with lithium hydroxide being preferred. The reaction is stirred for about 20-24 hours at room temperature. The reaction mixture is then concentrated under vacuum, diluted with water and washed with ethyl acetate. The aqueous layer is made acidic to pH 3-4 with 10% HCl and extracted with ethyl acetate. These organic phases are combined, dried over sodium sulfate, filtered, and concentrated under vacuum to provide the compound of structure (9).

In Scheme III, Step B, compound (9) is reduced with a suitable reducing reagent, such as lithium or sodium selectride, to provide the compound of structure (10). For example, 6-oxo-2-tert-butoxycarbonyl-decahydroisoquinoline-3-carboxylic acid is dissolved in a suitable organic solvent such as tetrahydrofuran. The resulting solution is cooled to about 0° C. and about 2 equivalents of lithium selectride, dissolved in tetrahydrofuran, is added. The reaction mixture is warmed slowly to room temperature. After about 2 to 3 hours, a suitable acid, such as 1N hydrochloric acid, and sodium chloride are added and the resulting mixture is filtered. The compound (10) is then isolated using standard procedures such as extraction techniques. For example, the aqueous layer is extracted 2-4 times with ethyl acetate. The organic layers are combined, dried over anhydrous sodium sulfate, filtered, and concentrated under vacuum to provide the crude compound (10). Compound (10) may then be purified by chromatography on silica gel with a suitable eluent such as 60% ethyl acetate/hexanes.

In Scheme III, Step C, compound (10) is treated with a compound of structure (11) in the presence of a suitable base to provide the compound of structure (12). For example, a solution of 6-hydroxy-2-tert-butoxycarbonyl-decahydroisoquinoline-3-carboxylic acid, dissolved in an organic solvent such as tetrahydrofuran, is treated at 0° C. with about 2-2.5 equivalents of a suitable base such as potassium tert-butoxide. The resulting mixture is stirred at room temperature for about 20 to 40 minutes, cooled to 0° C. and treated with about 1-1.5 equivalents of compound (11) (where $R^2$, W, X, and Y are as defined hereinabove). The reaction is then stirred at room temperature for about 15-24 hours. The reaction mixture is then diluted with water and washed with ethyl acetate. The aqueous layer is made acidic to pH 3-4 with 10% HCl and extracted with ethyl acetate. These organic phases are combined, dried over sodium sulfate, filtered, and concentrated under vacuum to provide the compound of structure (12). Compound (12) may then be purified by chromatography on silica gel with a suitable eluent such as ethyl acetate/hexanes In Scheme II, Step p, compound (12) is treated with a compound of formula $Alk_3SnN_3$, wherein Alk is an alkyl group such as Me, Et, Bu, and the like, and the resulting compound is deprotected without further treatment to the compound of Formula I, wherein $R^1$ is tetrazole, under standard conditions well known in the art. For example, compound (12) is treated with about 3 to 5 equivalents of azido tri-n-butyl stannane at 70 to 100° C. for about 12 to 76 hours under an atmosphere of nitrogen. The mixture is then treated with an organic solvent, such as ethyl acetate, saturated with hydrogen chloride at room temperature for about 3 to 5 hours. The mixture is then concentrated under vacuum to provide the compound of Formula I, wherein $R^1$ is tetrazole. This material may then be purified by techniques well known in the art, such as trituration with organic solvents and/or cation exchange chromatography eluting with methanol/water followed by 2 N ammonia in methanol to provide the purified compound.

In Scheme III, Step E, the compound of Formula I is nonselectively, or selectively, esterified to provide the compound of Formula Ia, wherein $R^6$ is tetrazole. For example, the compound of Formula I is dissolved in a suitable base, such as ethanol, isobutanol, or 2-ethylbutanol, and treated with an excess of a dehydrating agent, such as thionyl chloride. The reaction mixture is heated to 120° C. for about 1-2 hours. The reaction mixture is then concentrated under vacuum to provide the crude compound of Formula Ia, wherein $R^7$ is tetrazole. This material is precipitated with diethyl ether and filtered to provide the purified compound of Formula Ia. Alternatively, in Step E, the compound of Formula I can be esterified by dissolving in a suitable organic solvent such as ethanol, and treating with an excess of a suitable acid. Examples of suitable acids include gaseous hydrochloric acid, aqueous sulfuric acid, p-toluene sulfonic acid, and the like with gaseous hydrochloric acid being preferred. The reaction mixture is heated to reflux (78-85° C.) for about 15-25 hours. The reaction mixture is then concentrated under vacuum to provide the crude compound of Formula Ia. This material can then be purified by techniques well known in the art, such as cation exchange chromatography eluting with methanol/water followed by 2N ammonia in ethanol to provide the purified compound.

One of ordinary skill in the art will understand that the nitrile group of structure (11) (see Scheme III above) can be converted to a protected tetrazole group prior to treatment of compound (10) with compound (11) and, thus, provide yet another route of synthesis for compounds of Formula I wherein R[1] is tetrazole. This alternate route is provided in Scheme IV(a) and IV(b) below:

Scheme IV(a)

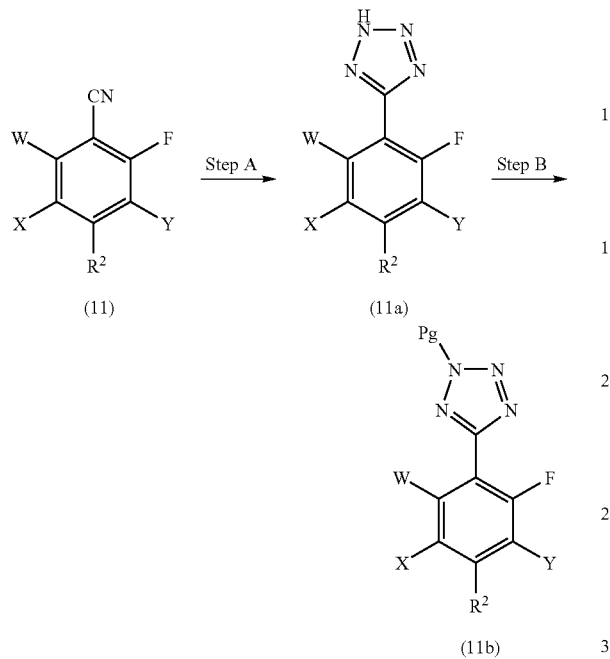

In Scheme IV(a), Step A, the compound of structure (11) is treated under standard conditions to provide the compound of structure (11a). For example, a solution of trimethyl aluminum in toluene is added to a round bottomed flask under nitrogen and the solution cooled to about −7 degrees C. Azidotrimethylsilane (about 3.86 mol) is then added via cannula such that the internal temperature of the reaction is maintained at no greater than about 3 degrees C. To this mixture, the compound of structure (11) is added dropwise in a solution of toluene. The reaction is slowly warmed to RT and then heated to about 90 degrees C. The reaction is heated at 90 degrees for about 13 hours before cooling to RT. The reaction is then cooled to about 0 degrees C. in an ice bath, then slowly transferred via cannula to a solution of 6N aqueous HCl and ethyl acetate, pre-cooled to about −5 degrees C. The internal temperature during the quench is maintained at no greater than about 5 degrees. After addition, the flask is allowed to warm to room temperature. The reaction is then diluted with ethyl acetate to dissolve any solids, the layers are separated, and the aqueous layer extracted with ethyl acetate. The organics are combined, washed with brine, dried over anhydrous sodium sulfate, and concentrated using standard techniques well known in the art to provide the concentrated compound of structure (11a)

In Scheme IV(a), Step B, the compound of structure (11a) is protected with a suitable nitrogen protecting group under standard conditions to provide the compound of structure (11b). For example, to a slurry of compound (11a) and 4,4'-dimethoxybezhydrol in glacial acetic acid, is added concentrated sulfuric acid. Upon addition, the reaction becomes red and homogenous and an endotherm of about 3 to 4 degree Celsius is observed. After about 15 minutes, the product of structure (11b) begins to crystallize, resulting in a slight exotherm of less than about 10 degrees. After about 1 hour, the product is isolated using standard techniques, such as filtration, washed with water, and then with isopropyl alchohol. The product of compound (11b) is dried and concentrated under vaccum to provide the concentrated compound of structure (11b).

Scheme IV(b)

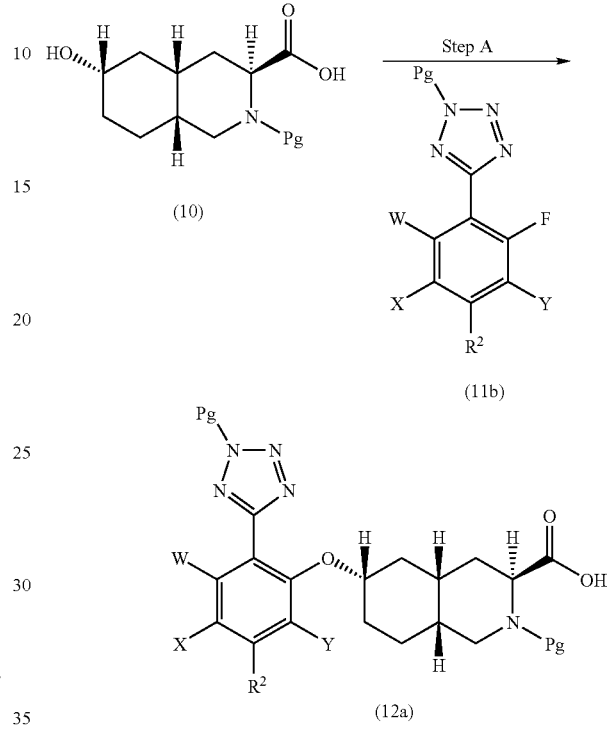

In Scheme IV(b), Step A, the compound of structure (10) (from Scheme III above) is treated with the compound of structure (11b) from Scheme IV(a), Step B. above, to provide the compound of structure (12a). For example, to a solution of sodium hydride in dry dimethyl sulfoxide, is added compound (10) dropwise as a solution of dimethyl sulfoxide. During addition, a cooling bath is used to maintain the reaction temperature at or below about 25 degrees C. The reaction is stirred for about 15 minutes at ambient temperature and then compound (11b) is added in one portion as a solid. The reaction slurry is stirred at RT for about 20 minutes before heating to about 40 degrees C. for about 2.5-3 hours. The reaction is quenched by addition of 1N aqueous HCl solution, water, and ethyl acetate. The layers are separated and the aqueous layer is extracted with ethyl acetate. The combined organics are washed with water and about a 10% solution of aqueous sodium chloride solution. The organic layer is then dried over anhydrous sodium sulfate and concentrated under vaccum to provide the crude compound of structure (12a). This material may then be purified using standard techniques such as chromatography on silica gel, eluting with a suitable eluent such as 1% MeOH in methylene chloride, followed by 5% MeOH in methylene chloride to afford the purified product of compound (12a)

As one of ordinary skill in the art will recognize, the compound of structure (12a) may then be deprotected using, for example TMSI (iodotrimethylsilane) in methylene chloride, to provide the compound of Formula I, wherein R[1] is tetrazole. Alternatively, the compound of structure (12a) may be esterified under standard conditions well known in the art, followed by deprotection, to provide the compound of Formula Ia, wherein $R^6$ is tetrazole.

Scheme IV(a) and IV(b), above, provide procedures for the synthesis of Formula I and I(a) compounds where $R^1$ or $R^6$ is tetrazole, wherein the protected hydroxy acid of compound (10) is treated with the protected aryl tetrazole of compound 11(b) in a nucleophilic aromatic substitution reaction to provide the compound of structure 12(a). As discussed, compound 12(a) can then be esterified and/or deprotected, all under standard conditions, to provide the compounds of Formula I(a) or Formula I. Scheme IV(c) provides a general synthetic route for these procedures.

In Scheme IV(c), Step A, the compound of structure 12(a) is esterified under standard conditions to provide the compound of structure 12(b) wherein $R^6$ is tetrazole. For example, compound 12(a), dissolved in a suitable solvent such as DMF, is treated with a compound of the formula $R^5$-LG where LG represents a suitable leaving group such as a halide. For example $R^5$ is as defined previously and LG represents a chloro or bromo atom. The reaction is heated until complete (confirmed for example by TLC and HPLC). For example, heating at 80° C. under nitrogen for about 1 hour. The reaction is then cooled to ambient temperature and submitted to stan-

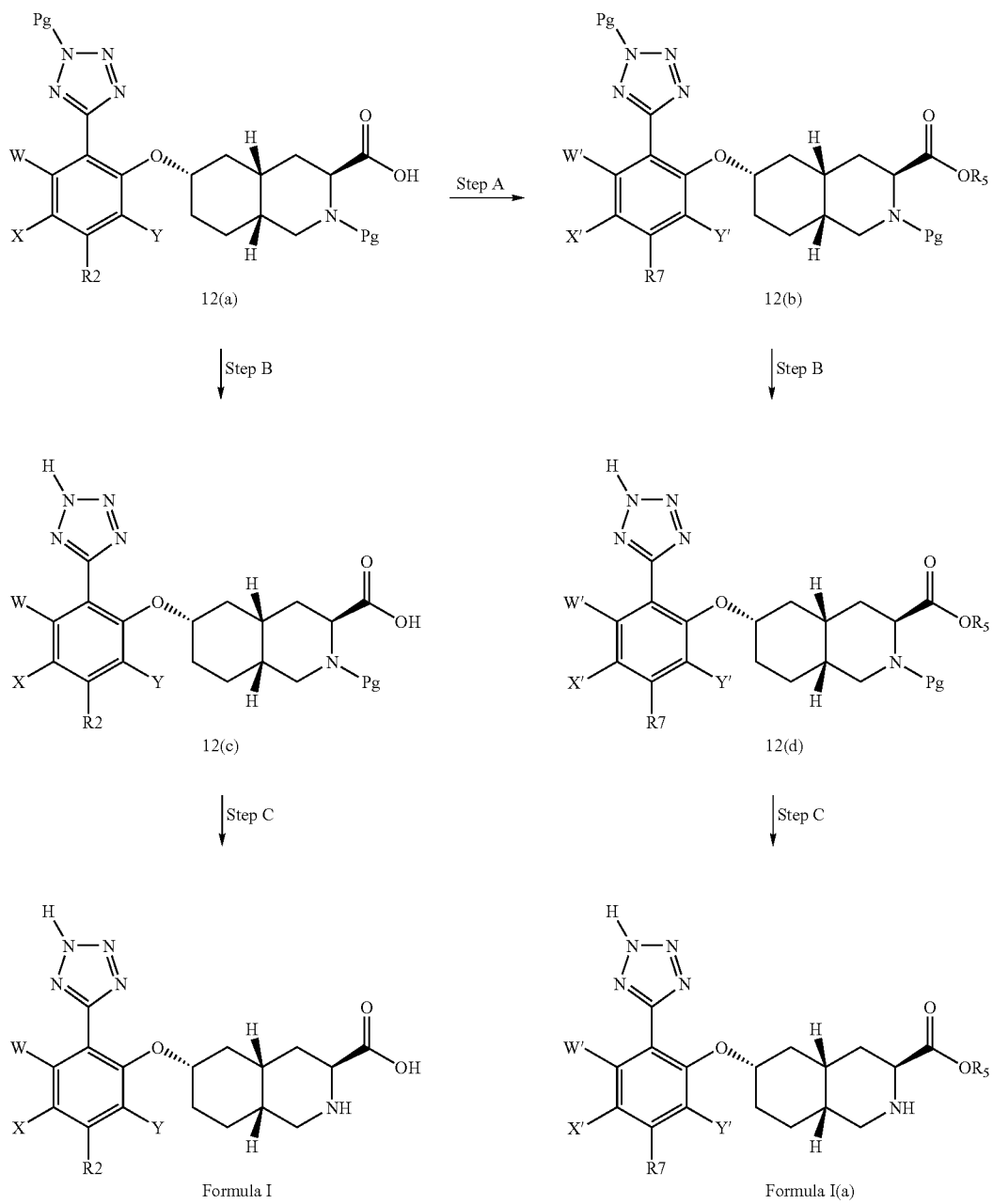

Scheme IV(c)

dard extractive worhup techniques know to the skilled artisan to provide purified compound 12(b), wherein $R^6$ is tetrazole.

In Scheme IV(c), Steps B and C, the compound of structure 12(a) or 12(b) is deprotected under standard conditions to provide Formula I or Formula I(a) wherein $R^1$ or $R^6$ is tetrazole. For example, to a solution of compound 12(a) or 12(b) is added anisole and trifluoroacetic acid (TFA). The solution is stired until the reaction is complete. For example stirring for 6 hours at room temperature. The product, compound 12(c) or 12(d), can be isolated by standard workup conditions.

Compounds 12(c) and 12(d) are further deprotected in Step C to provide the final products of Formula I or I(a) (wherein $R^1$ or $R^6$ is tetrazole). For example, compound 12(c) or 12(d) is combined with TMSI in $CH_2Cl_2$ and the reaction is stired until complete. The Final compounds of Formula I or I(a) wherein $R^1$ or $R^6$ is tetrazole may be isolated after standard workup conditions.

Surprisingly, and as a further embodiment of the present invention, Applicants have discovered alternative nucleophilic aromatic substitution procedures for the synthesis of Formula I or Formula I(a) (wherein $R^1$ or $R^6$ is tetrazole) that offer additional advantages over the procedures described in Schemes IV(a)-IV(c). These additional procedures are generally provided in Scheme IV(d), below.

Scheme IV(d)

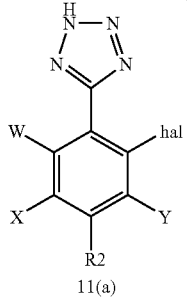

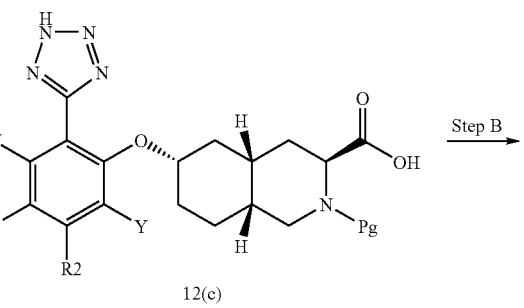

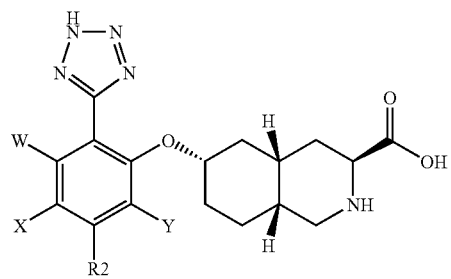

Formula I
(Hydrate salt)

Step C
$R^5$—OH

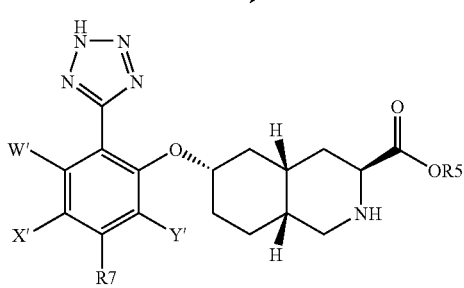

Formula I(a)

In Scheme IV(d), Step A, compound (10) is treated with an unprotected aryl tetrazole of structure 11(a) to provide the compound of structure 12(c). For example, to a solution of a suitable base, such as potassium tert-butoxide, in a suitable solvent, such as THF, is added the compound of structure (10) and the unprotected aryl tetrazole of structure 11(a). The reaction is heated until complete. For example, the reaction is heated to about 65° C. for about 4 hours. The compound 12(c) is isolated by standard workup techniques.

In Scheme IV(d), Step B, compound 12(c) is deprotected to provide the compound of Formula I wherein $R^1$ is tetrazole. For example, to a solution of a suitable base, such as 85% KOH in water, compound 12(c) is added and the mixture is heated to about 100° C. until the reaction is complete. The mixture is cooled then added to a suitable acid, such as HCl, to provide the precipitated acid salt of Formula I, wherein $R^1$ is tetrazole. The acid salt of Formula I ($R^1$ is tetrazole) can purified by standard recrystallization techniques and isolated as the salt or a solvate thereof such as the hydrate.

In Scheme IV(d), Step C, Formula I is esterifed with a compound of the formula $R^5$—OH under standard conditions. For example, a mixture of the hydrate salt of Formula I (Step B above), a suitable acid such as p-toluenesulfonic acid monohydrate, a compound of formula $R^5$—OH, and water is heated to about 140° C. until complete. The ester salt of Formula I(a) where R6 is tetrazole is isolated by standard techniques and may be purified by standard recrystallization techniques.

Compounds of Formula I, wherein Z represents a sulfur atom, may be synthesized according to Scheme V.

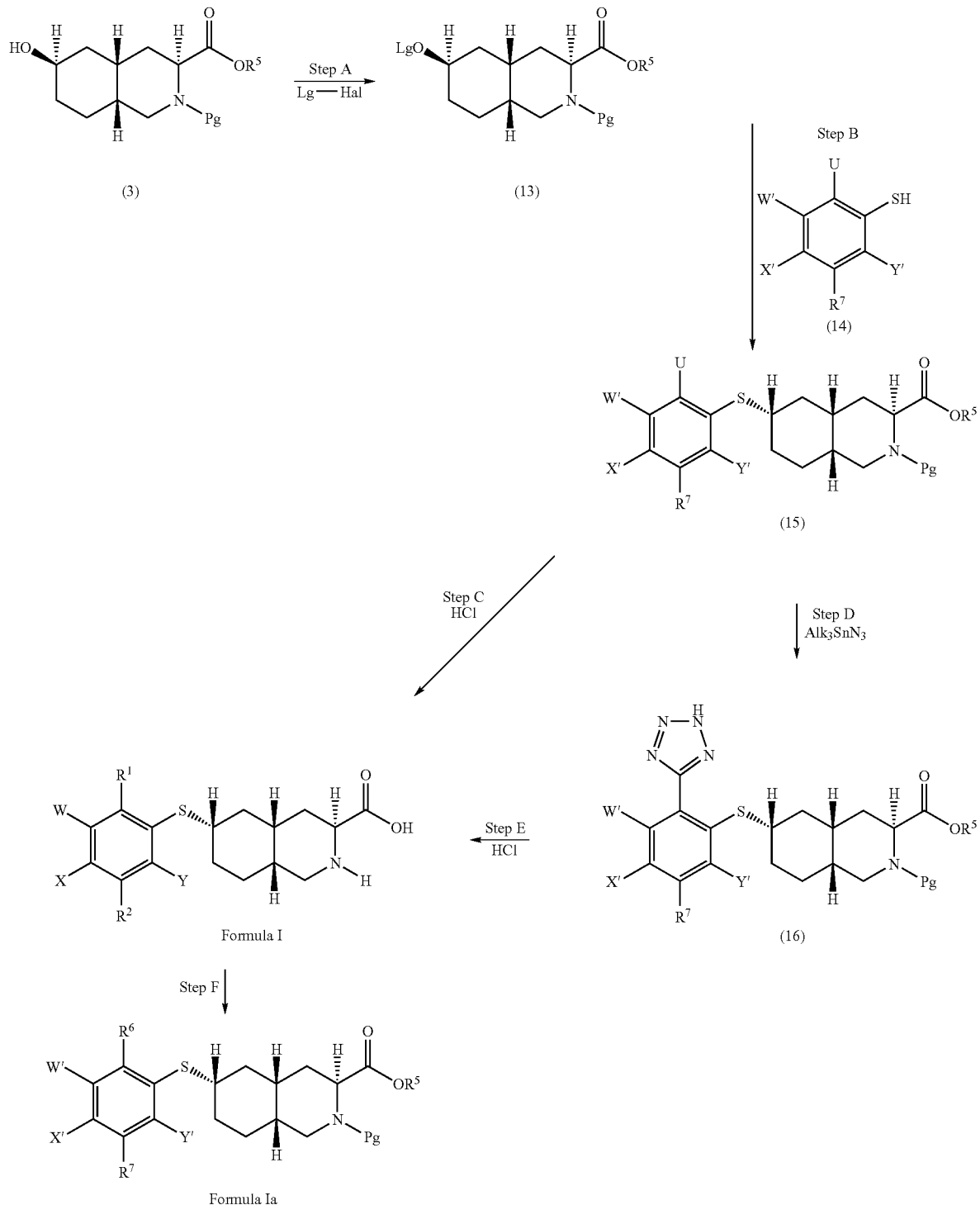

In Scheme V, step A, the compound of structure (3) is treated under standard conditions with a compound of formula Lg-Hal, wherein Lg is a suitable leaving group and Hal represents a chloro, bromo or iodo atom, to provide the compound of structure (13). For example, a solution of ethyl-6-hydroxy-2-(methoxycarbonyl)-decahydroisoquinoline-3-carboxylate, dissolved in a suitable organic solvent such as dichloromethane and cooled to 0° C., is treated with an excess of a suitable organic base, such as triethylamine, followed by about 1 to 2 equivalents of a compound of formula Lg-Hal. Examples of Lg-Hal include m-nitrobenzenesulfonyl chloride, p-nitrobenzenesulfonyl chloride, p-bromobenzenesulfonyl chloride, p-toluenesulfonyl chloride, benzenesulfonyl chloride, methanesulfonyl chloride, trifluoromethanesulfonyl chloride, and the like, with methanesulfonyl chloride being a preferred compound. The reaction mixture is warmed to room temperature and stirred for about 3 to 20 hours. The compound of structure (13) is then isolated using standard procedures. For example, the reaction mixture is washed with water, the organic layer separated, washed with aqueous saturated solution of ammonium chloride, and dried over anhydrous sodium sulfate, filtered, and concentrated under vacuum to provide concentrated compound (13). If desired, column chromatography may then be performed with on silica gel with a suitable eluent such as 10-50% ethyl acetate/hexane to provide the purified compound (13).

In Scheme V, Step B, compound (13) is treated with an aryl thiol of structure (14) to provide the compound of structure (15). For example, ethyl methanesulfonyloxy-2-methoxycarbonyl-decahydroisoquinoline-3-carboxylate is mixed with about 1-2.5 equivalents of substituted aryl thiol (wherein U represents hydrogen, CN, $(C_1-C_4)$alkyl $-CO_2R^9$, or $CO_2R^9$ and where all other substituents are as defined hereinabove) and about 1-2.5 equivalents of potassium carbonate and heated at reflux in a suitable solvent such as acetone for about 24-48 hours. The reaction mixture is cooled to room temperature and compound (15) is then isolated using standard procedures such as extraction techniques. For example, the reaction mixture is partitioned between water and an organic solvent such as ethyl acetate, and the aqueous layer extracted 24 times with ethyl acetate. The organic layers are combined, dried over anhydrous sodium sulfate, filtered, and concentrated under vacuum to provide concentrated compound (15). Compound (15) may then be purified by chromatography on silica gel with a suitable eluent such as ethyl acetate/hexanes.

In Scheme V, Step C, compound (15) is concomitantly deprotected and hydrolyzed under standard conditions to provide the compound of Formula I wherein $R^1$ is other than tetrazole, but otherwise as defined hereinabove. For example, a solution of compound (15) dissolved in 6M HCl is heated to reflux for about 20-50 hours. The reaction mixture is then allowed to cool to room temperature and concentrated in vacuo to provide the compound of Formula I wherein $R^1$ is other than tetrazole, but otherwise as defined hereinabove. The compound of Formula I may then be purified by techniques well known in the art, such as cation exchange chromatography eluting with methanol/water followed by 2 N ammonia in methanol or ethanol to provide the purified compound.

In Scheme V, Step D, where it is desired that the compound of Formula I contain a tetrazole at $R^1$, compound (15), wherein U is nitrile, is treated under standard conditions with a compound of formula $Alk_3SnN_3$, wherein Alk is an alkyl chain, to provide the compound of structure (16). For example, when U is a nitrile group, compound (15) is treated with about 2 to 5 equivalents of azido tri-n-butyl stannane at 70 to 100° C. for about 72-120 hours under an atmosphere of nitrogen to give compound (16). Purification of compound (16) may be achieved by standard flash chromatography using silical gel and a suitable eluent.

In Scheme V, Step E, compound (16) is concomitantly deprotected and hydrolyzed under standard conditions to provide the compound of Formula I, wherein $R^1$ is tetrazole. For example, a solution of compound (16), dissolved in 6M HCl, is heated to reflux for about 20-50 hours. The reaction mixture is then allowed to cool to room temperature, and concentrated in vacuo to provide the compound of Formula I wherein $R^1$ is tetrazole. The compound of Formula I may then be purified by techniques well known in the art, such as cation exchange chromatography eluting with methanol/water, followed by 2 N ammonia in methanol or ethanol to provide the purified compound of Formula I wherein $R^1$ is tetrazole.

In Scheme V, Step F, the compound of Formula I is esterified under standard conditions well known in the art to provide the compound of Formula Ia. For example, the compound of Formula I is dissolved in a suitable organic solvent such as ethanol, and treated with an excess of a suitable acid. Examples of suitable acids include gaseous hydrochloric acid, aqueous sulfuric acid, p-toluene sulfonic acid, and the like with gaseous hydrochloric acid being preferred. The reaction mixture is heated to reflux (78-85° C.) for about 15-24 hours. The reaction mixture is concentrated under vacuum to provide the crude compound of Formula Ia. This material may then be purified by techniques well known in the art, such as cation exchange chromatography eluting with methanol/water, followed by 2 N ammonia in ethanol to provide the purified compound of Formula Ia.

The Formula I compounds of the present invention may be chemically synthesized, for example, from a 6-oxo-2-methoxycarbonyl-decahydroisoquinoline-3-carboxylate intermediate, or a 6-hydroxy-2-tert-butoxycarbonyl-decahydroisoquinoline-3-carboxylate intermediate, or a 6-hydroxy-2-methoxycarbonyl-decahydroisoquinoline-3-carboxylate intermediate. These intermediates, in turn, may be synthesized from a 6-oxo-2-methoxycarbonyl-decahydroisoquinoline-3-carboxylic acid, the synthesis of which is described in U.S. Pat. Nos. 4,902,695, 5,446,051, and 5,356,902 (the contents of which are all herein incorporated by reference). A route for the synthesis of the 6-oxo-2-methoxycarbonyl-decahydroisoquinoline-3-carboxylate intermediate, useful for the synthesis of the compounds of the present invention, is shown in Scheme VI below. Synthesis of the 6-hydroxy-2-tert-butoxycarbonyl-decahydroisoquinoline-3-carboxylate intermediate is provided in Preparation 1 (infra), while synthesis of the 6-hydroxy-2-methoxycarbonyl-decahydroisoquinoline-3-carboxylate is provided, for example, essentially as described in. Scheme I (Steps A and B) and as provided in U.S. Pat. Nos. 4,902,695, 5,446,051, and 5,356,902.

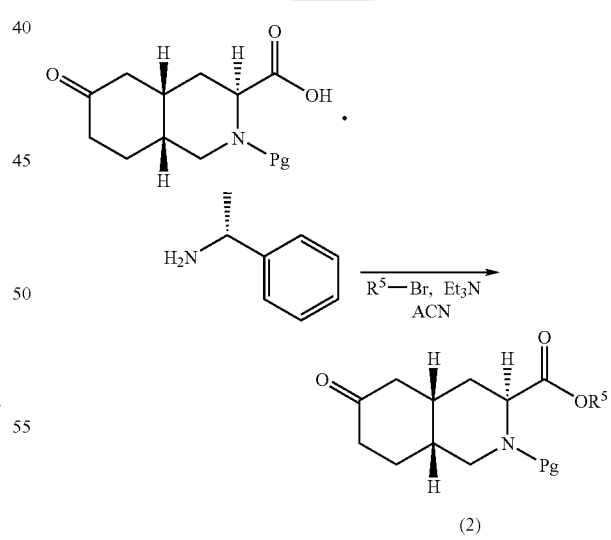

Scheme VI

In Scheme VI, Step A, 6-oxo-2-(Pg)-decahydroisoquinoline-3-carboxylic acid (Pg is as herein defined above) is esterified by reaction with a compound of formula $R^5$-Br (where $R^5$ is as herein defined) to provide the 6-oxo-2-(Pg)-decahydroisoquinoline-3-carboxylate intermediate of compound (2). For example 6-oxo-2-methoxycarbonyl-decahydroisoquinoline-3-carboxylic acid is dissolved in acetonitrile and treated with triethylamine and bromoethane. The reaction is heated at 50° C. for about 3 hours, cooled and partitioned between 50:50 ethyl acetate/heptane and 1N HCL. The organic phase is isolated and washed 3 times with water, saturated sodium bicarbonate, brine, dried over anhydrous sodium sulfate, filtered, and concentrated under vacuum to provide ethyl 6-oxo-2-methoxycarbonyl-decahydroisoquinoline-3-carboxylate, a compound of structure (2). This crude material may then be purified under standard conditions well known in the art. For example, the crude material is dissolved in 10% ethyl acetate/heptane and applied to a plug of silica gel (10 g in 10% ethyl acetate/heptane). The plug is eluted with, 10% ethyl acetate/heptane, 15% ethyl acetate/heptane, and 25% ethyl acetate/heptane. The eluents are combined and concentrated under vacuum to provide the purified compound of structure (2).

The following preparations and examples further illustrate the invention and represent typical synthesis of the compounds of Formula I as described generally above. The reagents and starting materials are readily available, to one of ordinary skill in the art. As used herein, the following terms have the meanings indicated: "i.v." refers to intravenously; "p.o." refers to orally; "i.p." refers to intraperitoneally; "eq" or "equiv." refers to equivalents; "g" refers to grams; "mg" refers to milligrams; "L" refers to liters; "mL" refers to milliliters; "µL" refers to microliters; "mol" refers to moles; "mmol" refers to millimoles; "psi" refers to pounds per square inch; "mm Hg" refers to millimeters of mercury; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "THF" refers to tetrahydrofuran; "DMF" refers to N,N-dimethylformamide; "DMSO" refers to dimethyl sulfoxide; "aq" refers to aqueous; "EtOAc" refers to ethyl acetate; "iProAc" refers to isopropyl acetate; "MeOH" refers to methanol; "MTBE" refers to tert-butyl methyl ether; "$PPh_3$" refers to triphenylphosphine; "DEAD" refers to diethyl azodicarboxylate; "RT" refers to room temperature; "$K_i$" refers to the dissociation constant of an enzyme-antagonist complex and serves as an index of ligand binding; and "$ID_{50}$" and "$ID_{100}$" refer to doses of an administered therapeutic agent which produce, respectively, a 50% and 100% reduction in a physiological response.

Preparation 1

Ethyl (3S, 4aS, 6R, 8aR) 6-hydroxy-2-tert-butoxycarbonyl-1,2,3,4,4a, 5,6,7,8,8a-decahydroisoquinoline-3-carboxylate

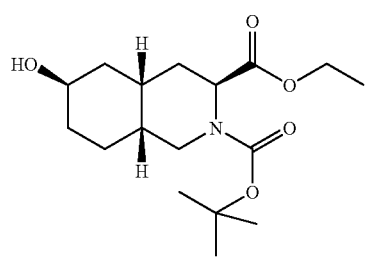

A. Ethyl (3S, 4aS, 6R, 8aR) 6-hydroxy-2-tert-butoxycarbonyl-1,2,3,4,4a, 5,6,7,8,8a-decahydroisoquinoline-3-carboxylate To a −78° C. solution of (3S, 4aS, 8aR) 6-oxo-2-tert-butoxycarbonyl-1,2,3,4,4a, 5,6,7,8,8a-decahydroisoquinoline-3-carboxylic acid (6.88 g, 21.14 mmol)(see Preparation 2, Steps A and B, below and Scheme III, Step A generally) and cerium trichloride heptahydrate (7.9 g, 21.2 mmol) in absolute ethyl alcohol (90 mL), under nitrogen sodium borohydride (1.24 g, 32.73 mmol) was added in portions. The resulting mixture was slowly warmed up to room temperature over 5 hours. The reaction mixture was cooled down to 0° C. and acetic acid (50% in water, 25 mL) was carefully added. The resulting mixture was stirred for 1 hour at room temperature and the solvent was removed in vacuo. To the resulting material water and ethyl acetate were added and the phases separated. Aqueous layer was extracted with ethyl acetate (3×). The combined organic phases were dried, filtered and concentrated in vacuo. Flash chromatography (silicagel, 70% ethyl acetate/hexane) gave ethyl (3S, 4aS, 6S, 8aR) 6-hydroxy-2-tert -butoxycarbonyl-1,2,3,4,4a, 5,6,7,8,8a-decahydroisoquinoline-3-carboxylate (2.4 g, 35%) and the title compound (4.15 g, 60%)

Ion Electrospray Mass Spectrum M+Na: 350.2

EXAMPLE 1

Preparation of (3S, 4aS, 6S, 8aR) 6-(3-Carboxynaphthalen-2-yloxy)-1,2,3,4,4a, 5,6,7,8,8a-decahydroisoquinoline-3-carboxylic acid hydrochloride

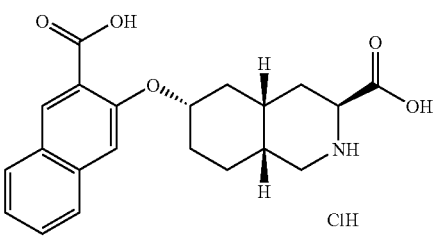

A. Preparation of ethyl (3S, 4aS, 6S, 8aR) 6-(3-ethoxycarbonyl-naphthalen-2-yloxy)-2-tert-butoxycarbonyl-1,2,3,4, 4a, 5,6,7,8,8a-decahydroisoquinoline-3-carboxylate A solution of the material from preparation 1 (120 mg, 0.37 mmol), triphenylphosphine (145 mg, 0.55 mmol), ethyl 3-hydroxy-naphthalen-2-carboxylate (111 mg, 0.55 mmol) in tetrahydrofuran (1.9 ml), was treated with diethylazodicarboxylate (0.090 mL, 0.55 mmol) at room temperature for 16 h. Flash chromatography (silicagel, 50% diethyl ether/hexane) gave 103 mg of the title intermediate (55%).

B. Preparation of (3S, 4aS, 6S, 8aR) 6-(3-Carboxy-naphthalen-2-yloxy)-1,2,3,4,4a, 5,6,7,8,8a-decahydroisoquinoline-3-carboxylic acid hydrochloride To a solution of the material from step A (103 mg, 0.20 mmol) in tetrahydrofuran (0.5 mL) hydrochloric acid (3N, 1 mL) was added. The resulting mixture was stirred at 80° C. for 10 h and concentrated in vacuo to give a solid that was triturated with ethyl acetate, diethyl ether and cold acetone to afford the desired aminoacid (57 mg, 70%).

Mass Spectrum (Fast Atom Bombardement) M-HCl+1: 370.2 $^1$H NMR (CD$_3$OD, 200.13 MHz): 8.35 (s, 1H); 7.83 (t, J=7.9 Hz, 2H); 7.48 (m, 3H); 4.63 (m, 1H); 4.10 (m, 1H); 3.40 (m, 1H); 3.15 (m, 1H); 2.26-1.55 (m, 10H).

EXAMPLE 2

Preparation of (3S, 4aS, 6S, 8aR) 6-(4-carboxy-biphenyl-3-yloxy)-1,2,3,4,4a, 5,6,7,8,8a-decahydroisoquinoline-3-carboxylic acid hydrochloride

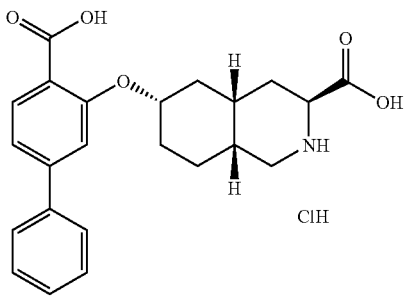

A. Preparation of ethyl (3S, 4aS, 6S, 8aR) 6-(4-ethoxycarbonyl-biphenyl-3-yloxy)-2-tert-butoxycarbonyl-1,2,3,4,4a, 5,6,7,8,8a-decahydroisoquinoline-3-carboxylate Following the procedures as described in Example 1, step A, a solution of the material from preparation 1 (2.02 g, 8.3 mmol), triphenylphosphine (3.15 g, 12.0 mmol), ethyl 3-hydroxy-biphenyl-4-carboxylate (2.63 g, 8.02 mmol) in tetrahydrofuran (42 mL), was treated with diethylazodicarboxylate (1.89 mL, 12.0 mmol) at room temperature for 20 h. Flash chromatography (silicagel, 30% diethyl ether/hexane) gave 2.76 g of the title intermediate (62%).

Mass Spectrum (Fast Atom Bombardement) M+Na: 574.2

B. Preparation of (3S, 4aS, 6S, 8aR) 6-(4-carboxy-biphenyl-3-yloxy)-2-tert-butoxycarbonyl-1,2,3,4,4a, 5,6,7,8,8a-decahydroisoquinoline-3-carboxylic acid To a solution of the material from step A (400 mg) in absolute ethanol (2 mL) a solution of lithium hydroxide (2.5 N, 2 mL) was added. The resulting mixture was stirred at room temperature for 72 hours. The ethanol was removed in vacuo and the mixture extracted with ethyl acetate (2×). The aqueous phase was made acidic by addition of hydrochloric acid (10%, pH=3-4) and extracted with ethyl acetate (3×). The resulting organic phases were combined, dried and concentrated in vacuo to afford, after flash chromatography (silicagel, 50% ethyl acetate/hexane/5% acetic acid), to give the title compound (350 mg, 95%)

Mass Spectrum (Fast Atom Bombardement) M+1: 496.2

C. Preparation of (3S, 4aS, 6S, 8aR) 6-(4-carboxy-biphenyl-3-yloxy)-1,2,3,4,4a, 5,6,7,8,8a-decahydroisoquinoline-3-carboxylic acid hydrochloride The material from step B (350 mg, 0.71 mmol) was treated with ethyl acetate saturated with hydrogen chloride (7 mL) for 4 hours at room temperature. The mixture was concentrated in vacuo to afford, after trituration with ethyl acetate and diethyl ether, the desired aminoacid (250 mg, 82%).

Ion Electrospray Mass Spectrum M-HCl+1: 396.2 $^1$H NMR (CD$_3$OD, 200.13 MHz): 7.90 (d, J=8.1 Hz, 1H); 7.78 (m, 2H); 7.53-7.27 (m, 5H); 4.60 (m, 1H); 4.08 (dd, J=12.03.3 Hz, 1H); 3.37 (m, 1H); 3.12 (dd, 3=12.7, 4.3Hz, 1H); 2.18-1.59 (m, 10H).

EXAMPLE 3

Preparation of ethyl (3S, 4aS, 6S, 8aR) 6-(4-ethoxycarbonyl-biphenyl-3-yloxy) -1,2,3,4,4a, 5,6,7,8,8a-decahydroisoquinoline-3-carboxylate hydrochloride

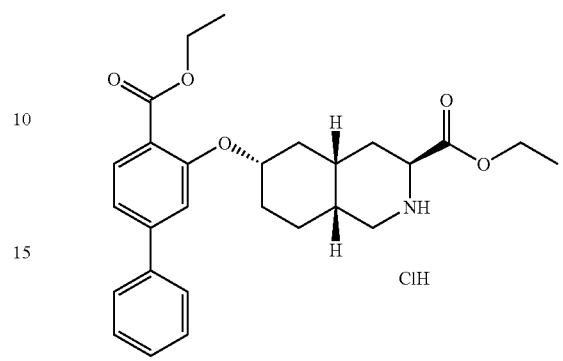

A. Preparation of ethyl (3S, 4aS, 6S, 8aR) 6-(4- ethoxycarbonyl-biphenyl-3-yloxy) -1,2,3,4,4a, 5,6,7,8,8a-decahydroisoquinoline-3-carboxylate hydrochloride Following the procedures as described in Example 2C, material from Example 2A (2.25 g, 4.08 mmol) treated with ethyl acetate saturated with hydrogen chloride (50 mL) gave a solid that was washed with hexane to afford the title compound (1.9 g, 95%).

Ion Electrospray Mass Spectrum M-HCl+1: 452.2 Analysis calcd. for: C27H33NO5.1 HCl. 0.8H2O: C 64.55, H 7.14, N, 2.79; Found: C 64.64, H 7.34, N 3.00.

EXAMPLE 4

Preparation of (3S, 4aS, 6S, 8aR) 6-(2-carboxy-5-chloro-phenoxy)-1,2,3,4,4a, 5,6,7,8,8a-decahydroisoquinoline-3-carboxylic acid hydrochloride

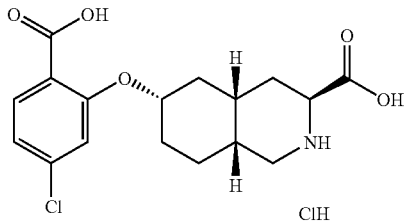

A. Preparation of ethyl (3S, 4aS, 6S, 8aR) 6-(5-chloro-2-ethoxycarbonyl-phenoxy)-2-tert-butoxycarbonyl-1,2,3,4, 4a, 5,6,7,8,8a-decahydroisoquinoline-3-carboxylate Following the procedures as described in Example 1, step A, a solution of the material from preparation 1A (120 mg, 0.37 mmol), triphenylphosphine (145 mg, 0.55 mmol), ethyl 4-chloro-2-hydroxy-benzoate (80 mg, 0.40 mmol) in tetrahydrofuran (1.9 mL), was treated with diethylazodicarboxylate (0.090 mL, 0.55 mmol) at 70° C. for 24 h. Flash chromatography (silicagel, 40% diethyl ether/hexane) gave 132 mg of the title intermediate (71%).

Mass Spectrum (Fast Atom Bombardement) M+1: 510.3

B. Preparation of (3S, 4aS, 6S, 8aR) 6-(2-carboxy-5-chloro-2-phenoxy)-2-tert -butoxycarbonyl-1,2,3,4,4a, 5,6,7,8,8a-decahydroisoquinoline-3-carboxylic acid Following the procedures as described in Example 2B, a solution of the material from step A (132 mg, 0.26 mmol) in tetrahydrofuran (1.2 mL) and absolute ethanol (0.5 mL) was treated with a solution of lithium hydroxide (2.5 N, 1 mL) at room temperature for 24 h to give the title compound (118 mg, 100%).

Mass Spectrum (Fast Atom Bombardement) M+Na: 476.2

C. Preparation of (3S, 4aS, 6S, 8aR) 6-(2-carboxy-5-chloro-2-phenoxy)-1,2,3,4,4a, 5,6,7,8,8a-decahydroisoquinoline-3-carboxylic acid hydrochloride Following the procedures as described in Example 2C, material from step B (118 mg, 0.26 mmol) treated with ethyl acetate saturated with hydrogen chloride (1 mL) gave the desired aminoacid (98 mg, 97%).

Mass Spectrum (Fast Atom Bombardement) M-HCl+1: 354.1 Analysis calcd. for: C17H202NO5.1 HCl. 0.5H2O: C, 51.14; H, 5.55; N, 3.51; Found: C 51.37, H 5.90, N 3.82.

EXAMPLE 5

Preparation of ethyl (35, 4aR, 6S, 8aR) 6-(5-chloro-2-ethoxycarbonyl-phenoxy)-1,2,3,4,4a, 5,6,7,8,8a-decahydroisoquinoline-3-carboxylate hydrochloride

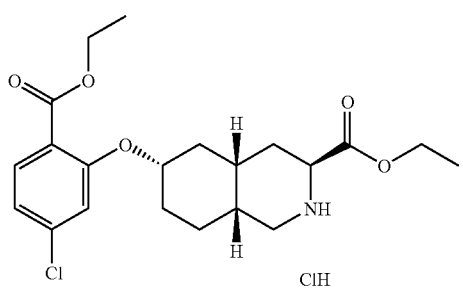

A. Preparation of ethyl (3S, 4aR, 65, 8aR) 6-(5-chloro-2-ethoxycarbonyl-phenoxy)-1,2,3,4,4a, 5,6,7,8,8a-decahydroisoquinoline-3-carboxylate hydrochloride Following the procedures as described in Example 2 step C, material from Example 4, step A (1.25 g, 2.45 mmol) treated with ethyl acetate saturated with hydrogen chloride (20 mL) gave the title compound (930 mg, 93%).

Ion Electrospray Mass Spectrum M-HCl+1: 410.2

$^1$H NMR (CDCl$_3$, 200.13 MHz): 9.85 (br s, 2H); 7.64 (d, J=8.2 Hz, 1H); 6.90 (m, 2H); 5.28 (br s, 1H); 4.24 (m, 5H); 3.91 (br s, 1H); 3.42, 3.26 (2 br s, 2H); 2.65-1.78 (m, 10H); 1.32-1.18 (m, 6H).

EXAMPLE 6

Preparation of (35, 4aR, 6S, 8aR) 6-(2-carboxy-4,5-difluoro-phenoxy)-1,2,3,4,4a, 5,6,7,8,8a-decahydroisoquinoline-3-carboxylic acid hydrochloride

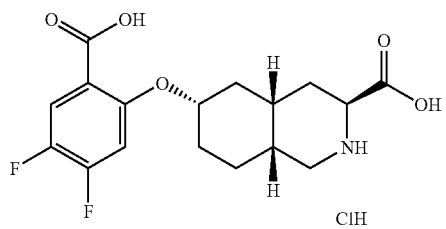

A. Preparation of ethyl (3S, 4aS, 6S, 8aR) 6-(2-ethoxycarbonyl-4,5-difluoro -phenoxy)-2-tert-butoxycarbonyl-1,2,3, 4,4a, 5,6,7,8,8a-decahydroisoquinoline-3-carboxylate Following the procedures as described in Example 1, step A, a solution of the material from preparation 1A (100 mg, 0.31 mmol), triphenylphosphine (121 mg, 0.46 mmol), ethyl 4,5-difluoro-2-hydroxy-benzoate (78 mg, 0.39 mmol) in tetrahydrofuran (1.6 mL), was treated with diethylazodicarboxylate (0.072 mL, 0.46 mmol) at room temperature for 36 h. Flash chromatography (silicagel, 40% diethyl ether/hexane) gave 115 mg of the title intermediate (73%).

Ion Electrospray Mass Spectrum M+Na: 534.2

B. Preparation of (3S, 4aS, 6S, 8aR) 6-(2-carboxy-4,5-difluoro-2-phenoxy)-2-tert -butoxycarbonyl-1,2,3,4,4a, 5,6,7,8,8a-decahydroisoquinoline-3-carboxylic acid Following the procedures as described in Example 2B, a solution of the material from step A (99 mg, 0.21 mmol) in absolute ethanol (1 mL) was treated with a solution of lithium hydroxide (2.5 N, 1 mL) at room temperature for 48 h to give the title compound (87 mg, 100%).

Mass Spectrum (Fast Atom Bombardement) M+Na: 478.2

C. Preparation of (3S, 4aS, 6S, 8aR) 6-(2-carboxy-4,5-difluoro-2-phenoxy)-1,2,3,4,4a, 5,6,7,8,8a-decahydroisoquinoline-3-carboxylic acid hydrochloride Following the procedures as described in Example 2 step C, material from step B (77 mg, 0.17 mmol) treated with ethyl acetate saturated with hydrogen chloride (2 mL) gave, after washing the solid with diethyl ether and acetone, the desired aminoacid (98 mg, 97%).

Mass Spectrum (Fast Atom Bombardement) M-HCl+1: 356.1

$^1$H N (CD$_3$OD, 200.13 MHz): 7.70 (t, J=9.9 Hz, 1H); 7.21 (dd, J=6.6, 5.8 Hz, 1H); 4.44 (m, 1H); 4.07 (br d, J=14.4 Hz, 1H); 3.35 (m, 1H); 3.16 (dd, J=12.5, 3.7 Hz, 1H); 2.23-1.49 (m, 10H).

EXAMPLE 7

Preparation of (3S, 4aS, 6S, 8aR) 6-(2-carboxy-chloro-phenoxy) -1,2,3,4,4a, 5,6,7,8,8a-decahydroisoquinoline-3-carboxylic acid hydrochloride

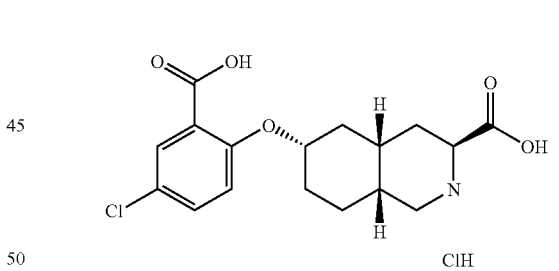

A. Preparation of ethyl (3S, 4aS, 6S, 8aR) 6-(2-ethoxycarbonyl-4-chloro-phenoxy)-2-tert-butoxycarbonyl-1,2,3,4,4a, 5,6,7,8,8a-decahydroisoquinoline-3-carboxylate Following the procedures as described in Example 1, step A, a solution of the material from preparation 1 (120 mg, 0.37 mmol), triphenylphosphine (145 mg, 0.55 mmol), ethyl 2-hydroxy-5-chloro-benzoate (73 mg, 0.366 mmol) in tetrahydrofuran (2 mL), was treated with diethylazodicarboxylate (0.090 mL, 0.55 mmol) at room temperature for 16 h. Flash chromatography (silica gel, diethyl ether-hexane 1:2) gave 106 mg (57% yield) of the title compound.

Mass Spectrum (Fast Atom Bombardement) M+1:511.1

B. Preparation of (3S, 4aS, 6S, 8aR) 6-(2-carboxy-4-chlorophenoxy)-1,2,3,4, 5,6,7,8,8a-decahydroisoquinoline-3-carboxylic acid hydrochloride A solution of the material from step A (106 mg, 0.20 mmol) in tetrahydrofuran (1 mL) was treated with 3N HCl (3 mL) and heated at 80° C. overnight. The crude was concentrate in vacuo and washed with ethyl acetate gel, to afford 25 mg (31% yield) of the title compound.

Mass Spectrum (Fast Atom Bombardement) M-HCl+1: 354.1 Analysis calculated for C17H21Cl2NO5: % C, 52.32; % H, 5.42; % N, 3.59. Found: % C, 52.39; % H, 5.61; % N, 3.60.

EXAMPLE 8

Preparation of (3S, 4aS, 6S, 8aR) 6-(2-carboxy-4-nitro-phenoxy)-1,2,3,4,4a, 5,6,7,8,8a -decahydroisoquinoline-3-carboxylic acid hydrochloride

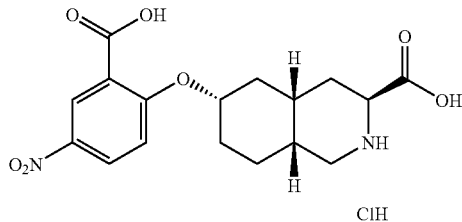

A. Preparation of ethyl (3S, 4aS, 6S, 8aR) 6-(2-ethoxycarbonyl-4-nitro-phenoxy)-2-tert-butoxycarbonyl-1,2,3,4,4a, 5,6,7,8,8a-decahydroisoquinohne-3-carboxylate Following the procedures as described in Example 1A, a solution of the material from preparation 1A (120 mg, 0.37 mmol), triphenylphosphine (145 mg, 0.55 mmol), ethyl 2-hydroxy-5-nitro-benzoate (77 mg, 0.366 mmol) in tetrahydrofuran (2 mL), was treated with diethylazodicarboxylate (0.090 mL, 0.55 mmol) at room temperature for 16 h. Flash chromatography (silica gel, diethyl ether-hexane 1:2) gave 120 mg (63% yield) of the title compound.

Mass Spectrum (Fast Atom Bombardement) M+1:521.3

B. Preparation of (3S, 4aR, 6S, 8aR) 6-(2-carboxy-4-nitrophenoxy)-1,2,3,4,4a,5,6,7,8,8a-decahydroisoquinoline-3-carboxylic acid hydrochloride Following the procedures as described in Example 7, step B, compound from step A (106 mg, 0.23 mmol) afforded 50 mg (54% yield) of the title compound.

Mass Spectrum (Fast Atom Bombardement) M-HCl+1: 365.1 Analysis calculated for C17H21ClN2O7: % C, 50.94; % H, 5.28; % N, 6.99. Found: % C, 50.88; % H, 5.35; % N, 6.80.

Preparation 2

(3S, 4aS, 6S, 8aR) 6-hydroxy-2-tert-butoxycarbonyl-1,2,3,4,4a, 5,6,7,8,8a -decahydroisoquinoline-3-carboxylic acid

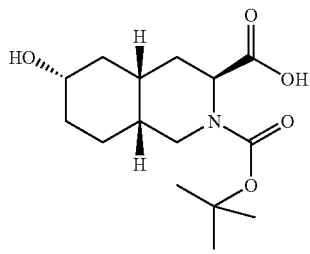

A. Ethyl (3S, 4aR, 8aR) 6-oxo-2-tert-butoxycarbonyl-1,2,3, 4,4a, 5,6,7,8,8a -decahydroisoquinoline-3-carboxylate To a solution of ethyl (3S, 4aR, 6R, 8aR) 6-oxo-2-methoxycarbonyl-1,2,3,4,4a, 5,6,7,8,8a-decahydroisoquinoline-3-carboxylate (3.54 g, 12.5 mmol) in methylene chloride (100 mL) under nitrogen, iodotrimethylsilane (10.0 g, 50 mmol) was added in one portion at room temperature. The reaction mixture was stirred overnight and quenched with ethanol (20-30 mL). The solution was concentrated in vacuo and dried for 3 hours under reduced pressure. The resulting solid was dissolved in methylene chloride (100 mL) and triethylamine (7 mL, 50 mmol) was added. After stirring for 15 minutes a solution of di-tert-butyl-dicarbonate (2.73 g, 12.5 mmol) in methylene chloride(10 mL) was added. The resulting mixture was stirred overnight at room temperature and concentrated in vacuo. The resulting solid was suspended in ethyl acetate and filtered. The filtrate was washed with 1N hydrochloric acid and brine. The organic phase was dried, filtered and concentrated in vacuo. Flash chromatography (silicagel, 25% ethyl acetate/hexane) gave pure product as an colorless oil (3.69 g, 92%).

B. (3S, 4aR, 8aR) 6-oxo-2-tert-butoxycarbonyl-1,2,3,4,4a, 5,6,7,8,8a -decahydroisoquinoline-3-carboxylic acid To a solution of ester from preparation 2A (9.7 g, 29.81 mmol) in absolute ethanol (130 mL) a solution of lithium hydroxide (2.5 N, 132 mL) was added. The resulting mixture was stirred at room temperature for 22 h. The ethanol was removed in vacuo and the resulting mixture was washed with ethyl acetate (x2). The aqueous phase was made acidic by addition of 10% hydrochloric acid (pH=3-4) and extracted with ethyl acetate (x3). The resulting organic phases were combined, dried and concentrated in vacuo to afford the title compound (8.85 g, 100%)

C. (3S, 4aS, 6S, 8aR) 6-hydroxy-2-tert-butoxycarbonyl-1,2, 3,4,4a, 5,6,7,8,8a -decahydroisoquinoline-3-carboxylic acid To an ice-cooled solution of ketone from preparation 2B (11.34 g, 38.14 mmol) in dry tetrahydrofuran (50 mL) under nitrogen a solution of L-Selectride (1 M in tetrahydrofuran, 76 mL) was added dropwise. The resulting mixture was allowed to reach room temperature for 2 h and quenched with 1N hydrochloric acid (78 mL). To the resulting mixture sodium chloride was added to saturate the aqueous phase. After filtration the aqueous phase was extracted with ethyl acetate. The combined organic phases were dried and concentrated in vacuo. Hash chromatography (silicagel, ethyl acetate-hexane 4:3) afforded the desired alcohol (8.5 g, 74%)

EXAMPLE 9

Preparation of (3S, 4aS, 6S, 8aR) 6-[3-Chloro-2-(1 (2)H-tetrazol-5-yl)-phenoxy]-1,2,3,4,4a, 5,6,7,8,8a-decahydroisoquinoline-3-carboxylic acid hydrochloride

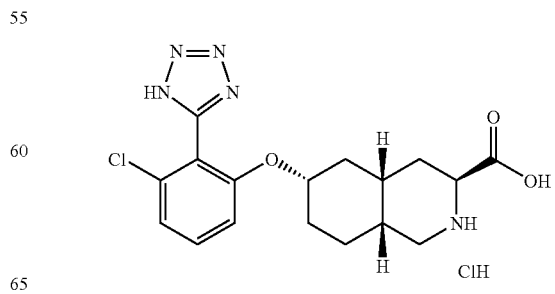

A. Preparation of (3S, 4aS, 6S, 8aR) &(3-chloro-2-cyano-phenoxy)-2-tert -butoxycarbonyl-1,2,3,4,4a, 5,6,7,8,8a-decahydroisoquinoline-3-carboxylic acid To an ice-cooled solution of the material from preparation 2 (400 mg, 1.34 mmol) in dry tetrahydrofuran (5.6 mL) under nitrogen a solution of potassium tert-butoxide (1M in tetrahydrofuran, 3.0 mL) was slowly added. The resulting suspension was stirred at room temperature for 25 min and again cooled to 0-5° C. before the addition of 2-chloro-6-fluorobenzonitrile (249 mg, 1.60 mmol). The reaction mixture was stirred a room temperature overnight, diluted with water and washed with ethyl acetate (x2). The aqueous phase was made acidic (pH=3-4) with 10% hydrochloric acid and extracted with ethyl acetate (x2). The resulting organic phases were combined, dried and concentrated in vacuo. Flash chromatography (silicagel, 75% ethyl acetate/hexane/2.5% acetic acid) gave the desired compound as a white solid (460 mg, 79%).

Ion Electrospray Mass Spectrum M+1-t-butylOCO: 335.2

B. Preparation of (3S, 4aS, 6S, 8aR) 6-[3-chloro-2-(1(2)H-tetrazol-5-yl)-phenoxy]-2-tert-butoxycarbonyl-1,2,3,4,4a, 5,6,7,8,8a-decahydroisoquinoline-3-carboxylic acid A mixture of the nitrile from Example 9, step A (3.03 g, 6.9 mmol) and azidotri-n -butylstannane (7.6 mL, 28 mmol) was stirred under nitrogen at 85° C. for 60 h. The mixture was diluted with ethyl acetate (20 mL) and sodium hydroxide (2.5N, 25 mL) was added. The resulting mixture was stirred for 1 h. The aqueous layer was washed with ethyl acetate (2×) and concentrated in vacuo. Flash chromatography (silicagel, 55% ethyl acetate/hexane/1% acetic acid) gave the desired tetrazol as an oil (1.18 g, 35%).

Ion Electrospray Mass Spectrum M+1: 478.1

C. Preparation of (3S, 4aS, 6S, 8aR) 6-[3-chloro-2-(1(2)H-tetrazol-5-yl)-phenoxy]-1,2,3,4,4a, 5,6,7,8,8a-decahydroisoquinoline-3-carboxylic acid hydrochloride A suspension of the protected decahydroisoquinoline from step B (400 mg, 0.84 mmol) in ethyl acetate saturated with hydrogen chloride (5 mL) was stirred for 4 h at room temperature. The mixture was extracted with water (1×). The aqueous layer was washed with ethyl acetate (2×) and concentrated in vacuo to afford a white solid (320 mg, 92%).

Ion Electrospray Mass Spectrum M-HCl+1: 378.11

$^1$H NMR (CD$_3$OD, 200.13 MHz): 7.54 (t, J=8.3 Hz, 1H); 7.22 (t, J=8.1 Hz, 2H); 4.47 (m, 1H); 4.00 (dd, J=12.6, 3.5 Hz, 1H); 3.21 (t, J=12.6 Hz, 1H); 3.06 (dd, J=12.7, 4.7 Hz, 1H); 2.21-1.59 (m, 10H).

EXAMPLE 10

Preparation of 2-Ethyl-butyl (3S, 4aS, 6S, 8aR) 6-[3-chloro-2-(1(2)H-tetrazol-5-yl) -phenoxy]-1,2,3,4,4a, 5,6,7,8,8a-decahydroisoquinoline-3-carboxylate hydrochloride

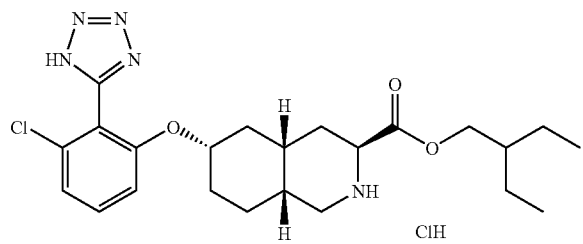

To a suspension of the compound from Example 9, step C (900 mg, 2.18 mmol) in 2-ethylbutanol (50 mL), thionyl chloride (1.75 mil, 24 mmol) was added dropwise. The resulting solution was stirred at 120° C. for 2 h. The solvent was removed in vacuo and diethyl ether was added. The resulting solid was filtered and washed with (#ethyl ether) to give the desired material (711 mg, 70%).

Ion Electrospray Mass Spectrum M-HCl+1: 462.3

$^1$H NMR (CD$_3$OD, 200.13 MHz): 7.53 (t, J=8.0 Hz, 1H); 7.24 (d, J=8.2 Hz, 1 H); 7.19 (d, J=8.0 Hz, 1H); 4.45 (br s, 1H); 4.22 (dd, J=10.8, 5.7 Hz, 1H); 4.14 (m, 2H); 3.23 (t, J=12.6 Hz, 1H); 3.11 (d, J=9.6 Hz, 1H); 2.19-1.36 (m, 15H); 0.91 (t, J=7.5 Hz, 6H).

EXAMPLE 11

Preparation of (3S, 4aS, 6S, 8aR) 6-[3-methoxy-2-(1 (2)H-tetrazol-5-yl)-phenoxy]-1,2,3,4,4a, 5,6,7,8,8a-decahydroisoquinoline-3-carboxylic acid hydrochloride

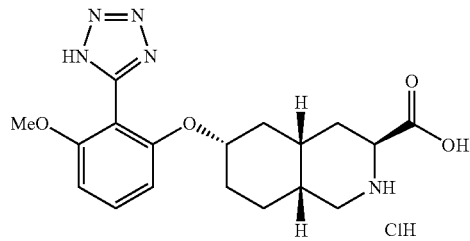

A. Preparation of (3S, 4aS, 6S, 8aR) 6-(3-methoxy-2-cyano-phenoxy)-2-tert -butoxycarbonyl-1,2,3,4,4a, 5,6,7,8,8a-decahydroisoquinoline-3-carboxylic acid Following the procedures as described in Example 9, step A, material from preparation 2 (400 mg, 1.34 mmol) in tetrahydrofuran (5.6 mL) was treated with a solution of potassium tert-butoxide (1 M in tetrahydrofuran, 3.0 mL) and 6-methoxy-2-fluorobenzonitrile (242 mg, 1.60 mmol) to give, after flash chromatography (silicagel, 75% ethyl acetate/hexane/2.5% acetic acid), 429 mg of the title compound (74%).

Ion Electrospray Mass Spectrum M+1-t-butylOCO: 331.3

B. Preparation of (3S, 4aS, 6S, 8aR) 6-[3-methoxy-2-(1(2)H-tetrazol-5-yl)-phenoxy]-1,2,3,4,4a, 5,6,7,8,8a-decahydroisoquinoline-3-carboxylic acid hydrochloride Following the procedures as described in Example 9, step B, compound from step A (429 mg, 0.92 mmol) was treated with azidotri-n-butylstannane (0.8 mL, 3.6 mmol) at 85° C. for 62 h to give 50 mg of an oil that was directly submitted to the next reaction. As for Example 2, step C, the above material was treated with ethyl acetate saturated with hydrogen chloride (2.5 mL) to give the desired aminoacid (17 mg, 5%, two steps).

Ion Electrospray Mass Spectrum M-HCl+1: 374.2

$^1$H NMR (CD$_3$OD, 200.13 MHz): 7.50 (t, J=8.5 Hz, 1H); 6.82 (dd, J=12.0, 8.5 Hz, 2H); 4.43 (m, 1H); 4.02 (dd, J=12.3, 3.6 Hz, 1H); 3.81 (s, 3H); 3.22 (d, J=12.8 Hz, 1H); 3.07 (dd, J=12.8, 4.3 Hz, 1H); 2.14-1.29 (m, 10H).

EXAMPLE 12

Preparation of (3S, 4aS, 6S, 8aR) 6-[3-fluoro-2-(1(2)H-tetrazol-5-yl)-phenoxy]-1,2,3,4,4a, 5,6,7,8,8a-decahydroisoquinoline-3-carboxylic acid hydrochloride

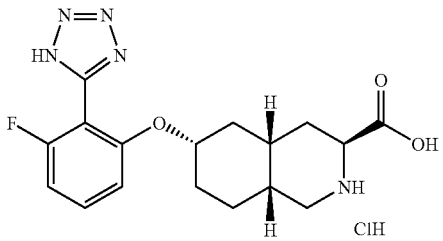

A. Preparation of (3S, 4aS, 6S, 8aR) 6-(3-fluoro-2-cyano-phenoxy)-2-tert-butoxycarbonyl-1,2,3,4,4a, 5,6,7,8,8a-decahydroisoquinoline-3-carboxylic acid Following the procedures as described in Example 9, step A, material from preparation 2 (300 mg, 1 mmol) in tetrahydrofuran (4.2 mL) was treated with a solution of potassium tert-butoxide (1 M in tetrahydrofuran, 2.2 mL) and 2,6 difluorobenzonitrile (209 mg, 1.5 mmol) to give 377 mg of the title compound (90%).

Ion Electrospray Mass Spectrum M+Na: 441.2

B. Preparation of (3S, 4aS, 6S, 8aR) 6-[3-fluoro-2-(1(2)H-tetrazol-5-yl)phenoxy]-2-tert-butoxycarbonyl-1,2,3,4,4a, 5,6,7,8,8a-decahydroisoquinoline-3-carboxylic acid Following the procedures as described in Example 9, step B, compound from step A (370 mg, 0.88 mmol) was treated with azidotri-n-butylstannane (1.0 mL, 3.6 mmol) at 90° C. for 31 h to give the desired compound (120 mg, 29%).

Ion Electrospray Mass Spectrum M+1: 462.3

C. Preparation of (3S, 4aS, 6S, 8aR) 6-[3-fluoro-2-(1(2)H-tetrazol-5-yl)-phenoxy]-1,2,3,4,4a, 5,6,7,8,8a-decahydroisoquinoline-3-carboxylic acid hydrochloride Following the procedures as described in Example 9, step C, material from step B (120 mg, 0.26 mmol) treated with ethyl acetate saturated with hydrogen chloride (3 mL) gave the desired aminoacid (60 mg, 64%).

Ion Electrospray Mass Spectrum M-HCl+1: 362.2

$^1$H NMR (CD$_3$OD, 200.13 MHz): 7.57 (dt, J=8.3, 6.7 Hz, 1H); 7.13 (d, J=8.9 Hz, 1H); 6.97-6.88 (m, 1H); 4.59-4.49 (m, 1H); 4.05 (dd, J=12.1, 4.3-Hz, 1H); 3.38-3.25 (m, 1H); 3.11 (dd, J=12.9, 4.6 Hz, 1H); 2.27-1.39 (m, 10H).

EXAMPLE 13

Preparation of (3S, 4aS, 6S, 8aR) 6-[4-fluoro-2-(1(2)H-tetrazol-5-yl)-phenoxy]-1,2,3,4,4a, 5,6,7,8,8a-decahydroisoquinohne-3-carboxylic acid hydrochloride

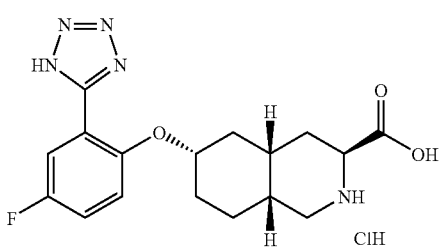

A. Preparation of (3S, 4aS, 6S, 8aR) 6-(4-fluoro-2-cyano-phenoxy)-2-tert-butoxycarbonyl-1,2,3,4,4a, 5,6,7,8,8a-decahydroisoquinoline-3-carboxylic acid Following the procedures as described in Example 9, step A, material from preparation 2 (300 mg, 1 mmol) in tetrahydrofuran (4.2 mL) was treated with a solution of potassium tert-butoxide (1 M in tetrahydrofuran, 2.2 mL) and 2,5-difluorobenzonitrile (209 mg, 1.5 mmol) to give 344 mg of the title compound (82%).

Ion Electrospray Mass Spectrum M+Na: 441.2

B. Preparation of (3S, 4aS, 6S, 8aR) 6-[4-fluoro-2-(1(2)H-tetrazol-5-yl)-phenoxy]-2-tert-butoxycarbonyl-1,2,3,4,4a, 5,6,7,8,8a-decahydroisoquinoline-3-carboxylic acid Following the procedures as described in Example 9, step B, compound from step A (344 mg, 0.82 mmol) was treated with azidotri-n-butylstannane (0.9 mL, 3.3 mmol) at 90° C. for 24 h to give the desired compound (249 mg, 66%).

Ion Electrospray Mass Spectrum M+1: 462.3

C. Preparation of (3S, 4aS, 6S, 8aR) 6-[4-fluoro-2-(1(2)H-tetrazol-5-yl)-phenoxy]-1,2,3,4,4a, 5,6,7,8,8a-decahydroisoquinoline-3-carboxylic acid hydrochloride Following the procedures as described in Example 9, step C, material from step B (249 mg, 0.54 mmol) treated with ethyl acetate saturated with hydrogen chloride (2.5 mL) gave the desired compound (70 mg, 36%)

Ion Electrospray Mass Spectrum M-HCl+1: 362.2

$^1$H NMR (CD$_3$OD, 200.13 MHz): 7.70 (dt, J=8.4, 1.9H, 1 H); 7.33 (dd, J=5.9, 1.5 Hz, 2H); 4.54 (m, 1H); 4.02 (dd, J=12.2, 4.2 Hz, 1H); 3.42-3.30 (m, 1H); 3.14 (dd, J=12.8, 4.4 Hz, 1H); 2.17-1.52 (m, 10H).

EXAMPLE 14

Preparation of (3S, 4aS, 6S, 8aR) 6-[4-methyl-2-(1(2)H-tetrazol-5-yl)-phenoxy]-1,2,3,4,4a, 5,6,7,8,8a-decahydroisoquinoline-3-carboxylic acid hydrochloride

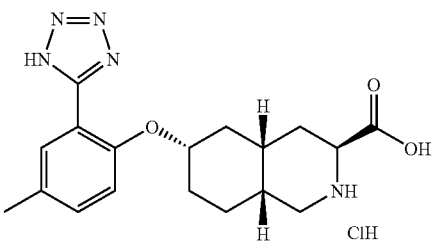

A. Preparation of (3S, 4aS, 6S, 8aR) 6-(4-methyl-2-cyano-phenoxy)-2-tert -butoxycarbonyl-1,2,3,4,4a, 5,6,7,8,8a-decahydroisoquinoline-3-carboxylic acid Following the procedures as described in Example 9, step A, material from preparation 2 (170 mg, 0.57 mmol) in tetrahydrofuran (2.4 mL) was treated with a solution of potassium tert-butoxide (1 M in tetrahydrofuran, 1.2 mL) and 5-methyl-2-fluorobenzonitrile (85 mg, 0.62 mmol) to give, after flash chromatography (silicagel, 60% ethyl acetate/hexane/2.5% acetic acid), 187 mg of the title compound (79%).

Ion Electrospray Mass Spectrum M+1: 415.2

B. Preparation of (3S, 4aS, 6S, 8aR) 6-[4-methyl-2-(1(2)H-tetrazol-5-yl)-phenoxy]-1,2,3,4,4a, 5,6,7,8,8a-decahydroisoquinoline-3-carboxylic acid hydrochloride Following the procedures as described in Example 9, step B, compound from step A (147 mg, 0.36 mmol) was treated with azidotri-n-butylstannane (0.44 mL, 1.5 mmol) at 90° C. for 64 h to give a solid (80 mg, 49%) that was directly submitted to the next reaction. The solid was treated with ethyl acetate saturated with hydrogen chloride (1 mL) and hydrochloric acid (1 mL) to give the desired aminoacid (37 mg, 29%, two steps)

Ion Electrospray Mass Spectrum M-HCl+1: 358.3

$^1$H NMR (CD$_3$OD, 500 MHz): 7.79 (s, 1H); 7.35 (d, J=7.1 Hz, 1H); 7.18 (d, J=8.6 Hz, 1H); 4.54 (m, 1H); 4.07 (d, J=11.1 Hz, 1H); 3.40 (t, J=12.9 Hz, 1H); 3.14 (d, J=9.5 Hz, 1H); 2.34 (s, 3H); 2.32-1.57 (m, 10H).

EXAMPLE 15

Preparation of (3S, 4aS, 6S, 8aR) 6-[5-bromo-2-(1 (2)H-tetrazol-5-yl)-phenoxy]-1,2,3,4,4a, 5,6,7,8,8a-decahydroisoquinoline-3-carboxylic acid hydrochloride

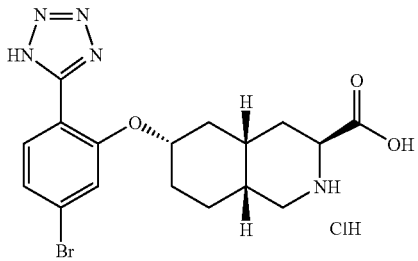

A. Preparation of (3S, 4aS, 6S, 8aR) 6-(5-bromo-2-cyano-phenoxy)-2-tert-butoxycarbonyl-1,2,3,4,4a, 5,6,7,8,8a-decahydroisoquinoline-3-carboxylic acid Following the procedures as described in Example 9, step A, material from preparation 2 (350 mg, 1.17 mmol) in tetrahydrofuran (4.9 mL) was treated with a solution of potassium tert-butoxide (1 M in tetrahydrofuran, 2.6 mL) and 5-methyl-2-fluorobenzonitrile (281 mg, 2.34 mmol) to give, after flash chromatography (silicagel, 70% ethyl acetate/hexane/2.5% acetic acid), 470 mg of the title compound (72%).

Ion Electrospray Mass Spectrum M+Na: 501.0

B. Preparation of (3S, 4aS, 6S, 8aR) 6-[5-bromo-2-(1(2)H-tetrazol-5-yl)-phenoxy]-2-tert-butoxycarbonyl-1,2,3,4,4a, 5,6,7,8,8a-decahydroisoquinoline-3-carboxylic acid Following the procedures as described in Example 9, step B, compound from step A (468 mg, 0.98 mmol) was treated with azidotri-n-butylstannane (1.1 mL, 3.92 mmol) at 85° C. for 30 h to give the desired compound (380 mg, 74. %).

Ion Electrospray Mass Spectrum M+1: 522.1

C. Preparation of (3S, 4aS, 6S, 8aR) 6-[5-bromo-2-(1(2)H-tetrazol-5-yl)-phenoxy]-1,2,3,4,4a, 5,6,7,8,8a-decahydroisoquinoline-3-carboxylic acid hydrochloride Following the procedures as described in Example 9, step C, material from step B (378 mg, 0.72 mmol) treated with ethyl acetate saturated with hydrogen chloride (6 mL) gave the desired aminoacid (290 mg, 95%)

Ion Electrospray Mass Spectrum M-HCl+1: 422.0 Analysis calcd. for: C17H20BrN5O3.1 HCl. 1.5H2O: C, 42.03; H, 4.98; N, 14.42; Found: C, 41.75; H, 4.59; N, 14.02.

EXAMPLE 16

Preparation of (3S, 4aS, 6S, 8aR) 6-[3,5-difluoro-2-(1(2)H-tetrazol-5-yl)-phenoxy]-1,2,3,4,4a, 5,6,7,8, 8a-decahydroisoquinoline-3-carboxylic acid hydrochloride

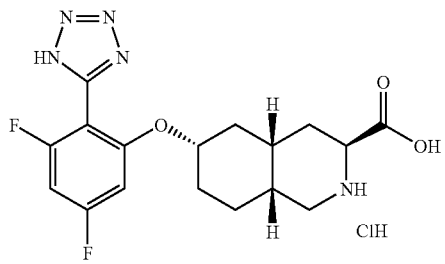

A. Preparation of (3S, 4aS, 6S, 8aR) 6-(3,5-difluoro-2-cyano-phenoxy)-2-tert-butoxycarbonyl-1,2,3,4,4a, 5,6,7,8,8a-decahydroisoquinohne-3-carboxylic acid Following the procedures as described in Example 9, step A, material from preparation 2 (150 mg, 0.50 mmol) in tetrahydrofuran (2.0 mL) was treated with a solution of potassium tert-butoxide (1 M in tetrahydrofuran, 1.1 mL) and 2,4,6-trifluorobenzonitrile (102 mg, 0.65 mmol) to give, after flash chromatography (silicagel, 50% ethyl acetate/hexane/ 0.5% acetic acid), 75 mg of the title compound (35%).

Ion Electrospray Mass Spectrum M+Na: 459.2

B. Preparation of (3S, 4aS, 6S, 8aR) 6-[3,5-difluoro-2-(1(2) H-tetrazol-5-yl)-phenoxy]-1,2,3,4,4a, 5,6,7,8,8a-decahydroisoquinoline-3-carboxylic acid hydrochloride To the compound from step A (75 mg, 0.17 mmol), toluene (0.2 mL) and azidotri-n-butylstannane (140 µL, 0.51 mmol) were added at room temperature. The reaction mixture was allowed to stir at 100° C. for four days. Then, it was cooled at room temperature and treated with a 1N solution of hydrogen chloride in ethyl acetate(5 mL). The reaction mixture was allowed to stir at room temperature for 2 hours. The resulting white solid was washed with ethyl acetate and ethyl ether to give, after purification by HPLC [YMC C18, 2×5 cm, (A) water/0.05% trifluoroacetic acid, (B) acetonitrile/0.05% trifluoroacetic acid; 10 mL/min, 5-40% B in 15 min] the desired aminoacid (6 mg, 9%, two steps).

Ion Electrospray Mass Spectrum M-HCl+1: 380.2

$^1$H-NMR (MeOH-d4, 200.15 MHz): 7.02 (dd, J=11.0, 1.6 Hz, 1H); 6.87-6.76 (m, 1H); 4.59-4.39 (m, 1H); 4.02 (dd, J=12.6, 3.8 Hz, 1H); 3.21-3.05 (m, 2H); 2.20-1.78 (m, 8H); 1.49-1.29 (m, 2H).

EXAMPLE 17

Preparation of (3S, 4aS, 6S, 8aR) 6-[4-chloro-2-(1 (2)H-tetrazol-5-yl)-phenoxy]-1,2,3,4,4a, 5,6,7,8,8a-decahydroisoquinoline-3-caboxylic acid hydrochloride

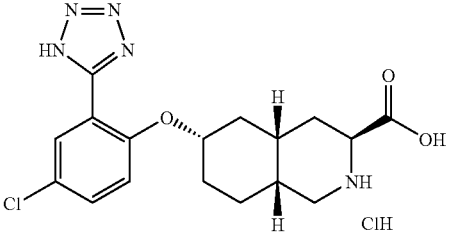

A. Preparation of ethyl (3S, 4aS, 6S, 8aR) 6-(4-chloro-2-cyano-phenoxy)-2-tert-butoxycarbonyl-1,2,3,4,4a, 5,6,7,8,8a-decahydroisoquinoline-3-carboxylate To a solution of the material from preparation 1 (120 mg, 0.37 mmol), triphenylphosphine (145 mg, 0.55 mmol) and 5-chloro-2-hydroxy-benzonitrile (136 mg, 0.89 mmol) in dry tetrahydrofuran (1.9 mL) under nitrogen, neat diethylazodicarboxylate (0.090 mL, 0.55 mmol) was added dropwise at room temperature. The reaction mixture was stirred overnight at room temperature and concentrated in vacuo. Flash chromatography (silicagel, 25% ethyl acetate/hexane) gave 61 mg of the desired compound(36%).

Ion Electrospray Mass Spectrum M+1: 463.2

B. Preparation of (3S, 4aS, 6S, 8aR) 6-(4-chloro-2-(1(2)H-tetrazol-5-yl)-phenoxy)-2-tert-butoxycarbonyl-1,2,3,4,4a, 5,6,7,8,8a-decahydroisoquinoline-3-carboxylic acid A mixture of the material from step A (120 mg, 0.26 mmol) and azidotri-n-butylstannane (0.21 mL, 0.78 mmol) was stirred under nitrogen at 50° C. for 76 h and at 70° C. overnight. The reaction mixture was directly treated with ethanol (2 mL) and lithium hydroxide aqueous solution (40%, 2.5 mL) and stirred at room temperature for 24 h. The reaction mixture was diluted with water and washed with ethyl acetate (2×). The aqueous layer was made acidic by addition of hydrochloric acid (10%, till pH=5-6) and extracted with ethyl acetate (3×). The combined organic phases were dried and concentrated in vacuo to afford the title compound as a foam (98 mg, 79%, two steps).

Ion Electrospray Mass Spectrum M+1: 478.2

C. Preparation of (3S, 4aS, 6S, 8aR) 6-[4-chloro-2-(1(2)H-tetrazol-5-yl)-phenoxy]1,2,3,4,4a, 5,6,7,8,8a-decahydroisoquinoline-3-carboxylic acid hydrochloride The material from step B (95 mg, 0.2 mmol) was treated with hydrochloric acid (5N, 1.5 mL) at room temperature for 5 h to give, after trituration with ethyl acetate and diethyl ether, the desired aminoacid (37 mg, 49%)

Ion Electrospray Mass Spectrum M-HCl+1: 378.1

$^1$H NMR (CD$_3$OD, 200.13 MHz): 7.95 (d, J=2.6 Hz, 1H); 7.54 (dd, J=9.0, 2.6 Hz, 1H); 7.32 (d, J=9.0 Hz, 1H); 4.59 (m, 1H); 4.14 (dd, J=13.4, 2.7 Hz, 1H); 3.22 (dd, J=13.0, 4.4 Hz, 1H); 2.21-1.65 (m, 10H).

EXAMPLE 18

Preparation of (3S, 4aS, 6S, 8aR) 6-[5-methyl-2-(1(2)H-tetrazol-5-yl)-phenoxy]-1,2,3,4,4a, 5,6,7,8,8a-decahydroisoquinoline-3-carboxylic acid hydrochloride

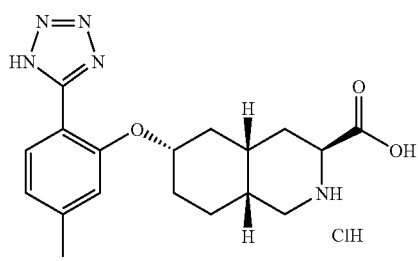

A. Preparation of ethyl (3S, 4aS, 6S, 8aR) 6-(5-methyl-2-cyano-phenoxy)-2-tert-butoxycarbonyl-1,2,3,4,4a, 5,6,7,8,8a-decahydroisoquinoline-3-carboxylate.

To a solution of the material from preparation 1 (200 mg, 0.61 mmol), triphenylphosphine (192 mg, 0.73 mmol), 4-methyl-2-hydroxy-benzonitrile (89 mg, 0.67 mmol) and dry pyridine (0.055 mL, 0.67 mmol) in dry tetrahydrofuran (3.1 mL) under nitrogen, neat diethylazodicarboxylate (0.115 mL, 0.73 mmol) was added dropwise at 0° C. The reaction mixture was stirred for 48 h at room temperature and concentrated in vacuo. A solution of the material in methylene chloride was washed with sodium hydroxide aqueous solution (0.5 M, x2), dried and evaporated in vacuo. Flash chromatography (silicagel, 25% ethyl acetate/hexane) gave 86 mg of the desired compound (32%).

Ion Electrospray Mass Spectrum M+1-t-butylOCO: 343.3

B. Preparation of (3S, 4aS, 6S, 8aR) 6-[5-methyl-2-(1(2)H-tetrazol-5-yl)-phenoxy]-1,2,3,4,4a, 5,6,7,8,8a-decahydroisoquinoline-3-carboxylic acid hydrochloride Following the procedures as described in Example 17, step B the material from step A (70 mg, 0.15 mmol) was treated with azidotri-n-butylstannane (0.125 mL, 0.45 mmol) at 85° C. for 76 h and then treated with ethanol (1.5 mL) and lithium hydroxide aqueous solution (40%, 2 mL) for 48 h to afford a material (33 mg) that was directly submitted to the next reaction. The above material was treated with ethyl acetate saturated with hydrogen chloride (2 mL) at room temperature for 4 h to give, after trituration with ethyl acetate and diethyl ether, the title compound (17 mg, 65%, three steps)

Ion Electrospray Mass Spectrum M+1: 358.3

$^1$H NMR (CD$_3$OD, 200.13 MHz): 7.86 (d, I=7.9H-z, 1H); 7.14 (s, 1H); 6.96(d, J=7.9 Hz, 1H); 4.89 (m, 1H); 4.09 (dd, J=12.3, 3.7 Hz, 1H); 3.42 (t, J=13.0 Hz, 1H); 3.15 (dd, J=12.9, 4.1 Hz, 1H); 2.43 (s, 3H); 2.21-1.51 (m, 10H).

EXAMPLE 19

Preparation of (3S, 4aS, 6S, 8aR) 6-[5-methoxy-2-(1(2)H-tetrazol-5-yl)-phenoxy]-1,2,3,4,4a, 5,6,7,8,8a-decahydroisoquinoline-3-carboxylic acid hydrochloride

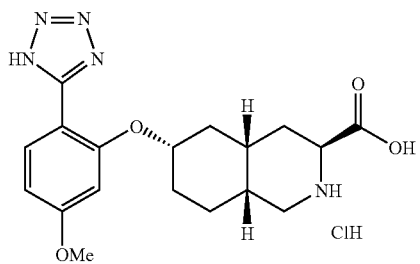

A. Preparation of ethyl (3S, 4aS, 6S, 8aR) 6-(5-methoxy-2-cyano-phenoxy)-2-tert-butoxycarbonyl-1,2,3,4,4a, 5,6,7,8,8a-decahydroisoquinoline-3-carboxylate Following the procedures as described in Example 18, step A, a solution of the material from preparation 1, triphenylphosphine, 4-methoxy-2-hydroxy-benzonitrile (100 mg, 0.67 mmol) and pyridine in tetrahydrofuran, was treated with diethylazodicarboxylate at room temperature for 24 h. Flash chromatography (silicagel, 35% ethyl acetate/hexane) gave 150 mg of the desired compound (54%).

Ion Electrospray Mass Spectrum M+Na: 481.1

B. Preparation of (3S, 4aS, 6S, 8aR) 6-[5-methoxy-2-(1(2)H-tetrazol-5-yl)-phenoxy]-1,2,3,4,4a, 5,6,7,8,8a-decahydroisoquinoline-3-carboxylic acid hydrochloride Following the procedures as described in Example 17, step B the material from step A (125 mg, 0.27 mmol) was treated with azidotri-n-butylstannane (0.225 mL, 0.82 mmol) at 85°

C. for 45 h and then treated with ethanol (2 mL) and lithium hydroxide aqueous solution (40%, 2.5 mL) for 48 h to afford an oil (79 mg) that was directly treated with ethyl acetate saturated with hydrogen chloride (2 mL) to give the title compound (45 mg, 41%, three steps)

Ion Electrospray Mass Spectrum M+1: 374.2 Analysis calcd. for: C18H23N5O4.1.7 HCl.0.2 CH3CH2OH: C, 49.71; H, 5.87; N, 15.75; Found: C, 50.05; H, 5.52; N, 15.51.

EXAMPLE 20

Preparation of (3S, 4aS, 6S, 8aR) 6-[2-(1(2)H-tetrazol-5-yl)-phenoxy]-1,2,3,4,4a, 5,6,7,8,8a-decahydroisoquinoline-3-carboxylic acid

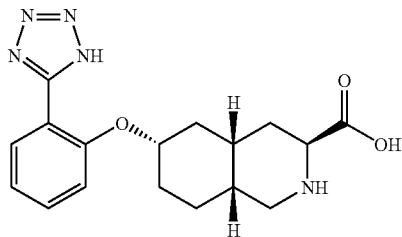

A. Preparation of ethyl (3S, 4aR, 6S, 8aR) 6-(2-cyano-phenoxy)-2-tert -butoxycarbonyl-1,2,3,4,4a, 5,6,7,8,8a-decahydroisoquinoline-3-carboxylate Following the procedures as described in Example 18, step A, a solution of the material from preparation 1 (400 mg, 1.22 mmol), triphenylphosphine (384 mg, 1.46 mmol), 2-hydroxy-benzonitrile (160 mg, 1.34 mmol) and pyridine (0.11 mL, 1.34 mmol) in tetrahydrofuran (6.1 mL), was treated with diethylazodicarboxylate (0.23 mL, 1.46 mmol) at room temperature for 43 h. Flash chromatography (silicagel, 35% ethyl acetate/hexane) gave 264 mg of the desired intermediate (51%).

Mass Spectrum (Fast Atom Bombardement) M+1: 429.3

B. (3S, 4aS, 6S, 8aR) 6-[2-(1(2)H-tetrazol-5-yl)-phenoxy]-1, 2,3,4,4a, 5,6,7,8,8a -decahydroisoquinoline-3-carboxylic acid The intermediate from step A (45 mg, 0.105 mmol), was treated with azidotributyltin (0.17 mL, 0.626 mmol) and heated at 80° C. for three days. The mixture was concentrated in vacuo and treated with 2.5 M lithium hydroxide solution (3 mL) and heated at 50° C. overnight. Then the mixture was extracted with ethyl acetate and the aqueous phase was separated and treated with ethyl acetate saturated with hydrogen chloride and extracted. The aqueous phase was concentrated in vacuo, the product was dissolved in water and then Dowex resin (2.0 g) was added and stirred for 1 h. The resin was washed with water and 50 mL 1:1 tetrahydrofuran/water. The resin was collected, a 10% solution pyridine-water was added and the mixture was stirred for 2 hours, filtered and the filtrate was collected. The resin was washed with water (10 mL) and the combined pyridine-water filtrate was concentrated in vacuo to give 18 mg (50% yield) of the title compound.

Mass Spectrum (East Atom Bombardement) M+1: 344.2
$^1$H NMR (CD$_3$OD, 200.13 MHz): 7.54 (m, 1H); 7.33 (m, 1H); 7.13 (m, 2H); 4.12 (m, 1H); 3.22 (m, 1H); 2.95 (m, 1H); 2.59 (m, 1H); 2.10-1.39 (m, 10H).

EXAMPLE 21

Preparation of (3S, 4aS, 6S, 8aR) 6-[5-Benzyloxy-3-fluoro-2-(1(2)H-tetrazol-5-yl) -phenoxy]1,2,3,4,4a, 5,6,7,8,8a-decahydroisoquinoline-3-carboxylic acid hydrochloride

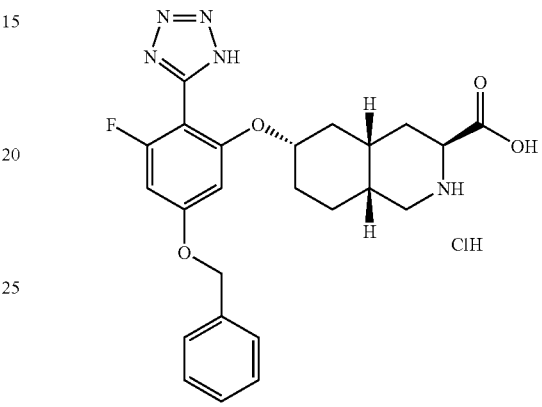

A. 4-Benzyloxy-2,6-difluorobenzonitrile

To a suspension of 2,4,6-trifluorobenzonitrile (314 mg, 2.00 mmol) and potassium carbonate (828 mg, 6.00 mmol) in dry N,N-dimethylformamide (3 mL) at 100° C. was added a solution of benzyl alcohol (216 mg, 2.00 mL) in dry N,N-dimethylformamide (1 mL) using a syringe pump over 4 h and the resulting mixture was stirred at 100° C. for 1 h. The reaction mixture was stirred at room temperature overnight and water and ethyl acetate were added and the phases separated. The organic phase was washed with 1.2 M hydrochloric acid (3×) and the combined organic phases were back-extractted with ethyl acetate (3×). The organic phases were dried (sodium sulfate), filtered, concentrated in vacuo and the residue was purified by flash chromatography (silica gel, hexanes-ethyl acetate 15:1) to give a white solid, mixture of regioisomers. The title product was obtained as a white solid (51 mg, 10%) by HPLC purification (reversed phase).

Ion Electrospray Mass Spectrum M+18: 263.

B. Preparation of ethyl (3S, 4aS, 6S, 8aR) 6-(5-benzyloxy-3-fluoro-2-cyano-phenoxy)-2-tert-butoxycarbonyl-1,2,3,4, 4a, 5,6,7,8,8a-decahydroisoquinoline-3-carboxylate Following the procedures as described for Example 9, step A, reaction of material from step A (51 mg, 0.21 mmol) with Preparation 1 (52 mg, 0.18 mmol) and potassium tert-butoxide (0.40 mL, 0.40 mmol) in tetrahydrofuran (2 mL) gave, after flash chromatography (silica gel, hexanes-ethyl acetate-acetic acid: 1:1:0.01) the desired product as a white solid (58 mg) in 61% yield.

Ion Electrospray Mass Spectrum M+Na: 547

C. Preparation of (3S, 4aS, 6S, 8aR) 6-[5-Benzyloxy-3-fluoro-2-(1(2)H-tetrazol-5-yl) -phenoxy]-1,2,3,4,4a, 5,6, 7,8,8a-decahydroisoquinoline-3-carboxylic acid hydrochloride As for Example 9, step B, the reaction between material from step B (58 mg, 0.11 mmol) and azido tributyltin (8 equiv, 292 mg, 0.88 mmol) at 90° C. for 5 d gave the desired tetrazol.

The crude product was disolved in 1 M hydrogen chloride/ethyl acetate solution (5 mL) and the mixture was stirred at room temperature 2 h and filtered. The solid was washed with ethyl, dried and purified by solid-phase extraction to give pure aminoacid as a pale yellow solid (25 mg, 45%) and small amount (7 mg, 13%) slightly impure.

Ion Electrospray Mass Spectrum M+1: 568.

Preparation 3

Preparation of ethyl (3S, 4aR, 6R, 8aR) 6-methanesulfonyloxy-2-methoxycarbonyl-1,2,3,4,4a, 5,6,7,8,8a-decahydroisoquinoline-3-carboxylate

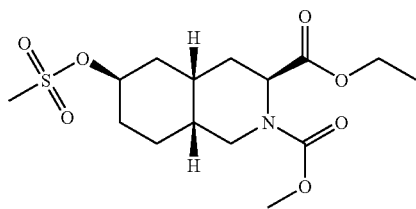

To an ice-cooled solution of ethyl (3S, 4aR, 6R, 8aR) 6-hydroxy-2-methoxycarbonyl-1,2,3,4,4a, 5,6,7,8,8a-decahydroisoquinoline-3-carboxylate (760 mg, 2.66 mmol) in dry dichloromethane (10 mL) under nitrogen, triethylamine (0.60 mL, 4.3 mmol) and methanesulfonyl chloride (0.33 mL, 4.3 mmol) were added. The resulting mixture was stirred overnight at room temperature and a saturated solution of ammonium chloride was added (10 mL). The layers were separated and the aqueous layer extracted with dichloromethane (10 mL×2). The combined organic phases were washed with 1 N hydrochloric acid (10 mL), dried over sodium sulfate and concentrated in vacuo to give the title compound as an oil (0.965 g, 100%).

Ion Electrospray Mass Spectrum M+1: 364

EXAMPLE 22

Preparation of (3S, 4aS, 6S, 8aR) 6-((3-carboxy-2-naphthalenyl)thio)-1,2,3,4,4a, 5,6,7,8,8a-decahydroisoquinoline-3-carboxylic acid hydrochloride

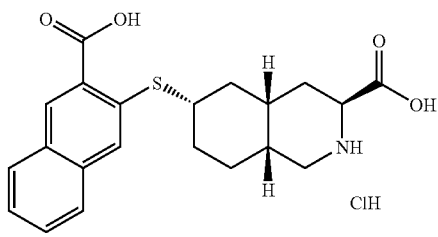

A.  Methyl-3-(((trifluoromethane)sulfonyl)oxy)-2-naphthoate.

To a solution of methyl 3-hydroxy-2-naphtoate (500 mg, 2.47 mmol) and 4-(N,N-dimethylamino)pyridine (603 mg, 4.94 mmol) in dichloromethane (25 mL) at 0° C. under nitrogen, trifluoromethanesulfonic anhydride (677 mg, 0.404 mL, 2.97 mmol) was added dropwise and the reaction mixture was stirred for 10 min at 0° C. and then at room temperature until no starting material is left according to TLC (hexane-ethyl acetate 9:1) (a second addition of 0.1-0.2 equiv of trifluoromethanesulfonic anhydride might be required). The reaction mixture was treated with saturated aqueous solution of ammonium chloride and the phases separated. The organic phase was washed twice with saturated aqueous solution of ammonium chloride and the aqueous were phases back-extracted with dichloromethane. The combined organic phases were washed with brine, treated with a spoon of silica gel to remove trazes of N,N-dimethylaminopyridine, dried with anhydrous sodium sulfate, filtered and concentrated in vacuo, to afford the desired triflate in quantitative yield (845 mg) as a white solid. The product was used without further purification.

Electronic Impact Mass Spectrum M+: 334. Analysis Calculated for $C_{13}H_9F_3O_5S$: C, 46.71; H, 2.71 Found: C, 46.54; H, 2.66

B. Methyl 3-mercapto-2-naphthoate

To a carefully deoxygenated solution of the compound from step A (200 mg, 0.60 mmol) in dry benzene (2 mL) under nitrogen at room temperature, a solution of tetrakistriphenylphosphine palladium (0) (0.05 equiv, 34 mg, 0.03 mmol) and sodium triisopropilsilanethiolate in dry tetrahydrofuran [1.3 equiv, prepared from triisopropilsilanethiol (148 mg, 0.78 mmol) and sodium hydride (95%, 20 mg, 0.78 mmol) in tetrahydrofuran (2 mL) at 0° C. 5-10 min, then 5-10 min at room temperature] was added and the reaction mixture was warmed to reflux (bath temp-90° C.) for 1.5 h. The reaction mixture was cooled down and concentrated in vacuo. The crude residue was dissolved in tetrahydrofuran (5 mL) and treated with tetrabutylammonium fluoride (1 M solution in tetrahydrofuran, 1 equiv, 0.6 mL, 0.6 mmol) at 0° C. and stirred for 45 min. Glacial acetic acid (0.5 mL) was added and the reaction mixture stirred at 0° C. for 15 min. Diethyl ether and water were added and the phases separated. The aqueous phase was extracted twice with diethyl ether and the organic phases dried (sodium sulfate-magnesium sulfate) filtered and concentrated in vacuo. Flash chromatography (silica gel, hexane-ethyl acetate 25:1) gave the desired thiol as a white solid (91 mg, 69%).

Electronic Impact Mass Spectrum M+: 218.

C. Ethyl (3S, 4aS, 6S, 8aR) 6-((3-methoxycarbonyl-2-naphthalenyl)thio)-2-methoxycarbonyl-1,2,3,4,4a, 5,6,7,8,8a-decahydroisoquinoline-3-carboxylate To a solution of decahydroisoquinoline mesylate from preparation 3 (76 mg, 0.21 mmol) in acetone (0.5 mL), potassium carbonate solid (29 mg, 0.21 mmol) was added under nitrogen, followed by addition of a solution of thiol from step B (45 mg, 0.21 mmol) in acetone (0.5 mL) under nitrogen, and the resulting yellow suspension stirred under reflux for 7 h. More potassium carbonate solid (29 mg, 0.21 mmol) and more thiol from step B (45 mg, 0.21 mmol) in acetone (0.5 mL) were added and the mixture stirred under reflux overnight. The reaction mixture was cooled down and concentrated in vacuo. Flash chromatography (silica gel, hexane-ethyl acetate 2.5:1) gave the desired product (36.5 mg, 36% yield).

$^1$H NMR (CDCl$_3$, 200.15 MHz): 8.39 (s, 1H); 7.83 d, J=7.8 Hz, 1H) 7.74 (d, overlapping, 1H); 7.72 (s, 1H); 7.58-7.41 (m, 2H); 4.74 (dd, J=5.8, 3.4 Hz, 1H); 4.16 (q, 7.2Hz, 2H); 3.96 (s, 3H); 3.70 (s, 3H); 3.68 (m, 2H); 3.30 (br d, J=11Hz, 1H); 2.45 (m, 1H); 2.2-1.7 (m, 8H); 1.45 (m, 1H); 1.24 (t, J=7.1 Hz, 3H).

D. (3S, 4aS, 6S, 8aR) 6-((3-Carboxy-2-naphthalenyl)thio)-1, 2,3,4,4a, 5,6,7,8,8a -decahydroisoquinoline-3-carboxylic acid hydrochloride The alkylated decahydroisoquinoline derivative from step C (36 mg, 0.075 mmol) was treated with 6M hydrochloric acid under reflux for 35 h. The solution was concentrated in vacuo and water added and concentrated in vacuo (3×), followed by addition of acetone and concentration in vacuo (3×), to give an off-white solid (30 mg, 96% yield).

M.p.>183° C. with dec. Fast Atom Bombardment Mass Spectrum M-Cl+1: 386. Analysis Calculated for $C_{21}H_{24}NO_4S·2H_2O$: C, 55.08; H, 6.16; N, 3.06 Found: C, 55.08; H, 6.34; N, 3.19

EXAMPLE 23

Preparation of (3S, 4aS, 6S, 8aR) 6-(2-(1(2)H-tetrazolylphenyl)thio)-1,2,3,4,4a, 5,6,7,8,8a-decahydroisoquinoline-3-carboxylic acid hydrochloride

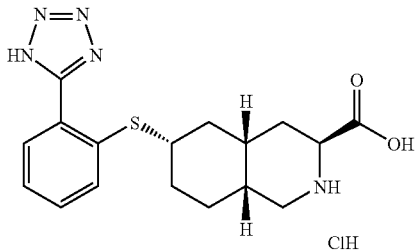

A. Ethyl (3S, 4aS, 6S, 8aR) 6-((2-cyanophenyl)thio)-2-methoxycarbonyl-1,2,3,4,4a, 5,6,7,8,8a-decahydroisoquinoline-3-carboxylate Following the procedures for Example 22, Step C, decahydroisoquinoline mesylate from preparation 3 (102 mg, 0.28 mmol) in acetone (0.5 mL), potassium carbonate solid (38 mg, 0.28 mmol, twice) and 2-mercaptobenzonitrile (38 mg, 0.286 mmol, twice) gave, after flash chromatography (hexanes-ethyl acetate 2:1), the desired product as an oil (64 mg) in 57% yield.

Electronic Impact Mass Spectrum M+: 402.

B. (3S, 4aS, 6S, 8aR) 6-(2-(1(2)H-Tetrazolylphenyl)thio)-1,2,3,4,4a, 5,6,7,8,8a -decahydroisoquinoline-3-carboxylic acid hydrochloride The alkylated decahydroisoquinoline from step A (122 mg, 0.30 mmol) and azidotributyltin (199 mg, 0.60 mmol) were stirred at 80° C. for 2 days. More azidotributyltin (242 mg, 0.73 mmol) was added and the reaction stirred at 80° C. 3 more days. Diethyl ether and hexane were added and the oil was washed twice and dried in vacuo. The residue was treated with 6M HCl under reflux for 1.5 days. The reaction mixture was elaborated as in example 22, Step D to give the title compound in 98% yield as a pale beige solid.

Fast Atom Bombardment Mass Spectrum M+1: 360 Analysis Calculated for $C_{17}H_{22}ClN_5O_2S·3H_2O$: C, 45.38; H, 6.27; N, 15.56 Found: C, 45.18; H. 5.82; N, 15.35

EXAMPLE 24

Preparation of (3S, 4aS, 6S, 8aR) 6-((2-carboxy-5-methylphenyl)thio)-1,2,3,4,4a, 5,6,7,8,8a-decahydroisoquinoline-3-carboxylic acid hydrochloride

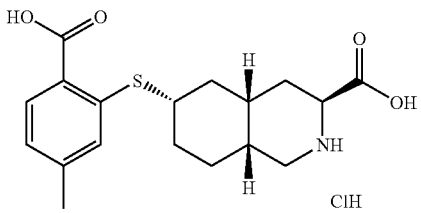

A. Ethyl 4-methyl-2-((trifluoromethyl)sulfonyl)oxy)benzoate

Following the procedures for Example 22, Step A, ethyl 4-methylsalicylate (500 mg, 2.77 mmol), 4-(N,N-dimethylamino)pyridine (676 mg, 5.54 mmol) and trifluoromethanesulfonic anhydride (938 mg, 0.447 mL, 3.32 mmol) gave the desired triflate as a pale orange oil (760 mg, 88% yield). The product was used without further purification.

Electronic Impact Mass Spectrum M+: 312. Analysis Calculated for $C_{11}H_{11}F_3O_5S$: C, 42.31; H, 3.55 Found: C, 42.89; H. 3.84

B. Ethyl 2-mercapto-4-methylbenzoate

To a solution of the triflate from step A (500 mg, 1.60 mmol) and tetrakistriphenylphosphine palladium(0) (0.05 equiv, 92 mg, 0.08 mmol) in dry benzene (2 mL) under nitrogen at room temperature, a solution of sodium triisopropilsilanethiolate in dry tetrahydrofuran [1.3 equiv, prepared from triisopropilsilanethiol (396 mg, 2.08 mmol) and sodium hydride (95%, 52 mg, 2.08 mmol) in tetrahydrofuran (2 mL) as in Example 22, Step B] was added and the reaction mixture was warmed to reflux (bath temp 90° C.) for 3.5 h. The reaction mixture was cooled down to 0° C. and tetrabutylammonium fluoride (1 M solution in tetrahydrofuran, 1.5 equiv, 3.1 mL, 3.1 mmol) and glacial acetic acid (3.5 equiv, 437 mg, 0.405 nL, 7.28 mmol) were added and the reaction mixture stirred at 0° C. for 20 min. Work-up as in Example 22, Step B gave, after flash chromatography (silica gel, hexane-ethyl acetate 25:1), the desired thiol as an oil (220 mg, 70%). The product was kept under nitrogen at −18° C.

Electronic Impact Mass Spectrum M+: 196.

C. Ethyl (3S, 4aS, 6S, 8aR) 6-((2-ethoxycarbonyl-5-methylphenyl)thio)-2-methoxycarbonyl-1,2,3,4,4a, 5,6,7,8,8a-decahydroisoquinoline-3-carboxylate Following the procedures for Example 22, Step C, decahydroisoquinoline mesylate from preparation 3 (145 mg, 0.40 mmol), potassium carbonate solid (65 mg, 0.46 mmol, twice) and thiol from step B (90 mg, 0.42 mmol, twice) gave, after flash chromatography (silica gel, hexane-ethyl acetate 3:1) the desired product (107 mg, 57% yield)

Electronic Impact Mass Spectrum M+: 463.

D. (3S, 4aS, 6S, 8aR) 6-((2-Carboxy-5-methylphenyl)thio)-1,2,3,4,4a, 5,6,7,8,8a -decahydroisoquinoline-3-carboxylic acid hydrochloride Following the procedures for Example 22, Step D, extensive hydrolysis of material from step C (54 mg, 0.12 mmol) with 6M hydrochloric acid (3 mL) gave the title product (39 mg, 84% yield).

M.p.>177° C. (dec). Fast Atom Bombardment Mass Spectrum M-HCl+1: 350.

$^1$H NMR (CD$_3$OD, 200.15 MHz): 7.78 (d, J=7.9 Hz, 1H); 7.29 (s, 1H); 7.03 (d, J=7.7 Hz, 1H); 4.01 (m, 1H); 3.5-3.2 (m, 2H); 3.09 (br d, J=10.3 Hz, 1H); 2.37 (s, 3H); 2.3-1.6 (m, 8H); 1.4 (m, 2H).

EXAMPLE 25

Preparation of (3S, 4aS, 6S, 8aR) 6-((2-carboxy-5-chlorophenyl)thio)-1,2,3,4,4a, 5,6,7,8,8a-decahydroisoquinoline-3-carboxylic acid hydrochloride

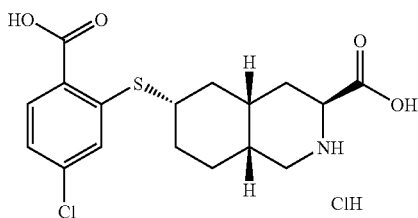

A. Ethyl 2-mercapto-4-Chlorobenzoate.

4-Chloro-2-mercaptobenzoic acid (2.9 g, 15.4 mmol) was dissolved in ethanol (200 mL) and concentrated sulfuric acid (9 mL) was added. The solution was stirred at 80-85° C. overnight. The solvent was evaporated in vacuo. The residue was dissolved with 200 mL of diethyl ether and washed with water (100 mL) and sodium bicarbonate saturated solution (2×100 mL). The organic layer was dried, filtered and concentrated in vacuo. Flash chromatography (silica gel, 15% ethyl acetate/hexane) gave 2.5 g of the title compound (75%).

Electronic Impact Mass Spectrum M+: 216.

B. Ethyl (3S, 4aS, 6S, 8aR) 6-((2-ethoxycarbonyl-5-chlorophenyl)thio)-2-methoxycarbonyl-1,2,3,4,4a, 5,6,7,8,8a-decahydroisoquinoline-3-carboxylate To the intermediate from step A (70 mg, 0.32 mmol) a solution of the material from preparation 3 (78 mg, 0.21 mmol) in acetone (2 mL) was added, followed by addition of anhydrous potassium carbonate solid (50 mg, 0.36 mmol). The resulting yellow suspension was stirred under reflux for 24 h. More anhydrous potassium carbonate (50 mg, 0.36 mmol) and more thiol from step A (70 mg, 0.32 mmol) in acetone (0.5 mL) were added and the mixture stirred under reflux for 20 h. The reaction was cooled down and quenched with a saturated solution of ammonium chloride (1 mL). The mixture was extracted with ethyl acetate (10 mL) and the organic layer was dried, filtered and concentrated in vacuo. Flash chromatography (silica gel, 60% diethyl ether/hexane) gave the title compound as an oil in 67% yield.

Electronic Impact Mass Spectrum M+1: 485

C. (3S, 4aS, 6S, 8aR) 6((2-Carboxy-5-chlorophenyl)thio)1,2,3,4,4a, 5,6,7,8,8a -decahydroisoquinoline-3-carboxylic acid hydrochloride The intermediate from step B (30 mg, 0.06 mmol) was treated with 6M hydrochloric acid under reflux for 60 h. The solution was cooled down and concentrated in vacuo, followed by washing the resulting solid with acetone (3×5 mL), to give an off-white solid (17 mg, 68%)

Fast Atom Bombardment Mass Spectrum M+1: 370 Analysis calculated for C$_{17}$H$_{21}$Cl$_2$NO$_4$S.1.5H$_2$O: C, 47.12; H, 5.58; N, 3.23. Found: C, 47.12; H, 5.51; N, 3.39.

EXAMPLE 26

Preparation of (3S, 4aS, 6S, 8aR) 6-((2-carboxy-4-chlorophenyl)thio)-1,2,3,4,4a, 5,6,7,8,8a-decahydroisoquinoline-3-carboxylic Acid Hydrochloride

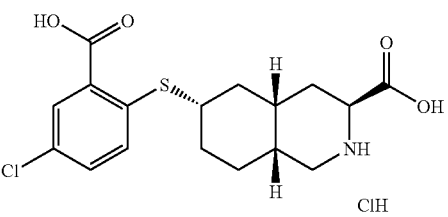

A. Ethyl 5-chloro-2-(((trifluoromethyl)sulfonyl)oxy)benzoate

To a solution of 5-chlorosalicylic acid ethyl ester (500 mg, 2.49 mmol) and 2,6-lutidine (534 mg, 0.58 mL, 4.98 mmol) in dichloromethane at 0° C., trifluoromethanesulfonic anhydride (773 mg, 0.46 mL, 2.74 mmol) was added dropwise and the reaction was stirred 6 h at room temperature. More trifluoromethanesulfonic anhydride (0.25 mL) and 2,6-lutidine (1.1 mL) were added and the reaction stirred at room temperature overnight. More trifluoromethanesulfonic anhydride (0.35 mL) and 2,6-lutidine (0.40 mL) and 4(N,N-dimethylamino)pyridine (44 mg, 0.36 mmol) were added and the reaction was stirred at room temperature overnight. The reaction mixture was treated with 1.2M hydrochloric acid and the phases were separated. The aqueous phase was back-extracted with dichloromethane and the combined organic phases were washed with brine, dried with anhydrous sodium sulfate, filtered and concentrated in vacuo. The residue was purified by flash chromatography (silica gel, hexane-ethyl acetate 65:1) to give the triflate as a pale yellow oil (547 mg, 66% yield).

Electronic Impact Mass Spectrum M+: 332.

B. Ethyl 2-mercapto-5-chlorobenzoate

To a solution of the triflate from step A (100 mg, 0.30 mmol) in dry toluene (2 mL) under nitrogen at room temperature, a solution of tetrakistriphenylphosphine palladium (0) (0.10 equiv, 35 mg, 0.03 mmol) and sodium triisopropilsilanethiolate in dry tetrahydrofuran (1.0 equiv, prepared from triisopropilsilanethiol (190 mg, 1.0 mmol) and sodium hydride (95%, 24 mg, 1.0 mmol) in tetrahydrofuran (2 mL) as in Example 22, Step B) was added and the reaction mixture was warmed at 90° C. (bath temp) for 4 h. The reaction mixture was cooled down and concentrated in vacuo. Flash chromatography (silica gel, hexane-ethyl acetate 40:1) gave 92 mg of a mixture of triisopropylsilylarylthiol and free arylthiol contaminated with small amounts of triphenylphosphine, which was used without further purification in next step.

Electronic Impact Mass Spectrum M+-triisopropylsilyl: 216

C. Ethyl (3S, 4aS, 6S, 8aR) 6-((2-ethoxycarbonyl-4-chlorophenyl)thio)-2-methoxycarbonyl-1,2,3,4,4a, 5,6,7,8,8a-decahydroisoquinoline-3-carboxylate To a solution of the mixture from step B in N,N-dimethylformamide (0.5 mL), tetrabutylammonium fluoride (1 M solution in tetrahydrofuran, 0.12 mL, 0.12 mmol) was added and the reaction mixture was stirred for 1 h at room temperature. A solution of material from preparation 3 (50 mg, 0.13 mmol) in N,N-dimethylformamide (0.5 mL) was then added and the resulting mixture was stirred at 60° C. overnight. Ethyl acetate and water were added and the phases were separated. The organic phase was washed sucessively with 1.2 M hydrochloric acid, brine, dried (sodium sulfate) and concentrated in vacuo. The residue was purified by flash chromatography (silical gel, hexane-diethyl ether 2:3) to give the desired product in 17% yield.

Electronic Impact Mass Spectrum M+−3 carboxylates: 279.

D. (3S, 4aS, 6S, 8aR) 6-((2-Carboxy-4-chlorophenyl)thio)-1,2,3,4,4a, 5,6,7,8,8a -decahydroisoquinoline-3-carboxylic acid hydrochloride Following the procedures for Example 22, Step D, the decahydroisoquinoline derivative from step C (10 mg, 0.021 mmol) gave an off-white solid (4 mg, 47% yield).

$^1$H NMR (CD$_3$OD, 200.15 MHz): 7.84 (br s, 1H); 7.48 (br s, 2H); 4.01 (br d, J=12 Hz, 1H); 3.5-3.0 (m, 3H); 2.3-1.7 (m, 8H); 1.5-1.2 (m, 2H). Fast Atom Bombardment Mass Spectrum M-HCl+1: 370

EXAMPLE 27

Preparation of Ethyl(3S, 4aS, 6S, 8aR) 6-((2-ethoxycarbonyl-5-chlorophenyl)thio)-1,2,3,4,4a, 5,6,7,8,8a-decahydroisoquinoline-3-carboxylate hydrochloride

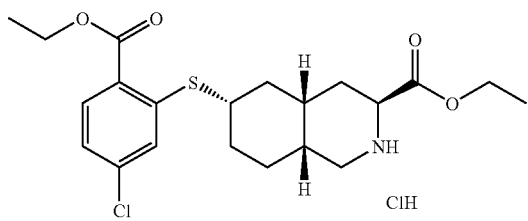

Material from Example 25 (1.78 g, 4.39 mmol) was suspended in saturated hydrogen chloride solution in ethanol (100 mL) and the reaction mixture was heated at reflux overnight. The solvent was concentrated in vacuo. The solid was triturated with ethyl ether and was filtered to afford 1.75 g (86%) of the title compound.

Ion Electrospray Mass Spectrum M-HCl+1: 425

Preparation 4

4-Benzyl-2-fluoro-benzonitrile

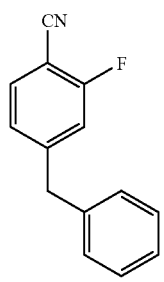

A. Trifluoro-methanesulfonic acid 4-cyano-3-fluoro-phenyl Ester

To a solution of 16.0 g (116.6 mmol) of 2-fluoro-4-hydroxybenzonitrile and 50.0 g (140.0 mmol) of N-phenyltrifluoromethanesulfonimide in 250 mL of dichlorormethane is added N,N-diisopropylethylamine and the mixture is stirred for 16 hr at room temperature. The mixture is then washed with 10% aqueous sodium bisulfate. The organic portion is separated and the aqueous portion is extracted three times with dichlorormethane. The combined organic portions are dried (Na$_2$SO$_4$), filtered and concentrated in vacuo. Chromatography (silica gel, 50% chloroform/hexane) of the residue affords 26.7 g (85%) of the title compound.

Field Desorption Mass Spectrum: M=269.

B. 4-Benzyl-2-fluoro-benzonitrile

To a room temperature solution of 1.5 g (5.57 mmol) of the triflate from Step A above, 0.32 g (6.56 mmol) of bis(dibenzylideneacetone)palladium and 1,1'-bis(diphenylphosphino)-ferrocene in 15 mL of tetrahydrofuran is added to 12.25 mL (6.13 mmol) of a 0.5 M solution of benzylzinc bromide in tetrahydrofuran via syringe. The mixture is heated to 65° C. for 16 hr and cooled to room temperature. The mixture is poured into saturated ammonium chloride and extracted two times with ethyl acetate. The combined organic portions are dried (MgSO$_4$), filtered, and concentrated in vacuo. Chromatography (Biotage, 100% toluene) of the residue affords 0.76 g (65%) of the title compound.

Field Desorption Mass Spectrum: M=211.

EXAMPLE 28

(3S, 4aS, 6S, 8aR) 6-[5-Benzyl-2-(1(2)H-tetrazol-5-yl)-phenoxy]-1,2,3,4,4a, 5,6,7,8,8a-decahydroisoquinoline-3-carboxylic acid hydrochloride

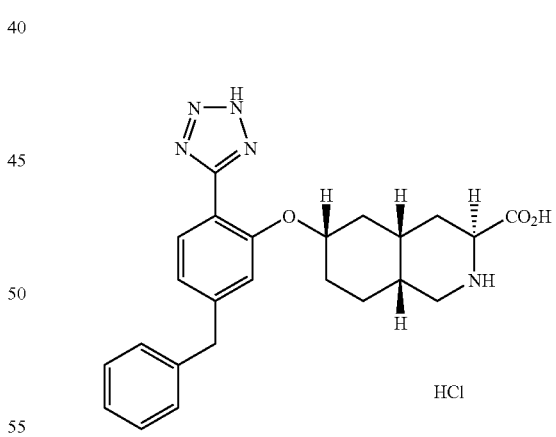

Following the procedures as described in Example 9 using 0.45 g (1.51 mmol) of material from Preparation 2 and 0.32 g (1.51 mmol) of material from Preparation 4 affords 0.13 g (21% overall yield) of the title compound.

Electrospray Mass Spectrum: M+1=434.

Preparation 5

2-Fluoro-4-thiophen-2-yl-benzonitrile

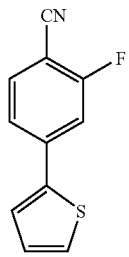

To a degassed solution of 2.5 g (9.3 mmol) of the triflate from Preparation 4, Step A above, 1.3 g (10.4 mmol) thiophene and 1.4 g (10.4 mmol) of potassium carbonate in 24 mL of toluene is added to 0.4 g (0.37 mmol) of tetras (triphenylphosphine) palladium(0). The mixture is heated to 90° C. for 5.5 hr and cooled to room temperature. The mixture is then diluted with ethyl acetate and washed with water. The organic portion is separated and the aqueous portion is extracted two times with ethyl acetate. The combined organic portions are dried over $MgSO_4$, filtered, and concentrated in vacuo. Chromatography (silica gel, 10% ethyl acetate/hexane) of the residue affords 1.2 g (79%) of the title compound.

Field Desorption Mass Spectrum: M=203.

EXAMPLE 29

(3S, 4aS, 6S, 8aR) 6-[5-(2-thienyl)-2-(1(2)H-tetrazol-5-yl)-phenoxy]-1,2,3,4,4a, 5,6,7,8,8a-decahydroisoquinoline-3-carboxylic acid hydrochloride

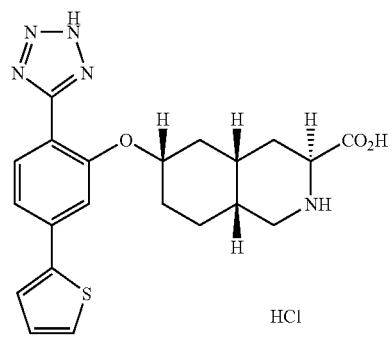

A. (3S, 4aS, 6S, 8aR) 6-[5-(2-thienyl)-2-cyano]-phenoxy-2-methoxycarbonyl-1,2,3,4,4a,5,6,7,8,8,a-decahydroisoquinoline-3-carboxilic acid Following the procedures as described in Step A of Example 9, using 1.0 g (3.9 mmol) of (3S, 4aR, 6S, 8aR) 6-hydroxy-2-methoxycarbonyl-1,2,3,4,4a,5,6,7,8,8a-decahydroisoquinoline-3-carboxilic acid (prepared as described in U.S. Pat. Nos. 4,902,695, 5,446,051, and 5,356, 902) and a 0.8 g (3.9 mmol) of material from Preparation 5, affords 0.84 g (49%) of the title compound.

Electrospray Mass Spectrum: $M+NH_4^+$=458.

B. (3S, 4aS, 6S, 8aR) 6-[5-(2-thienyl)-2-(1(2)H-tetrazol-5-yl)-phenoxy]-2-methoxycarbonyl-1,2,3,4,4a,5,6,7,8,8a-decahydroisoquinoline-3-carboxylic acid A solution of 0.84 g (1.9 mmol) of material from Part A and 1.6 g (4.8 mmol) of azidotributyltin, in just enough tetrahydrofuran to dissolve the nitrile, is heated to 95° C. for 48 hr and the tetrahydrofuran is allowed to evaporate from the mixture. The mixture is cooled to room temperature and 8 mL of methanol is added. To this mixture is added 0.8 mL of 5 N sodium hydroxide and the mixture is stirred for 1.5 hr. The mixture is concentrated in vacuo and partitioned between water and diethyl ether. The organic portion is separated and the aqueous portion is washed once with diethyl ether. The aqueous portion is acidified (pH2) with 10% aqueous sodium bisulfate and extracted four times with ethyl acetate. The combined organic portions are dried ($MgSO_4$), filtered, and concentrated in vacuo. The resulting solid is suspended in ethyl acetate and stirred for 16 hr. The suspension is filtered and dried in vacuo to afford 0.57 g (62%) of the title compound.

Electrospray Mass Spectrum: M+1=484.

C. (3S, 4aS, 6S, 8aR) 6-[5-(2-thienyl)-2-(1(2)H-tetrazol-5-yl)-phenoxy]-1,2,3,4,4a, 5,6,7,8,8a-decahydroisoquinoline-3-carboxylic acid hydrochloride To a suspension of 0.56 g (1.32 mmol) of material from Part B in 8 mL of chloroform is added 0.75 mL (5.28 mmol) of iodotrimethylsilane. The mixture is stirred for 3 hr and 0.19 mL (1.32 mmol) more of iodotrimethylsilane is added. The mixture is stirred for 16 hr more and concentrated in vacuo. Water is added and the mixture is concentrated in vacuo two times. The resulting solid is suspended in water, filtered, and rinsed with acetone then diethyl ether. A precipitate forms in the filtrate and is filtered and dried in vacuo. The solids are combined, suspended in 10 mL of 5 N hydrochloric acid, and stirred for 16 hr. The suspension is filtered and rinsed with water, acetone, and then diethyl ether. The solid is dried in vacuo to afford 0.13 g (21%) of the title compound.

Electrospray Mass Spectrum: M+1=426.

Preparation 6

3,2'-Difluoro-biphenyl-4-carbonitrile

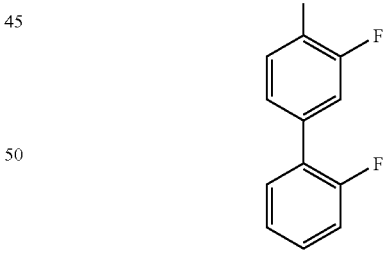

The material from Preparation 4, Step A (2.5 gm, 9.3 mmol), 2-Fluorophenylboronic acid (1.82 gm, 13.0 mmol), and powdered potassium carbonate (1.93 gm, 13.9 mmol) are combined with toluene (25 mL). The solution is stirred under a nitrogen atmosphere and degassed. Tetrakis(triphenylphosphine)palladium(0) (1.07 gm, 0.93 mmol) is added with a toluene rinse (5 mL), and the solution is degassed and heated at 90° C. overnight. The reaction is diluted with ethyl acetate and washed with distilled water (2×). The separated aqueous layer is back extracted with ethyl acetate (3×). The combined organics are dried (magnesium sulfate), filtered, and concentrated to give crude oil (3.14 gm). Chromatography (0 to 50%

EXAMPLE 30

(3S, 4aR, 6S, 8aR) 6-[2'-Fluoro-(2H-tetrazol-5-yl)-biphenyl-3-yloxy]-1,2,3,4,4a, 5,6,7,8,8a-decahydroisoquinoline-3-carboxylic acid hydrochloride

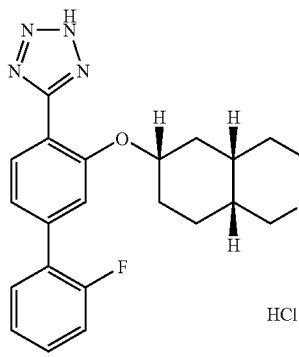

A. (3S, 4aR, 6S, 8aR) 6-(4-Cyano-2'-fluoro-biphenyl-3-yloxy)-1,2,3,4,4a, 5,6,7,8,8a-decahydroisoquinoline-2,3-dicarboxylic acid 2-tert-butyl ester The material from Preparation 6 (0.36 gm, 1.67 mmol) is added to a 0° C. solution of material from Preparation 2 (0.50 gm, 1.67 mmol) and potassium tert-butoxide (1.0 M in tetrahydrofuran, 5.01 mL) in anhydrous tetrahydrofuran (6 nL), after the solution is stirred at 0° C. for 20 minutes. The reaction is stirred for 24 hrs at room temperature, and potassium tert-butoxide (1.0 M in tetrahydrofuran, 0.84 mL) is added at 0° C. The reaciton is then stirred at room temperature for a few hours, and then diluted with aqueous sodium bisulfate (10% aq). The separated aqueous layer is extracted with ethyl acetate (3×). The combined organics are dried (magnesium sulfate), filtered, and concentrated in vacuo to give crude material (1.10 gm). Chromatography (0-30% ethyl acetate in hexane with 2% acetic acid) gives the title product: 0.37 gm (45%). MS (m/z, ES+): 495.2.

B. (3S, 4aR, 6S, 8aR) 6-[2'-Fluoro-4-(2H-tetrazol-5-yl)-biphenyl-3-yloxy]-1,2,3,4,4a, 5,6,7,8,8a-decahydroisoquinoline-3-carboxylic acid hydrochloride To a solution of material from Step A (0.34 gm, 0.69 mmol) in anhydrous tetrahydrofuran (0.8 mL) is added azidotributyltin (0.68 gm, 2.05 mmol). The reaction is stirred under nitrogen at 95° C. for 3 days. The reaction is diluted in a small volume of dichloromethane and chromatographed (40% ethyl acetate in hexane containing 3% acetic acid to give the desired product.

C. (3S, 4aR, 6S, 8aR) 6-[2'-Fluoro-4-(2-H-tetrazol-5-yl)-biphenyl-3-yloxy]-1,2,3,4,4a, 5,6,7,8,8a-decahydroisoquinoline-3-carboxylic acid hydrochloride To a solution of material from Step B in ethyl acetate (3.5 mL) is added a solution of hydrogen chloride (2 M in ethyl acetate, 3.5 mL). The reaction is stirred at room temperature under nitrogen overnight. The precipitated solid is filtered, washed with ethyl acetate (2×) and then with diethyl ether (2×), and dried in a vacuum oven to give final product: 0.179 gm (55% combined Steps B&C yield). MS (m/z, ES+): 438.2.

EXAMPLE 31

(3S, 4aR, 6S, 8aR) 6-[4'-Methyl-4-(2H-tetrazol-5-yl)-biphenyl-3-yloxy]-1,2,3,4,4a, 5,6,7,8,8a-decahydroisoquinoline-3-carboxylic acid hydrochloride Following the procedures as described in Preparation 6 and Example 30,

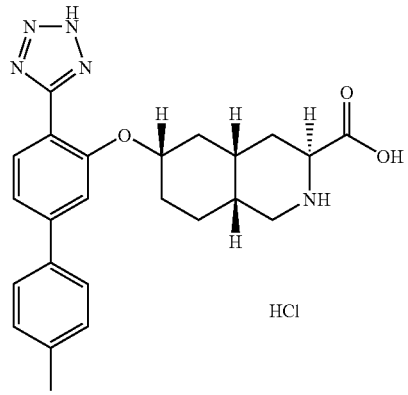

above, and using Trifluoro-methanesulfonic acid 4-cyano-3-fluoro-phenyl ester (0.64 gm, 2.37 mmol) and 4-Methylphenylboronic acid (0.45 gm, 3.33 mmol) affords 0.301 gm (38% overall yield) of the title compound. MS (m/z, ES+): 434.2.

EXAMPLE 32

(3S, 4aR, 6S, 8aR) 6-[5-Naphthalen-2-yl-2-(2H-tetrazol-5-yl)-phenoxy]-1,2,3,4,4a, 5,6,7,8,8a-decahydroisoquinoline-3-carboxylic acid hydrochloride

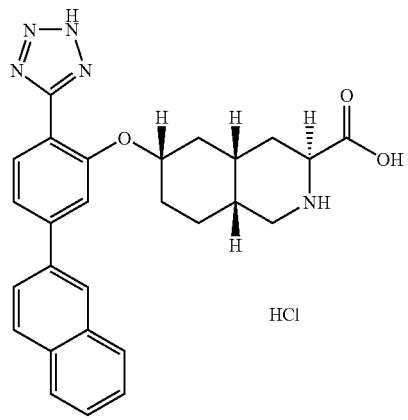

Following the procedures as described in Preparation 6 and Example 30, above, and using Trifluoro-methanesulfonic acid 4-cyano-3-fluoro-phenyl ester (0.55 gm, 2.04 mmol) and 2-Naphthaleneboronic acid (0.49 gm, 2.86 mmol) affords 0.069 μm (6.6% overall yield) of the title compound. MS (m/z, ES+): 470.3

EXAMPLE 33

(3S, 4aR, 6S, 8aR) 6-[2'-Methoxy-4-(2H-tetrazol-5-yl)-biphenyl-3-yloxy]-1,2,3,4,4a,5,6,7,8,8a-decahydroisoquinoline-3-carboxylic acid hydrochloride

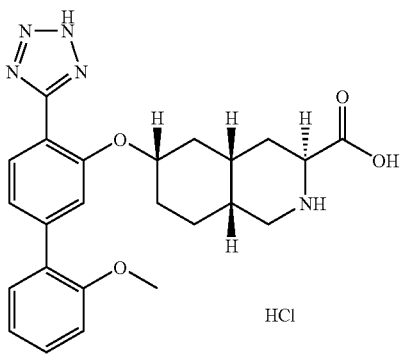

Following the procedures as described in Preparation 6 and Example 30, Step A, above, and using Trifluoro-methanesulfonic acid 4-cyano-3-fluoro-phenyl ester (0.59 gm, 2.2 mmol) and 2-Methoxyphenylboronic acid (0.47 gm, 3.1 mmol) affords 0.41 gm (45% yield) of the N-boc protected title compound. MS (m/z, ES+): 470.3 The final title product is isolated by the procedures described in Example 30, Step B. MS (m/z, ES+): 450.2

Preparation 7

2-Hydroxy-4-pyrazol-yl-benzonitrile

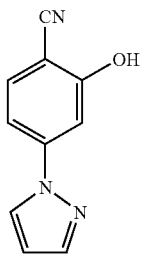

A. Preparation of 2-Benzyloxy-4-fluoro-benzonitrile

To 2.5 mL benzyl alcohol in 80 mL THF is added 1.87 g NaH. After one hour stirring at room temperature, 5.0 g of 2,4-Difluorobenzonitrile is added. After stirring one hour, the reaction is quenched with excess water and concentrated in vacuo. The residue is redissolved in ethyl acetate and washed with water, brine, dried over sodium sulfate, filtered and concentrated in vacuo. The product is recrystallizde in carbon tetrachloride to give 3.24 g (39.7%) of the title compound.

$^1$H NMR (400 MHz, CDCl$_3$) δ 7.6-7.55 (dd, 1H), 7.5-7.32 (m, 5H), 6.78-6.7 (m, 2H), 5.2 (s, 2H).

B. Preparation of 2-Benzyloxy-4-pyrazol-1-yl-benzonitrile

To 0.180 g pyrazole in 5 mL DMF is added 0.105 g NaH. After stirring 50 minutes at room temperature, 0.200 g of the material from Step A, above, is added all at once with 5 mL DMP. After 2 hours at room temperature, the reaction is quenched with water and Concentrated in vacuo. The residue is redissolved in ethyl acetate and washed with water, brine, dried over sodium sulfate, filtered and concentrated in vacuo. Flash chromatography eluting with toluene provides 0.181 g (74.8%) of the title compound.

$^1$H NMR (400 MHz, CDCl$_3$) δ 7.92 (s, 1H), 7.75 (s, 1H), 7.67-7.65 (d, 1H), 7.6 (s, 1H), 7.52-7.47 (d, 2H), 7.45-7.4 (t, 2H), 7.4-7.34 (d, 1H), 7.25-7.2 (d, 1H), 6.55 (s, 1H), 5.3 (s, 2H).

C. Preparation of 2-Hydroxy-4-pyrazol-1-yl-benzonitrile

To 0.395 g of the material from Step B, above, dissolved in 10 mL THF, is added a catalytic amount of 10% Pd/C and excess ammonium formate. The reaction is heated to 50° C. for 45 minutes. Upon cooling, celite is added. The reaction is then gravity filtered and concentrated in vacuo. The residue is redissolved in ethyl acetate and washed with water, brine, dried over sodium sulfate, filtered and concentrated in vacuo to give 0.152 g of the final title compound (57.1%).

$^1$H NMR (400 MHz, DMSO-d) δ 8.35 (s, 1H), 7.75 (s, 1H), 7.61-7.59 (d, 1H), 7.4 (s, 1H), 7.35-7.3 (d, 1H), 6.55 (s, 1H).

EXAMPLE 34

(3S, 4aS, 6S, 8aR) 6-[5-Pyrazol-1-yl-2-(2H-tetrazol-5-yl)-phenoxy]-1,2,3,4,4a,5,6,7,8,8a-decahydroisoquinoline-3-carboxylic acid hydrochloride

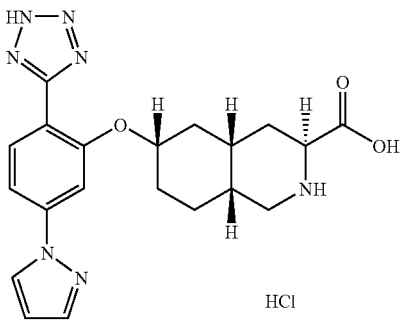

A. Preparation of (3S, 4,8aR) 6-8aR-(2-Cyan(5-pyrazol-1-yl-phenoxy)-1,2,3,4,4a, 5,6,7,8,8a-decahydroisoquinoline-2,3-dicarboxylic acid 2-tert-butyl ester 3-ethyl ester To 0.145 g of the material from Preparation 7, 0.256 g of Ethyl (3S, 4aS, 6S, 8aR) 6-hydroxy-2-tert-butoxycarbonyl-1,2,3,4,4a, 5,6,7,8,8a-decahydroisoquinoline-3-carboxylate (prepared essentially as described in Preparation 1), and 0.308 g triphenylphosphine are added to 0.18 mL diethylazodicarboxylate. After stirring at room temperature overnight, the reaction is concentrated in vacuo. Flash chromatography eluting with a stepwise gradient from 5-25% Ethyl acetate/toluene provides 0.226 g of the title compound (58.4% yield).

$^1$H NMR (400 MHz, CDCl$_3$) δ 7.9 (m, 1H), 7.8 (m, 1H), 7.7-7.6 (dd, 1H), 7.4 (m, 1H), 7.25-7.18 (m, 1H), 7.18-7.1 (d, 1H), 6.5-6.4 (m, 1H), 4.95-4.65 (m, 2H), 4.2-4.05 (m, 2H), 3.9-3.7 (m, 1H), 3.25-3.0 (m, 1H), 2.75-2.5 (m, 1H), 2.17-2.07 (d, 1H), 2.07-1.9 (m, 3H), 1.9-1.75 (m, 2H), 1.75-1.55 (m, 2H), 1.45-1.3 (m, 9H), 1.3-1.15 (m, 3H). MS m/z: 395.3 (m$^+$-99).

B. (3S, 4aR, 6S, 8aR) 6-[5-Pyrazol-1-yl-2-(2H-tetrazol-5-yl)-phenoxy]-1,2,3,4,4a, 5,6,7,8,8a-decahydroisoquinoline-2,3-dicarboxylic acid 2-tert-butyl ester 3 ethyl ester To 0.220 g of the material from Step A, above, is added 0.5 mL azidotributyltin and 0.5 mL toluene. The reaction is heated to 90° C. for two days. The residue is dissolved in ethyl acetate and washed with water, brine, dried over sodium sulfate, filtered and concentrated in vacuo. Flash chromatography eluting with 2% MeOH/CHCl₃ provides 0.142 g of the title compound (59.4% yield).

¹H NMR (400 MHz, d-MeOH) δ 8.35 (s, 1H), 7.81-7.79 (d, 1H), 7.73 (s, 1H), 7.61 (s, 1H), 7.5-7.46 (d, 1H), 6.55 (s, 1H), 4.95-4.89 (bm, 1H), 4.45-4.29 (bm, 1H), 4.15-4.03 (q, 2H), 3.75-3.65 (d, 1H), 3.1-2.9 (bm, 1H), 2.25-2.15 (d, 1H), 2.0-1.92 (d, 1H), 1.85-1.53 (m, 6H), 1.43 (s, 9H), 1.38-1.1 (m, 4H), 0.92-0.84 (t, 1H).

C. (3S, 4aS, 6S, 8aR) 6-[5-Pyrazol-1-yl-2-(2H-tetrazol-5-yl)-phenoxy]-1,2,3,4,4a, 5,6,7,8,8a-decahydroisoquinoline-2,3-dicarboxylic acid 2-tert-butyl ester To 0.129 g of the material from Step B, above, dissolved in 10 mL MeOH is added 0.72 mL 1N NaOH. The reaction is heated to 50° C. overnight. 0.72 mL 1N NaOH is then added and heated for four more hours. Upon completion, the reaction is concentrated in vacuo, redissolved in water and acidified to pH 3, extracted with ethyl acetate, washed with brine, dried over sodium sulfate, filtered and concentrated in vacuo. Flash chromatography eluting with 10% MeOH/CHCl₃ provides 0.040 g of the title compound (32.8% yield), which is used directly in the following step.

D. (3S, 4aR, 6S, 8aR) 6-[5-Pyrazol-1-yl-2-(2H-tetrazol-5-yl)-phenoxy]-1,2,3,4,4a, 5,6,7,8,8a-decahydroisoquinoline-3-carboxylic acid hydrochloride To 0.040 g of the material from Step C, above, dissolved in 5 mL CH₂Cl₂, is added 3 mL 2M HCl in diethyl ether. After stirring four hours at ambient temperature, the reaction is concentrated in vacuo.

¹H NMR (400 d-MeOH) δ 8.4 (s, 1H), 8.06-8.04 (d, 1H), 7.78 (s, 1H), 7.72 (s, 1H), 7.52-7.49 (d, 1H), 6.58 (s, 1H), 4.75-4.65 (1 μm, 1H—), 4.05-3.96 (d, 1H), 3.16-3.08 (dd, 1H), 2.33-1.88 (m, 10H), 1.66-1.5 (m, 1H). MS m/z: 410.2 (m⁺+1).

Preparation 8

2-Hydroxy-4-indol-yl-benzonitrile

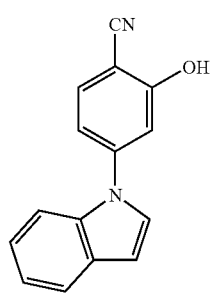

A. Preparation of 2-Benzyloxy-4-indol-1-yl-benzonitrile

Using indole, the title compound is prepared according to the procedures described in Preparation 7, step B and provides 0.39 g (91.1% yield).

¹H NMR (400 MHz, CDCl₃) δ 7.73-7.63 (m, 2H), 7.6-7.37 (m, 5H), 7.3-7.07 (m, 6H), 6.71-6.68 (d, 1H, 5.3 (s, 2H).

B. Preparation of 2-Hydroxy-4-indol-1-yl-benzonitrile

Using the material from Step A, above, the title compound is prepared according to the procedures described in Preparation 7, step C and provides .188 g (66.7% yield).

¹H NMR (400 z, CDCl₃) δ 7.65-7.54 (m, 3H), 7.27-7.1 (m, 5H), 6.67 (d, 1H).

EXAMPLE 35

(3S, 4aS, 6S, 8aR) 6-[5-indol-1-yl-2-(2H-tetrazol-5-yl)-phenoxy]-1,2,3,4,4a, 5,6,7,8,8a-decahydroisoquinoline-3-carboxylic acid

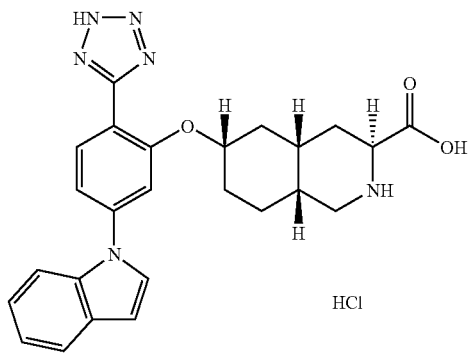

A. (3S, 4aS, 6S, 8aR) 6-(2-Cyano-5-indol-1-yl-phenoxy)-1, 2,3,4,4a, 5,6,7,8,8a-decahydroisoquinoline-2,3-dicarboxylic acid 2-tert-butyl ester 3-ethyl ester Using the material from Preparation 8, above, the title compound is prepared according to the procedures described in Example 34, step A and provides 0.233 g (53.4% yield).

MS m/z: 444.3 (m⁺–99).

B. (3S, 4aS, 6S, 8aR) 6-[5-indol-1-yl-2-(2H-tetrazol-5-yl)-phenoxy]-1,2,3,4,4a, 5,6,7,8,8a-decahydroisoquinoline-2,3-dicarboxylic acid 2-tert-butyl ester 3-ethyl ester Using the material from Step A, above, the title compound is prepared according to the procedures described in Example 34, step B and provides 0.19 g (76% yield).

MS m/z: 585.2 (M⁻–1).

C. (3S, 4aS, 6S, 8aR) 6-[5-indol-1-yl-2-(2H-tetrazol-5-yl)-phenoxy]-1,2,3,4,4a, 5,6,7,8,8a-decahydroisoquinoline-2,3-dicarboxylic acid 2-tert-butyl ester Using the material from Step B, above, the title compound was prepared according to the procedures described in Example 34, step C and provides 0.100 g (58.5% yield).

MS m/z: 557.3 (M⁻–1).

D. (3S, 4aS, 6S, 8aR) 6-[5-indol-1-yl-2-(2H-tetrazol-5-yl)-phenoxy]-1,2,3,4,4a, 5,6,7,8,8a-decahydroisoquinoline-3-carboxylic acid Using the material from Step C, above, the title compound is prepared according to the procedures described in Example 34, step D and provides 0.078 g (92.9% yield).

¹H NMR (400 MHz,d-MeOH) δ 8.14-8.11 (d, 1H), 7.64-7.6 (d, 2H), 7.55 (s, 1H), 7.43 (s, 1H), 7.37-7.35 (d, 1H), 7.22-7.18 (t, 1H), 7.15-7.1 (t, 1H), 6.7 (s, 1H), 4.74-4.64 (m, 1H), 4.03-4.0 (d, 1H), 3.37-3.3 (t, 1H), 3.15-3.1 (dd, 1H), 2.18-1.93 (m, 5H), 1.85-1.68 (m, 3H), 1.68-1.55 (m, 2H). MS m/z: 459.2 (m⁺+1).

Preparation 9

2-Hydroxy-4-pyrrol-1-yl-benzonitrile

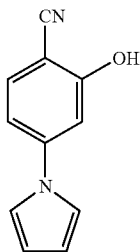

A. Preparation of 2-Benzyloxy-4-pyrrol-1-yl-b benzonitrile

Using pyrrole, the title compound is prepared according to the procedures described in Preparation 7, step B and provides 0.457 g (94.6% yield).

$^1$H NMR (400 MHz, CDCl$_3$) δ 7.57-7.56 (d, 1H), 7.6-7.44 (d, 2H), 74-7.35 (t, 2H), 7.34-7.3 (d, 1H), 7.01-6.98 (m, 3H), 6.94 (s, 1H), 6.34 (s, 2H), 5.23 (s, 2H).

B. Preparation of 2-Hydroxy-4-pyrrol-1-yl-benzonitrile

Using the material from Step A, above, the title compound is prepared according to the procedures described in Preparation 7, step C and provides .213 g (70.5% yield).

$^1$H NMR (400 z, d-MeOH) δ 7.54-7.51 (d, 1H), 7.7 (s, 2H), 7.05-7.02 (d, 1H), 6.96 (s, 1H), 6.28 (s, 2H).

EXAMPLE 36

(3S, 4aS, 6S, 8aR) 6-[5-Pyrrol-1-yl-2-(2H-tetrazol-5-yl)-phenoxy]-1,2,3,4,4a, 5,6,7,8,8a-decahydroisoquinoline-3-carboxylic acid hydrochloride

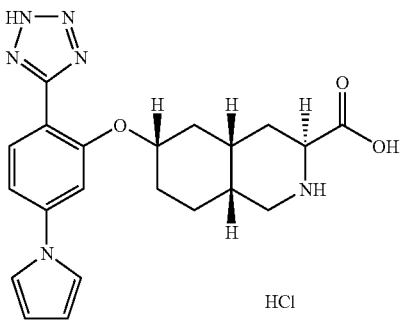

A. (3S, 4aS, 6S, 8aR) 6-(2-Cyano-5-pyrrol-1-yl-phenoxy)-1, 2,3,4,4a, 5,6,7,8,8a -decahydroisoquinoline-2,3-dicarboxylic acid 2-tert-butyl ester 3-ethyl ester Using the material from Preparation 9, above, the title compound is prepared according to the procedures described in Example 34, step A and provides 0.216 g (38% yield).

MS m/z: 394.2 (M$^+$–99).

B. (3S, 4aS, 6S, 8aR) 6-[5-Pyrrol-1-yl-2-(2H-tetrazol-5-yl)-phenoxy]-1,2,3,4,4a,5,6,7,8,8a-decahydroisoquinoline-2, 3-dicarboxylic acid 2-tert-butyl ester 3-ethyl ester Using the material from Step A, above, the title compound is prepared according to the procedures described in Example 34, step B and provides 0.074 g (35% yield) which is used directly in the following step.

C. (3S, 4aS, 6S, 8aR) 6-[5-Pyrrol-1-yl-2-(2H-tetrazol-5-yl)-phenoxy]-1,2,3,4,4a, 5,6,7,8,8a-decahydroisoquinoline-2, 3-dicarboxylic acid 2-tert-butyl ester Using the material from Step B, above, the title compound is prepared according to the procedures described in Example 34, step C and provides .014 g, (22.6% yield) which is used directly in the following step.

D. (3S, 4aS, 6S, 8aR) 6-[5-Pyrrol-1-yl-2-(2H-tetrazol-5-yl)-phenoxy]-1,2,3,4,4a, 5,6,7,8,8a-decahydroisoquinoline-3-carboxylic acid hydrochloride Using the material from Step C, above, the title compound is prepared according to the procedures described in Example 34, step D. and provides 0.012 g (97.5% yield).

$^1$H NMR (400 MHz, d-MeOH) δ 8.0-7.98 (d, 1H), 7.35-7.3 (d, 3H), 7.3-7.24 (d, 1H), 6.32 (s, 2H), 4.78-4.69 (m, 1H), 4.0-3.96 (dd, 1H), 3.37-3.3 (t, 1H), 3.14-3.08 (dd, 1H), 2.33-2.25 (m, 1H), 2.2-1.74 (m, 7H), 1.64-1.5 (m, 1H), 1.26 (s, 1H). MS m/z: 409.3 M$^+$+1), 407.3 (M$^-$–1).

Preparation 10

(3S, 4aS, 6S, 8aR) 6-hydroxy-2-methoxycarbonyl-1,2,3,4,4a, 5,6,7,8,8a -decahydroisoquinoline-3-carboxylic acid

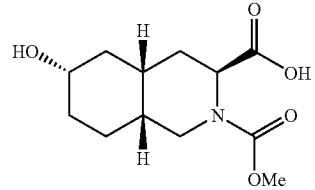

To a slurry of 17.3 g of (3S, 4aR, 8aR) 6-oxo-2-methoxycarbonyl-1,2,3,4,4a, 5,6,7,8,8a-decahydroisoquinoline-3-carboxylic acid (46 mmol) in 240 mL of tetrahydrofuran is added 106 mL if 1.0 M L-Selectride in tetrahydrofuran. The mixture is stirred for 1 hour at room temperature, then quenched with 130 mL of 1.4 M hydrochloric acid. The layers are separated and the aqueous phase extracted with 50 mL of tert-butyl methyl ether. The organic phases are combined and extracted with 75 mL of saturated aqueous sodium carbonate. The aqueous phase is washed twice with 30 mL portions of tert-butyl methyl ether then acidified to pH 1 with 6 M hydrochloric acid. The product is extracted into 75 mL of tert-butyl methyl ether. The organic mixture is dried with sodium sulfate, and concentrated to 8.17 g of yellow solid. The product is crystallized from 20 mL of tert-butyl methyl ether to provide 6.92 g of the title compound (59% yield).

Preparation 11

6-Chloro-2-fluoro-benzotetrazole

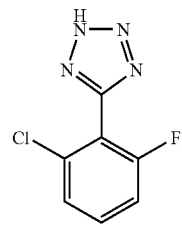

To a 12 L round bottomed flask under nitrogen was added trimethyl aluminum (1930 mL of a 2M solution in toluene, 3.86 mol). The flask is cooled to −7° C. before adding azidotrimethylsilane (512.5 mL, 3.86 mol) via canula such that the internal temperature is maintained at less than 3° C. To this flask is added 6-chloro-2-fluorobenzonitrile (500 g, 3.21 mol) dropwise as a solution in toluene (1 L). The reaction is slowly warmed to room temperature then heated to 90° C. A cold finger is used to condense tetramethylsilane as it boiled from the reaction mixture. The reaction is heated at 90° C. for 13 hours before cooling to room temperature. The reaction is cooed to 0° C. with an ice bath then transferred slowly via cannula to a pre-cooled (−5° C.) solution of 6N aqueous HCl (3 L) and ethyl acetate (3 L). The internal temperature during the quench is kept at less than 5° C. After addition, the flask is allowed to warm to room temperature. The reaction is diluted with ethyl acetate (2 L) to disolve solids before tranferring to a 22 L flask. The layers are separated and the aqueous layer was extracted with ethyl acetate (1 L). The combined organic layers are washed with brine (2 L), dried over anhydrous sodium sulfate, and concentrated. 636.4 g. of the title compound is obtained (93% yield). Analysis by HPLC and $^1$H NMR analysis shows the purity as greater than 98%.

Preparation 12

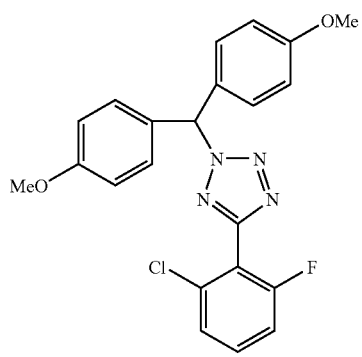

To a thick slurry of the material from Preparation 11, above, (101.8 g, 0.513 mol) and 4,4'-dimethoxybezhydrol (125 g, 0.513 mol) in 510 mL glacial acetic acid is added concentrated sulfuric acid (5.5 mL). Upon addition, the reaction immediately becomes red and homogeneous. The red color rapidly lightens to orange over several minutes. An endotherm of 3-4° C. is also observed as the reaction becomes homogeneous. After approximately 15 minutes, the product begins to crystallize from the reaction mixture resulting in a mild exotherm (<10° C.). After 1 hour, the solid is isolated by filtration and washed with water (1 L) then isopropyl alcohol (0.5 L). The resulting white solid is dried in vacuo at 50° C. to afford 199.8 g of the title compound (91% yield).

EXAMPLE 37

2-Ethyl-butyl (3S, 4aS, 6S, 8aR) 6-[3-chloro-2-(1(2)H-tetrazol-5-yl)-phenoxy]-1,2,3,4,4a,5,6,7,8,8a-decahydroisoquinoline-3-carboxylate para-toluenesulfonate

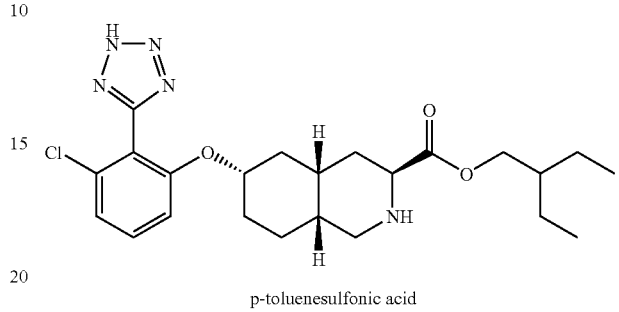

p-toluenesulfonic acid

A. Preparation of

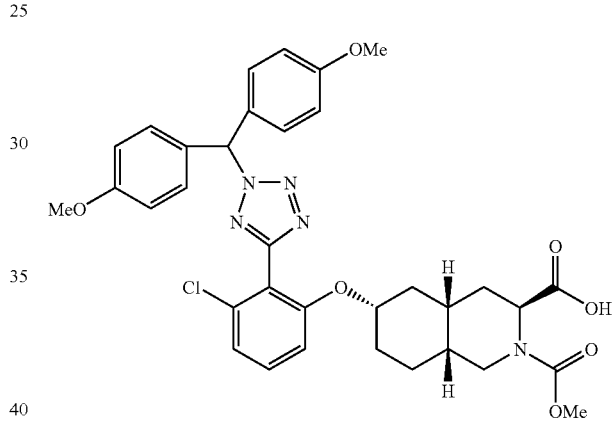

To a slurry of sodium hydride (60% dispersion in mineral oil, 2.94 g, 73.5 mmol) in dry dimethyl sulfoxide (25 mL) is added the material from Preparation 10 (9.44 g, 36.7 mmol) dropwise as a solution in dimethyl sulfoxide (21 mL). During the course of the addition (40 min.), a cooling bath is used to maintain the temperature at or below 25° C. After stirring 15 minutes at ambient temperature, the material from Preparation 12 (10.4 g, 24.5 mmol) is added in one portion as a solid. The slurry is stirred at room temperature for 20 minutes before heating to 40° C. for 2.75 hours. Analysis of the reaction mixture by HPLC shows no additional progress after this point and the reaction is cooled to room temperature. The reaction is quenched by addition of 1N aqueous hydrogen chloride solution (50 mL), water (200 mL) and ethyl actetate (200 mL). The layers are separated and the aqueous layer is extracted with ethyl acetate (1×50 mL). The combined organic layers are washed with water (2×100 mL) and 10% aqueous sodium chloride solution (1×10 mL). The organic layer is then dried over anhydrous sodium sulfate and concentrated in vacuo to afford a crude oil. The crude product is purified on silica gel eluting 1% methanol in methylene chloride followed by 5% methanol in methylene chloride to afford 11.84 g. of the title compound (73% yield) as a white foam.

B. Preparation of

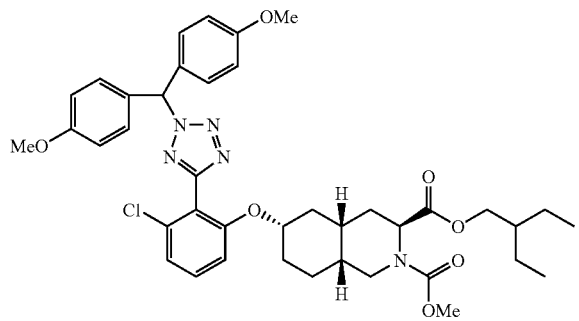

To a solution material from Step A, of the above (16.87 g, 25.4 mmol), in N,N-dimethylformamide (170 mL) is added powder potassium carbonate (4.55 g, 33 mmol) and 3-(bromomethyl)pentane (4.62 mL, 33 mmol). The reaction mixture is heated to 80° C. under nitrogen. After 1 h, analysis by thin layer chromatography and HPLC indicates that the reaction was complete. The reaction is cooled and diluted with water (500 mL) and methylene chloride (170 mL). The organic layer is washed with brine, dried over anhydrous magnesium sulfate, and concentrated in vacuo to afford 17.8 g. of the title compound (94% yield) as a foam.

C. 2-Ethyl-butyl (3S, 4aS, 6S, 8aR) 6-[3-chloro-2-(1 (2)H-tetrazol-5-yl)-phenoxy]-2-methoxycarbonyl-1, 2,3,4,4a,5,6,7,8,8a-decahydroisoquinoline-3-carboxylate To a solution of the material from Step B, above (216 g, 289 mmol), is added anisole (94.4 mL, 868.3 mmol) and trifluoroacetic acid (564 mL). The dark red solution is stirred at RT until complete conversion is observed by HPLC (6.5 h). The reaction is concentrated to a dark red oil. The residual trifluoroacetic acid is removed by azeotropic distillation with chloroform. The resulting oil is dissolved in methylene chloride (800 mL) and washed with pH 4 buffer (4×1 L). The organic layer is dried over anhydrous magnesium sulfate, filtered, and concentrated to a crude oil. The product is purified on silica gel (2 Kg) eluting methylene chloride, 10% ethyl acetate in methylene chloride, then ethyl acetate. The appropriate fractions are concentrated in vacuo to provide 132 g. of the title compound as a white foam (88% yield).

D. 2-Ethyl-butyl (3S, 4aS, 6S, 8aR) 6-[3-chloro-2-(1 (2)H-tetrazol-5-yl)-phenoxy]-1,2,3,4,4a,5,6,7,8,8a-decahydroisoquinoline-3-carboxylate The material from Step C, above (390 g, 750 mmol) and 187 mL of trimethylsilyliodide are combined in 1.65 L of dichloromethane and the mixture stirred at ambient temperature for 24 hours. At this time the mixture is quenched with 10 mL of saturated aqueous sodium hydrogencarbonate and combined with 325 mL of tetrahydrofuran. The reaction is further quenched with a total of 2.0 L of saturated aqueous sodium hydrogencarbonate. The mixture is stirred for 1 hour and the product is isolated by filtration. The solids are washed with water and dichloromethane then dried in vacuo to provide 230 g of the title compound.

The isolated solids are further purified by recrystallization. A mixture of 245 g of the title compound is combined with 2.0 L of water and 200 mL of acetonitrile. The mixture is adjusted to pH 6.8 by the addition of 1.0 M hydrochloric acid. An additional 1.0 L of acetonitrile is added and the mixture is heated to effect a solution. The solution is allowed to cool to ambient temperature producing a precipitate. After the mixture cools to approximately 25° C. for 20 minutes the solids are collected by filtration. The solids are washed with water and dried in vacuo to provide 211 g of the title compound.

E. 2-Ethyl-butyl (3S, 4aS, 6S, 8aR) 6-[3-chloro-2-(1 (2)H-tetrazol-5-yl)phenoxy]-1,2,3,4,4a,5,6,7,8,8a-decahydroisoquinoline-3-carboxylate para-toluenesulfonate To a suspension of the material from Step D, above (211 g, 457 mmol) in 1100 mL of 2-propanol, is added p-toluenesulfonic acid monohydrate (91.7 g, 480 mmol). The mixture is heated to 55° C. to effect a solution then allowed to cool to ambient temperature for 2 hours and then further cooled to approximately 3° C. for 90 minutes. The solids are collected by filtration and washed with 500 mL of cold 2-propanol. The solids are dried in vacuo to provide 270 g (93% yield) of the final title compound as a white powder.

$^1$H NMR, 500 MHz dmso-d6, 9.23 (bs, 1H), 8.94 (bs, 1H), 7.56 (t, 1H), 7.45 (d, 2H), 7.30 (d, 1H), 7.24 (d, 1H), 7.09 (d, 2H), 4.37 (m, 1H), 4.17 (m, 1H), 4.13 (dd, 1H), 4.03 (dd, 1H), 3.04 (m, 1H), 2.94 (m, 1H), 2.26 (s, 3H), 2.07 (m, 1H), 1.96 (m, 1H), 1.84 (m, 2H), 1.75 (m, 2H), 1.60 (m, 3H), 1.48 (m, 1H), 1.29 (m, 4H), 1.09 (m, 1H), 0.83 (t, 6H)

Mp=204° C.

EXAMPLE 38

2-Ethyl-butyl (3S, 4aS, 6S, 8aR) 6-[3-chloro-2-(1(2)H-tetrazol-5-yl)-phenoxy]-1,2,3,4,4a,5,6,7,8,8a-decahydroisoquinoline-3-carboxylate para-toluenesulfonate

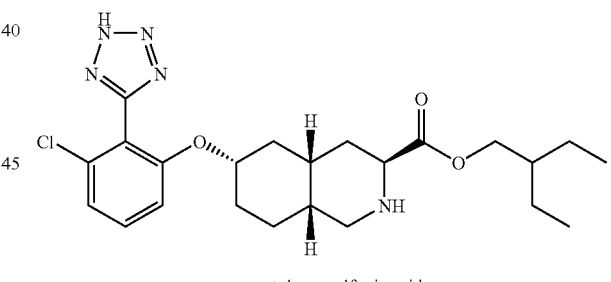

p-toluenesulfonic acid

A. (3S, 4aS, 6S, 8aR) 6-[3-chloro-2-(1(2)H-tetrazol-5-yl)-phenoxy]-2-methoxycarbonyl-1,2,3,4,4a,5,6,7, 8,8a-decahydroisoquinoline-3-carboxylic acid The material from Preparation 10 (20.0 g, 77.7 mmol) is added to 311 mL of 1 M potassium tert-butoxide in tetrahydrofuran followed by the addition of 6-Chloro-2-fluoro benzotetrazole (Preparation 11) (17.0 g, 85.7 mmol). The mixture is heated to 63° C. and monitored for consumption of the aryl tetrazole by HPLC. After 4 hours the reaction is cooled to 20° C. and quenched by the addition of trimethylsilyl chloride (16.9 g, 155.5 mmol). followed by heating to reflux for 30 minutes. The reaction mixture is again cooled to ambient temperature and further quenched by the addition of 224 mL of 1.5 M hydrochloric acid. The organic phase is washed with two 50 mL portions of saturated aqueous sodium chloride. The organic phase is then exchanged for ethyl acetate by atmospheric distillation of the tetrahydrofuran with concurrent addition of ethyl acetate until the distillation temperature reaches 75° C. The exchange of solvents effects the precipitation of the desired product. The mixture is cooled to 10° C. and the solids are collected by filtration, washed with ethyl acetate, and dried to provide 43.4 g of product as a white solid.

B. (3S, 4aS, 6S, 8aR) 6-[3-chloro-2-(1(2)H-tetrazol-5-yl)-phenoxy]-1,2,3,4,4a,5,6,7,8,8a-decahydroisoquinoline-3-carboxylic acid•hydrochloride To a solution prepared from 85% potassium hydroxide (21.2 g 321 mmol) and 100 mL of water is added the material from Step A, above (20.0 g, 45.9 mmol). The solution is heated to 103° C. for 26 hours at which time the HPLC analysis shows less than 4% starting material remains. The reaction is cooled to 30° C. and is added over 20 minutes- to 62 mL of 6 M hydrochloric acid effecting the precipitation of the desired product. The mixture is cooled to 10° C. and the product is collected by filtration, washed with 1 M hydrochloric acid, followed by a wash with acetonitrile. The product is dried in vacuo to provide 17 g of the title compound (89% yield) as a white solid.

The title compound (20.0 g) is then combined with 200 mL of water and heated to 90° C. to effect a solution. The solution is cooled to 60° C. and 40 mL of 6 M hydrochloric acid is added effecting the precipitation of the title compound. The mixture is stirred at 60° C. for 45 minutes then cooled to ambient temperature. The recrystallized hydrate product is collected by filtration and washed with 100 mL of acetonitrile. The product was dried in vacuo to 17 g of 2049266 as a white solid and used in the next step C. 2-Ethyl-butyl (3S, 4aS, 6S, 8aR) 6-[3-chloro-2-(1(2)H-tetrazol-5-yl)-phenoxy]-1,2,3,4,4a,5,6,7,8,8a-decahydroisoquinoline-3-carboxylate para-toluenesulfonate A mixture of the hydrate from Step B, above(30.0 g, 69.4 mmol), para-toluenesulfonic acid monohydrate (15.84 g, 83.3 mmol), 75.0 mL of 2-ethyl-1-butanol, and 6.0 mL of water is heated to 140° C. over a two hour period. During the heating process, a distillate is collected which contains 11 mL of aqueous and 14 mL of organic phases. The mixture is cooled 70° C. and 75 mL of 2-propanol is added. The mixture is further cooled to 50° C. and 150 mL of tert-butyl methyl ether is added over 20 minutes effecting the precipitation of the product. The mixture is then cooled to ambient temperature. The solids are collected by filtration, washed with 50 mL of tert-butyl methyl ether, and dried in-vacuo to provide 39.0 g (88.6% yield) of the final title compound as a white solid.

A suspension of 10.0 g of the product, in a mixture of 49.0 mL of 2-propanol and 1.0 mL of water, was heated to solution. The solution is allowed to cool to ambient temperature effecting crystallization. The mixture is stirred for 1 hour at less than 29° C. and then the solids are collected by filtration. The solids are washed with 7 mL of 2-propanol and dried in-vacuo to provide 8.73 g of the recrystallized title compound.

$^1$H NMR, 500 MHz dmso-d6, 9.23 (bs, 1H), 8.94 (bs, 1H), 7.56 (t, 1H), 7.45 (d, 2H), 7.30 (d, 1H), 7.24 (d, 1H), 7.09 (d, 2H), 4.37 (m, 1H), 4.17 (m, 1H), 4.13 (dd, 1H), 4.03 (dd, 1H), 3.04 (m, 1H), 2.94 (m, 1H), 2.26 (s, 3H), 2.07 (m, 1H), 1.96 (m, 1H), 1.84 (m, 2H), 1.75 (m, 2H), 1.60 (m, 3H), 1.48 (m, 1H), 1.29 (m, 4H), 1.09 (m, 1H), 0.83 (t, 6H)

Mp=204° C. .

EXAMPLE 39

To establish that the iGluR$_5$ receptor subtype is mediating a pharmacological response in a neurological disease or disorder, the binding affinity of the panel compounds to the iGluR$_5$ receptor is first measured using standard methods. For example, the activity of compounds acting at the iGluR$_5$ receptor can be determined by radiolabelled ligand binding studies at the cloned and expressed human iGluR$_5$ receptor (Korczak et al., 1994, Recept. Channels 3; 41-49), and by whole cell voltage clamp electrophysiological recordings of currents in acutely isolated rat dorsal root ganglion neurons (Bleakman et al., 1996, Mol. Pharmacol. 49; 581-585). The selectivity of compounds acting at the iGluR$_5$ receptor subtype can then be determined by comparing antagonist activity at the iGluR$_5$ receptor with antagonist activity at other AMPA and kainate receptors. Methods useful for such comparison studies include: receptor-ligand binding studies and whole-cell voltage clamp electrophysiological recordings of functional activity at human GluR$_1$, GluR$_2$, GluR$_3$ and GluR$_4$ receptors (Fletcher et al., 1995, Recept. Channels 3; 21-31); receptor-ligand binding studies and whole-cell voltage clamp electrophysiological recordings of functional activity at human GluR$_6$ receptors (Hoo et al., Recept. Channels 2;327-338); and whole-cell voltage clamp electrophysiological recordings of functional activity at AMPA receptors in acutely isolated cerebellar Purkinje neurons (Bleakman et al., 1996, Mol. Pharmacol. 49; 581-585) and other tissues expressing AMPA receptors (Fletcher and Lodge, 1996, Pharmacol. Ther. 70; 65-89).

iGluR5 Antagonist Binding Affinity Profiles

Cell lines (HEK293 cells) stably transfected with human iGluR receptors are employed. Displacement of $^3$[H] AMPA by increasing concentrations of antagonist is measured on iGluR$_1$, iGluR$_2$, iGluR$_3$, and iGluR$_4$ expressing cells, while displacement of 3[H] kainate (KA) is measured on iGluR$_5$, iGluR$_6$, iGluR$_7$, and KA2-expressing cells. Estimated antagonist binding activity ($K_i$) in µM, for example, is determined for Compounds of Formula I. As an indicia of selectivity, the ratio of binding affinity to the iGluR$_2$ AMPA receptor subtype, versus the binding affinity to iGluR$_5$ kainate receptor subtype ($K_i$ at iGluR$_2$/$K_i$ at iGluR5) is also determined. The iGluR5 receptor antagonist compounds, as provided by the present invention, provide a $K_i$ at the iGluR$_5$ receptor subtype of less than 5000 µM, preferably less than 500 µM, even more preferably less than 50 µM, and most preferably less than 5 µM. The preferred selective iGluR5 receptor antagonists compounds, as provided by the present invention, display a greater binding affinity (lower $K_i$) for iGluR$_5$ than that for iGluR$_2$, preferably at least 10 fold greater for iGluR$_5$ than that for iGluR$_2$, and even more preferably at least 100 fold, and most preferably at least 1000 fold. than that for iGluR$_2$.

EXAMPLE 40

The following animal model may be employed to determine the ability of each of the compounds of Formula I to inhibit protein extravasation, an exemplary functional assay of the neuronal mechanism of migraine.

Animal Model of Dural Protein Extravasation

Harlan Sprague-Dawley rats (225-325 g) or guinea pigs from Charles River Laboratories (225-325 g) are anesthetized with sodium pentobarbital intraperitoneally (65 mg/kg or 45 mg/kg respectively) and placed in a stereotaxic frame (David Kopf Instruments) with the incisor bar set at −3.5 mm for rats or 4.0 mm for guinea pigs. Following a midline sagital scalp incision, two pairs of bilateral holes are drilled through the skull (6 mm posteriorly, 2.0 and 4.0 mm laterally in rats; 4 mm posteriorly and 3.2 and 5.2 mm laterally in guinea pigs, all coordinates referenced to bregma). Pairs of stainless steel stimulating electrodes, insulated except at the tips (Rhodes Medical Systems, Inc.), are lowered through the holes in both hemispheres to a depth of 9 mm (rats) or 10.5 mm (guinea pigs) from dura.

The femoral vein is exposed and a dose of the test compound is injected intravenously (i.v.) at a dosing volume of 1 ml/Kg or, in the alternative, test compound is administered orally (p.o) via gavage at a volume of 2.0 ml/Kg. Approximately 7 minutes post i.v. injection, a 50 mg/Kg dose of Evans Blue, a fluorescent dye, is also injected intravenously. The Evans Blue complexes with proteins in the blood and functions as a marker for protein extravasation. Exactly 10 minutes post-injection of the test compound, the left trigeminal ganglion is stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals are euthanized by exsanguination with 20 mL of saline. The top of the skull is removed to facilitate the collection of the dural membranes. The membrane samples are removed from both hemispheres, rinsed with water, and spread flat on microscopic slides. Once dried, the tissues are coverslipped with a 70% glycerol/water solution.

A fluorescence microscope (Zeiss) equipped with a grating monchromator and a spectrophotometer is used to quantify the amount of Evans Blue dye in each sample. An excitation wavelength of approximately 535 nm is utilized and the emission intensity at 600 nm is determined. The microscope is equipped with a motorized stage and also interfaced with a personal computer. This facilitates the computer-controlled movement of the stage with fluorescence measurements at 25 points (500 mm steps) on each dural sample. The mean and standard deviation of the measurements are determined by the computer.

The extravasation induced by the electrical stimulation of the trigeminal ganglion has an ipsilateral effect (i.e. occurs only on the side of the dura in which the trigeminal ganglion was stimulated). This allows the other (unstimulated) half of the dura to be used as a control. The ratio ("extravasation ratio") of the amount of extravasation in the dura from the stimulated side, over the amount of extravasation in the unstimulated side, is calculated. Control animals dosed with only with saline, yield an extravasation ratio of approximately 2.0 in rats and apprximately 1.8 in guinea pigs. In contrast, a compound which completely prevents the extravasation in the dura from the stimulated side would yield a ratio of approximately 1.0.

Dose-response curves are generated for each of the compounds of Formula I and the dose that inhibits the extravasation by 50% ($ID_{50}$) or 100% ($ID_{100}$) is approximated.

EXAMPLE 41

To demonstrate the utility of compounds of the present invention to treat pain or provide analgesic effects, several well known animal models may be employed. For example, international application WO 98/45270 describes the well known Formalin Test, which is described below:

Formalin Test

For example, male Sprague-Dawley rats (200-250 g; Charles River, Portage, Md.) are housed in group cages and maintained in a constant temperature and a 12 hour light/12 hour dark cycle 4-7 days before studies are performed. Animals have free access to food and water at all times prior to the day of the experiment.

Drugs or vehicles are administered intraperitoneally (i.p.) or orally (p.o.) by gavage in a volume of about 1 ml/kg. The test is performed in custom made Plexiglas® boxes about 25×25×20 cm in size (according to Shibata et al., Pain 38;347-352, 1989, Wheeler-Aceto et al., Pain, 40; 229-238, 1990). A mirror placed at the back of the cage allows the unhindered observation of the formalin injected paw. Rats are acclimated individually in the cubicles at least 1 hour prior to the experiment. All testing is conducted between, for example, 08:00 and 14:00 h and the testing room temperature is maintained at about 21-23° C.

Test compounds are administered about 30 minutes prior to the formalin injection. Formalin (50 micoliters of a 5% solution in saline) is injected subcutaneously into the dorsal lateral surface of the right hind paw with a 27 gauge needle. Observation is started immediately after the formalin injection. Formalin-induced pain is quantified by recording, for example, in 5 minute intervals, the number of formalin injected pawlicking events and the number of seconds each licking event lasts. These recordings are made for about 50 minutes after the formalin injection.

Several different scoring parameters have been reported for the formalin test. The total time spent licking and biting the injected paw is demonstrated to be most relevant (Coderre et al., *Eur. J. Neurosci.* 6; 1328-1334, 1993; Abbott et al., Pain, 60; 91-102, 1995) and may be chosen for the testing score. The early phase score is the sum of time spent licking, in seconds, from time 0 to 5 minutes. The late phase is scored in 5-minute blocks from 15 minutes to 40 minutes and is expressed accordingly or also by adding the total number of seconds spent licking from minute 15 to minute 40 of the observation period.

Data may be presented as means with standard errors of means (±SEM). Data may also be evaluated by one-way analysis of variance (ANOVA) and the appropriate contrasts analyzed by Dunnett "t" test for two sided comparisons. Differences are considered to be significant if, for example, the P-value is less than 0.05. Statistics may be determined at the 5 minute time point and at 5 minute intervals between 15 and 40 minutes. Where data are expressed as total amount of time spent licking in the late phase, statistics may be performed on the total time spent licking as well and may be indicated accordingly.

In addition to the Formalin Test, the well known Mouse Writhing Test, essentially as described in published International Application WO 00/028980, may also be employed to demonstrate the analgesic properties of compounds of the present invention.

Mouse Writhing Test

An accepted procedure for detecting and comparing the analgesic activity of different classes of analgesic drugs, for which there is a good correlation with human analgesic activity, is the prevention of acetic acid-induced writhing in mice. Mice are orally administered various doses of a test compound or placebo prior to testing. The mice are then injected intraperitoneally with acetic acid (0.55% solution, 10 mLg) five minutes prior to a designated observation period. Inhibition of writhing behavior is demonstrative of analgesic activity. Haubrich et al., "Pharmacology of pravadoline: a new analgesic agent", *The Journal of Pharmacology and Experimental Therapeutics*, 255 (1990) 511-522. For scoring purposes "writhe" is indicated by whole body stretching or contracting of the abdomen during an observation period beginning about five minutes after receiving the acetic acid.

$ED_{50}$ values, and their standard error of means (SEM), are determined using accepted numerical methods for all test compounds administered. For example, see R. E. Kirk (1982) "Experimental Design: Procedures for the behavioral sciences," 2nd ed. One method to establish the significance of the analgesic activity of a given test compound compared to that of another is to calculate the SEM values for each $ED_{50}$ value. If the SEM values do not overlap the line of addition, then the $ED_{50}$ values are significantly different from the line of addition.

Yet another accepted animal model to demonstrate the ability of a particular compound to treat pain, or provide analgesic effects, is the well known Rat Model of Carrageenan-induced Thermal Hyperalgesia, also described in published International Application WO 00/028980.

Carrageenan-induced Thermal Hyperalgesia in Rats

Another accepted method for detecting and comparing the analgesic activity of different classes of analgesic compounds for which there is good correlation with human analgesic activity is the reversal of carrageenan-induced thermal hyperalgesia in rats (Hargreaves et al. *Pain* 32:77-88, 1988).

Rats are administered a dose test compound or vehicle and then injected subcutaneously into one hindpaw, with carrageenan (1.5% w/v, 100 μl). The response to noxious thermal stimulus is determined two hours later using a commercially available thermal plantar device (Ugo Basil, Italy) according to established methods (Hargreaves et al. *Pain* 32:77-88, 1988). Briefly, animals are habituated to a plastic behavioral enclosure for 5 min. A heat source is positioned directly beneath a hindpaw and the time taken for hindpaw withdrawal monitored automatically. If the animal does not respond within 20 sec, the stimulus is automatically terminated to prevent tissue damage. Measurements for both the injured and contralateral (control) hindpaw are recorded. Thermal hyperalgesia is evidenced by a shorter response latency by the injured as compared to the control paw.

$ED_{50}$ values and their standard error of means (SEM) are determined using accepted numerical methods. For example, see R. E. Kirk (1982) "Experimental Design: Procedures for the behavioral sciences," 2nd ed.

We claim:

1. A compound of the formula

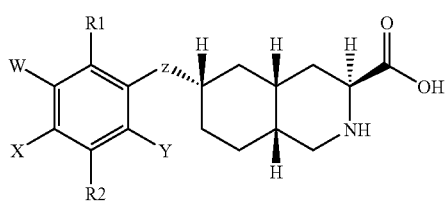

wherein
   Z represents an oxygen atom;
   $R^1$ represents $CO_2H$;
   $R^2$ represents hydrogen, halo, or aryl;
   W represents hydrogen
   X represents hydrogen, halo, or $NO_2$; and
   Y represents hydrogen,
   or a pharmaceutically acceptable salt thereof.

2. A compound according to claim 1 selected from the group consisting of
   (3S, 4aS, 6S, 8aR) 6-(4-carboxy-biphenyl-3-yloxy)-1,2,3,4,4a,5,6,7,8,8a-decahydroisoquinoline-3-carboxylic acid;
   (3S, 4aS, 6S, 8aR) 6-(2-carboxy-5-chloro-phenoxy)-1,2,3,4,4a,5,6,7,8,8a-decahydroisoquinoline-3-carboxylic acid;
   (3S,4aS, 6S, 8aR) 6-(2-carboxy-4,5-difluoro-phenoxy)-1,2,3,4,4a,5,6,7,8,8a-decahydroisoquinoline-3-carboxylic acid;
   (3S, 4aS, 6S, 8aR) 6-(2-carboxy-4-chloro-phenoxy)-1,2,3,4,4a,5,6,7,8,8a-decahydroisoquinoline-3-carboxylic acid; and
   (3S, 4aS, 6S, 8a R) 6-(2-carboxy-4-nitro-phenoxy)-1,2,3,4,4a,5,6,7,8,8a-decahydroisoquinoline-3-carboxylic acid, or a pharmaceutically acceptable salt thereof.

3. A compound of the formula

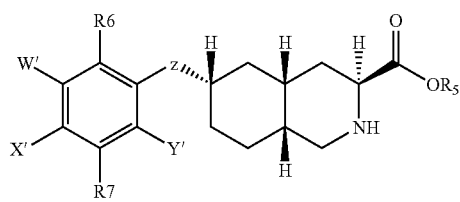

wherein
   Z represents an oxygen atom;
   $R^5$ represents hydrogen or $(C_1-C_{10})$alkyl;
   $R^6$ represents $CO_2R^9$;
   $R^7$ represents hydrogen, halo, or aryl;
   W' represents hydrogen;
   X' represents hydrogen, halo, or $NO_2$;
   Y' represents hydrogen, and
   $R^9$ represents hydrogen or $(C_1-C_{10})$alkyl, with the proviso that at least one of $R^5$ and $R^9$ is other than hydrogen, or a pharmaceutically acceptable salt thereof.

4. A compound according to claim 3 selected from the group consisting of
   ethyl (3S, 4aS, 6S, 8aR) 6-(4-ethoxycarbonyl-biphenyl-3-yloxy)-1,2,3,4,4a,5,6,7,8,8a-decahydroisoquinoline-3-carboxylate; and
   ethyl (3S, 4aS, 6S, 8aR) 6-(5-chloro-2-ethoxycarbonyl-phenoxy)-1,2,3,4,4a,5,6,7,8,8a-decahydroisoquinoline-3-carboxylate,
   or a pharmaceutically acceptable salt thereof.

5. A method of treating pain or migraine comprising administering to a patient in need thereof, an effective amount of a compound or salt according to claim 1.

6. A method of treating pain or migraine comprising administering to a patient in need thereof, an effective amount of a compound or salt according to claim 3.

7. A pharmaceutical composition comprising a compound or salt according to claim 3, in combination with a pharmaceutically acceptable carrier, diluent, or excipient.

* * * * *

UNITED STATES PATENT AND TRADEMARK OFFICE
CERTIFICATE OF CORRECTION

PATENT NO. : 7,601,738 B2
APPLICATION NO. : 11/302869
DATED : October 13, 2009
INVENTOR(S) : Thomas John Bleisch It is certified that error appears in the above-identified patent and that said Letters Patent is hereby corrected as shown below:

On the face page, column 1, under OTHER PUBLICATIONS, line 1, delete the word ""Structurre" and insert --"Structure--, therefor.

On the face page, column 1, under OTHER PUBLICATIONS, line 6, before "Prodrug" insert --a--.

On the face page, column 2, under OTHER PUBLICATIONS, line 7, delete "Proctor," and insert --Procter,--, therefor.

On the face page, column 2, under OTHER PUBLICATIONS, line 23, delete "Methesda," and insert --Bethesda--, therefor.

On the face page, column 2, under OTHER PUBLICATIONS, line 24, delete "Mitsilostas" and insert --Mitsikostas--, therefor.

In column 90, line 12, in Claim 2, delete "(3S,4aS," and insert --(3S, 4aS,--, therefor.

In column 90, line 18, in Claim 2, delete "8a R)" and insert --8aR)--, therefor.

Signed and Sealed this

Twenty-ninth Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,601,738 B2
APPLICATION NO. : 11/302869
DATED : October 13, 2009
INVENTOR(S) : Thomas John Bleisch et al.

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 587 days.

should read (*) Notice: Subject to any disclaimer, the term of this patent is extended or adjusted under 35 U.S.C. 154(b) by 890 days.

Signed and Sealed this

Fourth Day of May, 2010

David J. Kappos
*Director of the United States Patent and Trademark Office*